US007144574B2

(12) United States Patent
Rasmussen et al.

(10) Patent No.: US 7,144,574 B2
(45) Date of Patent: Dec. 5, 2006

(54) INTERFERON β VARIANTS AND CONJUGATES

(75) Inventors: Poul Baad Rasmussen, Soeborg (DK); Grethe Rasmussen, Farum (DK); Kim Vilbour Andersen, Broenshoej (DK); Claus Bornaes, Hellerup (DK)

(73) Assignee: Maxygen ApS, Hoersholm (DK)

( * ) Notice: Subject to any disclaimer, the term of this patent is extended or adjusted under 35 U.S.C. 154(b) by 383 days.

(21) Appl. No.: 10/084,706

(22) Filed: Feb. 26, 2002

(65) Prior Publication Data

US 2003/0170206 A1 Sep. 11, 2003

Related U.S. Application Data

(63) Continuation-in-part of application No. 09/648,569, filed on Aug. 25, 2000, now Pat. No. 6,531,122.

(60) Provisional application No. 60/357,945, filed on Feb. 19, 2002, provisional application No. 60/343,436, filed on Dec. 21, 2001, provisional application No. 60/316,170, filed on Aug. 30, 2001, provisional application No. 60/302,140, filed on Jun. 29, 2001, provisional application No. 60/272,116, filed on Feb. 27, 2001, provisional application No. 60/202,248, filed on May 5, 2000, provisional application No. 60/189,599, filed on Mar. 15, 2000, provisional application No. 60/169,077, filed on Dec. 6, 1999, provisional application No. 60/160,782, filed on Oct. 21, 1999.

(30) Foreign Application Priority Data

| Aug. 27, 1999 | (DK) | 1999 01197 |
| Nov. 26, 1999 | (DK) | 1999 01691 |
| Feb. 7, 2000 | (DK) | 2000 00194 |
| Mar. 7, 2000 | (DK) | 2000 00363 |
| Apr. 14, 2000 | (DK) | 2000 00642 |
| Mar. 1, 2001 | (DK) | 2001 00333 |

(51) Int. Cl.
*A61K 38/21* (2006.01)
*A61K 88/00* (2006.01)
*C07K 17/00* (2006.01)

(52) U.S. Cl. .......... 424/85.6; 424/85.4; 514/12; 530/350; 530/351; 530/395; 530/397

(58) Field of Classification Search ........ 435/69.57, 435/442; 530/350, 351; 424/85.6
See application file for complete search history.

(56) References Cited

U.S. PATENT DOCUMENTS

| 4,588,585 A | 5/1986 | Mark et al. |
| 4,686,191 A | 8/1987 | Itoh et al. |
| 4,769,233 A | 9/1988 | Bell et al. |
| 4,904,584 A | 2/1990 | Shaw |
| 4,914,033 A | 4/1990 | Bell et al. |
| 4,917,888 A | 4/1990 | Katre et al. |
| 4,966,843 A | 10/1990 | McCormick et al. |
| 5,206,344 A | 4/1993 | Katre et al. |
| 5,218,092 A | 6/1993 | Sasaki et al. |
| 5,376,567 A | 12/1994 | McCormick et al. |
| 5,382,657 A | 1/1995 | Karasiewicz et al. |
| 5,545,723 A | 8/1996 | Goelz et al. |
| 5,738,846 A | 4/1998 | Greenwald et al. |
| 5,795,779 A | 8/1998 | McCormick et al. |
| 6,531,122 B1 * | 3/2003 | Pedersen et al. ........ 424/85.6 |

FOREIGN PATENT DOCUMENTS

| EP | 083 069 | 9/1987 |
| EP | 0 287 075 B2 | 10/1988 |
| EP | 0 370 205 A2 | 5/1990 |
| EP | 041 313 | 9/1990 |
| EP | 229 108 | 12/1990 |
| EP | 260 350 | 2/1992 |
| EP | 0 529 300 B1 | 3/1993 |
| EP | 287 075 | 1/1995 |
| EP | 539 300 | 2/1996 |
| EP | 593 868 | 4/1998 |
| WO | WO 95/25170 | 9/1995 |
| WO | WO 95/27502 A1 | 10/1995 |
| WO | WO 98/35026 A1 | 8/1998 |
| WO | WO 98/48018 | 10/1998 |
| WO | WO 99/03887 | 1/1999 |
| WO | WO 99/55377 | 11/1999 |
| WO | WO 99/55377 A2 | 11/1999 |
| WO | WO 99/67291 | 12/1999 |

(Continued)

OTHER PUBLICATIONS

Ngo et al., 1994, The Protein Folding Problem and Tertiary Structure Prediction, pp. 492-495.*

(Continued)

*Primary Examiner*—Christine J. Saoud
*Assistant Examiner*—Jegatheesan Seharaseyon
(74) *Attorney, Agent, or Firm*—Margaret A. Powers; Joanne R. Petithory

(57) ABSTRACT

The invention relates to a conjugate exhibiting interferon β (IFNB) activity and comprising at least one first non-polypeptide moiety covalently attached to an IFNB polypeptide, the amino acid sequence of which differs from that of wildtype human IFNB in at least one introduced and at least one removed amino acid residue comprising an attachment group for said first non-polypeptide moiety. The first non-polypeptide moiety is e.g. a polymer molecule or a sugar moiety. The conjugate finds particular use in therapy. The invention also relates to a glycosylated variant of a parent IFNB polypeptide comprising at least one in vivo glycosylation site, wherein an amino acid residue of said parent polypeptide located close to said glycosylation site has been modified to obtain the variant polypeptide having an increased glycosylation as compared to the glycosylation of the parent polypeptide.

19 Claims, 3 Drawing Sheets

FOREIGN PATENT DOCUMENTS

| | | |
|---|---|---|
| WO | WO 00/23114 | 4/2000 |
| WO | WO 00/23472 | 4/2000 |
| WO | WO 00/26354 | 5/2000 |
| WO | WO 01/15736 A2 | 3/2001 |

OTHER PUBLICATIONS

Wells, Aditivity of Mutational Effects in Proteins, 1990, Biochemistry, vol. 26, No. 37, pp. 8509-8517.*

Apweiler et al. On the frequency of protein glycosylation, as deducted from analysis of the SWISS-PROT database (1999). BBA 1473 pp. 4-8.*

O'Connell, et al., "The Influence of Flanking Sequences on O-Glycosylation", *Biochemical and Biophysical Research Communications*, 1991, pp. 1024-1030, 180:2.

Fierlbeck et al., "Neutralising interferon β antibodies in melanoma patients treated with recombinant and natural interferon β " *Cancer Immunol Immunother* (1994) 39:263-268.

Karpusas et al., "The Structure of Human Interferon- β: Implications for activity" *CMLS* 54 (1998) 1203-1216.

Karpusas et al. "The crystal structure of human interferon β at 2.2 A resolution" Proc. Nat. Acad. Sci. USA (1997) 94:11813-11818.

Mayorga et al., "Antibodies to Commercially Available Interferon-Bet Molecules in Multiple Sclerosis Patients Treated with Natural Interferon-Beta" *Int. Arch. Allery Immunol* 1999; 118:368-371.

Munschauer et al., "Managing Side Effects of Interferon-Beta in Patients with Relapsing-Remitting Multipule Sclerosis" *Clinical Therapeutics* vol. 19, No. 5, 1997 883-893.

Redlich et al., "Antibodies that neutralize human β interferon biologic activity recognizing a linear epitope: Analysis by synthetic peptide mapping" *Proc. Natl. Acad. Sci. USA* vol. 88, pp. 4040-4044 May 1991.

Rudick et al., "Incidence and significance of neutralizing antibodies to interferon beta-1a in multipule sclerosis" *Neurology* May 1889, 50: 1266-1272.

Runkel et al., Structural and Functional Differences Between Glycosylated and Non-Glycosylated Forms of Human Interferon- β (IFN- β)*Pharmaceutical Research* vol. 15, No. 4, 1998, 641-649.

Runkel et al, 1998, Jour. Biol. Chem. Difference in Activity between α and β Type 1 Interferons Explored by Mutational Analysis 273, No. 14, pp. 8003-8008.

Senda et al., "Refined Crystal Structure of Recombinant Murine Interferon- β at 2.15 A Resolution" *J. Mil. Biol.* (1995) 253, 187-207.

Stewart et al, DNA Chemical Mutagenesis of Human Interferon- β: Construction, Expression in E. coli, and Biological Activity of Sodium Bisulfite-Induced Mutations vol. 6 No. 2 1987 p. 119-128.

Tanigunchi, et al., "The nucleotide sequence of human fibroblast interferon cDNA" *Gene* 10 (1980) 11-15.

Yong et al., "Interferon beta in the treatment of multiple sclerosis" *Neurology* 1998; 51: 682-689.

\* cited by examiner

SEQUENCE LISTING

```
<160> NUMBER OF SEQ ID NOS: 57

<210> SEQ ID NO 1
<211> LENGTH: 840
<212> TYPE: DNA
<213> ORGANISM: Homo sapiens
<220> FEATURE:
<221> NAME/KEY: CDS
<222> LOCATION: (76)...(636)

<400> SEQUENCE: 1
acattctaac tgcaaccttt cgaagccttt gctctggcac aacaggtagt aggcgacact         60
gttcgtgttg tcaac atg acc aac aag tgt ctc ctc caa att gct ctc ctg        111
                Met Thr Asn Lys Cys Leu Leu Gln Ile Ala Leu Leu
                  1               5                  10 ttg tgc ttc tcc act aca gct ctt tcc atg agc tac aac ttg ctt gga        159
Leu Cys Phe Ser Thr Thr Ala Leu Ser Met Ser Tyr Asn Leu Leu Gly
         15                  20                  25 ttc cta caa aga agc agc aat ttt cag tgt cag aag ctc ctg tgg caa        207
Phe Leu Gln Arg Ser Ser Asn Phe Gln Cys Gln Lys Leu Leu Trp Gln
 30                  35                  40 ttg aat ggg agg ctt gaa tac tgc ctc aag gac agg atg aac ttt gac        255
Leu Asn Gly Arg Leu Glu Tyr Cys Leu Lys Asp Arg Met Asn Phe Asp
 45                  50                  55                  60 atc cct gag gag att aag cag ctg cag cag ttc cag aag gag gac gcc        303
Ile Pro Glu Glu Ile Lys Gln Leu Gln Gln Phe Gln Lys Glu Asp Ala
                 65                  70                  75 gca ttg acc atc tat gag atg ctc cag aac atc ttt gct att ttc aga        351
Ala Leu Thr Ile Tyr Glu Met Leu Gln Asn Ile Phe Ala Ile Phe Arg
             80                  85                  90 caa gat tca tct agc act ggc tgg aat gag act att gtt gag aac ctc        399
Gln Asp Ser Ser Ser Thr Gly Trp Asn Glu Thr Ile Val Glu Asn Leu
             95                 100                 105 ctg gct aat gtc tat cat cag ata aac cat ctg aag aca gtc ctg gaa        447
Leu Ala Asn Val Tyr His Gln Ile Asn His Leu Lys Thr Val Leu Glu
        110                 115                 120 gaa aaa ctg gag aaa gaa gat ttc acc agg gga aaa ctc atg agc agt        495
Glu Lys Leu Glu Lys Glu Asp Phe Thr Arg Gly Lys Leu Met Ser Ser
125                 130                 135                 140 ctg cac ctg aaa aga tat tat ggg agg att ctg cat tac ctg aag gcc        543
Leu His Leu Lys Arg Tyr Tyr Gly Arg Ile Leu His Tyr Leu Lys Ala
                145                 150                 155 aag gag tac agt cac tgt gcc tgg acc ata gtc aga gtg gaa atc cta        591
Lys Glu Tyr Ser His Cys Ala Trp Thr Ile Val Arg Val Glu Ile Leu
            160                 165                 170 agg aac ttt tac ttc att aac aga ctt aca ggt tac ctc cga aac             636
Arg Asn Phe Tyr Phe Ile Asn Arg Leu Thr Gly Tyr Leu Arg Asn
        175                 180                 185 tgaagatctc ctagcctgtg cctctgggac tggacaattg cttcaagcat tcttcaacca        696
gcagatgctg tttaagtgac tgatggctaa tgtactgcat atgaaaggac actagaagat        756
```

```
tttgaaattt ttattaaatt atgagttatt tttatttatt taaattttat tttggaaaat        816
aaattatttt tggtgcaaaa gtca                                                840
```

<210> SEQ ID NO 2
<211> LENGTH: 166
<212> TYPE: PRT
<213> ORGANISM: Homo sapiens
<220> FEATURE:
<221> NAME/KEY: CHAIN
<222> LOCATION: (1)...(166)
<223> OTHER INFORMATION: hIFNB mature sequence

<400> SEQUENCE: 2

```
Met Ser Tyr Asn Leu Leu Gly Phe Leu Gln Arg Ser Ser Asn Phe Gln
 1               5                  10                  15

Cys Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165
```

<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3

```
ggctagcgtt taaacttaag cttcgccacc atgaccaaca agtgcctgct ccagatcgcc        60
ctgctcctgt                                                                70
```

<210> SEQ ID NO 4
<211> LENGTH: 70
<212> TYPE: DNA
<213> ORGANISM: Artificial Sequence
<220> FEATURE:
<223> OTHER INFORMATION: primer

<400> SEQUENCE: 4

```
acaacctgct cggcttcctg cagaggagtt cgaacttcca gtgccagaag ctcctgtggc        60
agctgaacgg                                                                70
```

<210> SEQ ID NO 5
<211> LENGTH: 70
<212> TYPE: DNA
<213> ORGANISM: Artificial Sequence
<220> FEATURE:
<223> OTHER INFORMATION: primer

<400> SEQUENCE: 5
gaacttcgac atccccgagg aaatcaagca gctgcagcag ttccagaagg aggacgccgc    60
tctgaccatc                                                          70

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
ttccgccagg actccagctc caccggttgg aacgagacca tcgtggagaa cctgctggcc    60
aacgtgtacc                                                          70

<210> SEQ ID NO 7
<211> LENGTH: 70
<212> TYPE: DNA
<213> ORGANISM: Artificial Sequence
<220> FEATURE:
<223> OTHER INFORMATION: primer

<400> SEQUENCE: 7
aggagaagct ggagaaggag gacttcaccc gcggcaagct gatgagctcc ctgcacctga    60
agcgctacta                                                          70

<210> SEQ ID NO 8
<211> LENGTH: 70
<212> TYPE: DNA
<213> ORGANISM: Artificial Sequence
<220> FEATURE:
<223> OTHER INFORMATION: primer

<400> SEQUENCE: 8
ggagtacagc cactgcgcct ggaccatcgt acgcgtggag atcctgcgca acttctactt    60
catcaaccgc                                                          70

<210> SEQ ID NO 9
<211> LENGTH: 70
<212> TYPE: DNA
<213> ORGANISM: Artificial Sequence
<220> FEATURE:
<223> OTHER INFORMATION: primer

<400> SEQUENCE: 9
caccacactg gactagtgga tccttatcag ttgcgcaggt agccggtcag gcggttgatg    60
aagtagaagt                                                          70

<210> SEQ ID NO 10
<211> LENGTH: 70
<212> TYPE: DNA
<213> ORGANISM: Artificial Sequence
<220> FEATURE:
<223> OTHER INFORMATION: primer

<400> SEQUENCE: 10

```
aggcgcagtg gctgtactcc ttggccttca ggtagtgcag gatgcggcca tagtagcgct    60
tcaggtgcag                                                            70

<210> SEQ ID NO 11
<211> LENGTH: 70
<212> TYPE: DNA
<213> ORGANISM: Artificial Sequence
<220> FEATURE:
<223> OTHER INFORMATION: primer

<400> SEQUENCE: 11
ctccttctcc agcttctcct ccagcacggt cttcaggtgg ttgatctggt ggtacacgtt    60
ggccagcagg                                                            70

<210> SEQ ID NO 12
<211> LENGTH: 70
<212> TYPE: DNA
<213> ORGANISM: Artificial Sequence
<220> FEATURE:
<223> OTHER INFORMATION: primer

<400> SEQUENCE: 12
gagctggagt cctggcggaa gatggcgaag atgttctgca gcatctcgta gatggtcaga    60
gcggcgtcct                                                            70

<210> SEQ ID NO 13
<211> LENGTH: 70
<212> TYPE: DNA
<213> ORGANISM: Artificial Sequence
<220> FEATURE:
<223> OTHER INFORMATION: primer

<400> SEQUENCE: 13
cctcggggat gtcgaagttc atcctgtcct tcaggcagta ctccaggcgc ccgttcagct    60
gccacaggag                                                            70

<210> SEQ ID NO 14
<211> LENGTH: 70
<212> TYPE: DNA
<213> ORGANISM: Artificial Sequence
<220> FEATURE:
<223> OTHER INFORMATION: primer

<400> SEQUENCE: 14
caggaagccg agcaggttgt agctcatcga tagggccgtg gtgctgaagc acaggagcag    60
ggcgatctgg                                                            70

<210> SEQ ID NO 15
<211> LENGTH: 70
<212> TYPE: DNA
<213> ORGANISM: Artificial Sequence
<220> FEATURE:
<223> OTHER INFORMATION: primer

<400> SEQUENCE: 15
ctgctccaga tcgccctgct cctgtgcttc agcaccacgg ccctatcgat gaagcaccag    60
caccagcatc                                                            70

<210> SEQ ID NO 16
<211> LENGTH: 70
<212> TYPE: DNA
<213> ORGANISM: Artificial Sequence
```

-continued

```
<220> FEATURE:
<223> OTHER INFORMATION: primer

<400> SEQUENCE: 16
cactgcttac tggcttatcg aaattaatac gactcactat agggagaccc aagctggcta      60
gcgtttaaac                                                              70

<210> SEQ ID NO 17
<211> LENGTH: 70
<212> TYPE: DNA
<213> ORGANISM: Artificial Sequence
<220> FEATURE:
<223> OTHER INFORMATION: primer

<400> SEQUENCE: 17
caggaagccg agcaggttgt agctcatctg ttggtgttga tgttggtgct gatgctggtg      60
ctggtgcttc                                                              70

<210> SEQ ID NO 18
<211> LENGTH: 70
<212> TYPE: DNA
<213> ORGANISM: Artificial Sequence
<220> FEATURE:
<223> OTHER INFORMATION: primer

<400> SEQUENCE: 18
agcagggcga tctggagcag gcacttgttg gtcatggtgg cgaagcttaa gtttaaacgc      60
tagccagctt                                                              70

<210> SEQ ID NO 19
<211> LENGTH: 40
<212> TYPE: DNA
<213> ORGANISM: Artificial Sequence
<220> FEATURE:
<223> OTHER INFORMATION: primer

<400> SEQUENCE: 19
ccgtcagatc ctaggctagc ttattgcggt agtttatcac                             40

<210> SEQ ID NO 20
<211> LENGTH: 32
<212> TYPE: DNA
<213> ORGANISM: Artificial Sequence
<220> FEATURE:
<223> OTHER INFORMATION: primer

<400> SEQUENCE: 20
gagctcggta ccaagctttt aagagctgta at                                     32

<210> SEQ ID NO 21
<211> LENGTH: 77
<212> TYPE: DNA
<213> ORGANISM: Artificial Sequence
<220> FEATURE:
<223> OTHER INFORMATION: primer

<400> SEQUENCE: 21
gctgaacggg cgcctggagt actgcctgaa ggacaggatg aacttcgaca tccccgagga      60
aatccgccag ctgcagc                                                      77

<210> SEQ ID NO 22
<211> LENGTH: 35
<212> TYPE: DNA
```

<213> ORGANISM: Artificial Sequence
<220> FEATURE:
<223> OTHER INFORMATION: primer

<400> SEQUENCE: 22
tctccacgcg tacgatggtc caggcgcagt ggctg                35

<210> SEQ ID NO 23
<211> LENGTH: 70
<212> TYPE: DNA
<213> ORGANISM: Artificial Sequence
<220> FEATURE:
<223> OTHER INFORMATION: primer

<400> SEQUENCE: 23
caccacactg gactagtgga tccttatcag ttgcgcaggt agccggtcag gcggttgatg     60
aagtagaagt                                                           70

<210> SEQ ID NO 24
<211> LENGTH: 31
<212> TYPE: DNA
<213> ORGANISM: Artificial Sequence
<220> FEATURE:
<223> OTHER INFORMATION: primer

<400> SEQUENCE: 24
catcagcttg ccggtggtgt tgtcctcctt c                                   31

<210> SEQ ID NO 25
<211> LENGTH: 31
<212> TYPE: DNA
<213> ORGANISM: Artificial Sequence
<220> FEATURE:
<223> OTHER INFORMATION: primer

<400> SEQUENCE: 25
gaaggaggac aacaccaccg gcaagctgat g                                   31

<210> SEQ ID NO 26
<211> LENGTH: 40
<212> TYPE: DNA
<213> ORGANISM: Artificial Sequence
<220> FEATURE:
<223> OTHER INFORMATION: primer

<400> SEQUENCE: 26
cacactggac tagtaagctt ttatcagttg cgcaggtagc                          40

<210> SEQ ID NO 27
<211> LENGTH: 47
<212> TYPE: DNA
<213> ORGANISM: Artificial Sequence
<220> FEATURE:
<223> OTHER INFORMATION: primer

<400> SEQUENCE: 27
gaggagttcg aacttccagt gccagcgcct cctgtggcag ctgaacg                  47

<210> SEQ ID NO 28
<211> LENGTH: 29
<212> TYPE: DNA
<213> ORGANISM: Artificial Sequence
<220> FEATURE:
<223> OTHER INFORMATION: primer

<400> SEQUENCE: 28
cgcggatcca tatgaccaac aagtgcctg                                        29

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
cgcggatcct tatcagttgc gcag                                              24

<210> SEQ ID NO 30
<211> LENGTH: 33
<212> TYPE: DNA
<213> ORGANISM: Artificial Sequence
<220> FEATURE:
<223> OTHER INFORMATION: primer

<400> SEQUENCE: 30
tttaaactgg atccagccac catgaccaac aag                                    33

<210> SEQ ID NO 31
<211> LENGTH: 63
<212> TYPE: DNA
<213> ORGANISM: Artificial Sequence
<220> FEATURE:
<223> OTHER INFORMATION: primer

<400> SEQUENCE: 31
cggccatagt agcgcttcag gtgcaggag ctcatcagct tgccggtggt gttgtcctcc         60
ttc                                                                     63

<210> SEQ ID NO 32
<211> LENGTH: 63
<212> TYPE: DNA
<213> ORGANISM: Artificial Sequence
<220> FEATURE:
<223> OTHER INFORMATION: primer

<400> SEQUENCE: 32
gaaggaggac aacaccaccg gcaagctgat gagctccctg cacctgaagc gctactatgg        60
ccg                                                                     63

<210> SEQ ID NO 33
<211> LENGTH: 30
<212> TYPE: DNA
<213> ORGANISM: Artificial Sequence
<220> FEATURE:
<223> OTHER INFORMATION: primer

<400> SEQUENCE: 33
ggcgtcctcc ttggtgaagt tctgcagctg                                        30

<210> SEQ ID NO 34
<211> LENGTH: 39
<212> TYPE: DNA
<213> ORGANISM: Artificial Sequence
<220> FEATURE:
<223> OTHER INFORMATION: primer

<400> SEQUENCE: 34
atatatccca agctttatc agttgcgcag gtagccggt                               39

```
<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
cagctgcaga acttcaccaa ggaggacgcc                                         30

<210> SEQ ID NO 36
<211> LENGTH: 34
<212> TYPE: DNA
<213> ORGANISM: Artificial Sequence
<220> FEATURE:
<223> OTHER INFORMATION: primer

<400> SEQUENCE: 36
cgcggatcca gccaccatga ccaacaagtg cctg                                    34

<210> SEQ ID NO 37
<211> LENGTH: 89
<212> TYPE: DNA
<213> ORGANISM: Artificial Sequence
<220> FEATURE:
<223> OTHER INFORMATION: primer

<400> SEQUENCE: 37
aactggatcc agccaccatg accaacaagt gcctgctcca gatcgccctg ctcctgtgct        60
tcagcaccac ggccctagcc cagagctac                                          89

<210> SEQ ID NO 38
<211> LENGTH: 92
<212> TYPE: DNA
<213> ORGANISM: Artificial Sequence
<220> FEATURE:
<223> OTHER INFORMATION: primer

<400> SEQUENCE: 38
aactggatcc agccaccatg accaacaagt gcctgctcca gatcgccctg ctcctgtgct        60
tcagcaccac ggccctagcc cagatgagct ac                                      92

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
gtcctccttg gtgaagttga acagctgctt                                         30

<210> SEQ ID NO 40
<211> LENGTH: 30
<212> TYPE: DNA
<213> ORGANISM: Artificial Sequence
<220> FEATURE:
<223> OTHER INFORMATION: primer

<400> SEQUENCE: 40
aagcagctgt tcaacttcac caaggaggac                                         30

<210> SEQ ID NO 41
<211> LENGTH: 30
```

-continued

```
<212> TYPE: DNA
<213> ORGANISM: Artificial Sequence
<220> FEATURE:
<223> OTHER INFORMATION: primer

<400> SEQUENCE: 41
gtcctccttg gtgaagttca ccagctgctt                                    30

<210> SEQ ID NO 42
<211> LENGTH: 30
<212> TYPE: DNA
<213> ORGANISM: Artificial Sequence
<220> FEATURE:
<223> OTHER INFORMATION: primer

<400> SEQUENCE: 42
aagcagctgg tgaacttcac caaggaggac                                    30

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
gtcctccttg gtgaagttcc acagctgctt                                    30

<210> SEQ ID NO 44
<211> LENGTH: 30
<212> TYPE: DNA
<213> ORGANISM: Artificial Sequence
<220> FEATURE:
<223> OTHER INFORMATION: primer

<400> SEQUENCE: 44
aagcagctgt ggaacttcac caaggaggac                                    30

<210> SEQ ID NO 45
<211> LENGTH: 30
<212> TYPE: DNA
<213> ORGANISM: Artificial Sequence
<220> FEATURE:
<223> OTHER INFORMATION: primer

<400> SEQUENCE: 45
cagcttgccg gtggtgttga actccttctc                                    30

<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46
gagaaggagt tcaacaccac cggcaagctg                                    30

<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47
```
cagcttgccg gtggtgttca cctccttctc                                30

<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48
gagaaggagg tgaacaccac cggcaagctg                                30

<210> SEQ ID NO 49
<211> LENGTH: 6
<212> TYPE: PRT
<213> ORGANISM: Artificial Sequence
<220> FEATURE:
<223> OTHER INFORMATION: peptide tag

<400> SEQUENCE: 49

His His His His His His
 1               5

<210> SEQ ID NO 50
<211> LENGTH: 8
<212> TYPE: PRT
<213> ORGANISM: Artificial Sequence
<220> FEATURE:
<223> OTHER INFORMATION: peptide tag

<400> SEQUENCE: 50

Met Lys His His His His His His
 1               5

<210> SEQ ID NO 51
<211> LENGTH: 10
<212> TYPE: PRT
<213> ORGANISM: Artificial Sequence
<220> FEATURE:
<223> OTHER INFORMATION: peptide tag

<400> SEQUENCE: 51

Met Lys His His Ala His His Gln His His
 1               5                  10

<210> SEQ ID NO 52
<211> LENGTH: 14
<212> TYPE: PRT
<213> ORGANISM: Artificial Sequence
<220> FEATURE:
<223> OTHER INFORMATION: peptide tag

<400> SEQUENCE: 52

Met Lys His Gln His Gln His Gln His Gln His Gln His Gln
 1               5                  10

<210> SEQ ID NO 53
<211> LENGTH: 10
<212> TYPE: PRT
<213> ORGANISM: Artificial Sequence
<220> FEATURE:
<223> OTHER INFORMATION: peptide tag

<400> SEQUENCE: 53

Glu Gln Lys Leu Ile Ser Glu Glu Asp Leu
 1               5                  10

-continued

```
<210> SEQ ID NO 54
<211> LENGTH: 8
<212> TYPE: PRT
<213> ORGANISM: Artificial Sequence
<220> FEATURE:
<223> OTHER INFORMATION: peptide tag

<400> SEQUENCE: 54

Asp Tyr Lys Asp Asp Asp Asp Lys
1               5

<210> SEQ ID NO 55
<211> LENGTH: 9
<212> TYPE: PRT
<213> ORGANISM: Artificial Sequence
<220> FEATURE:
<223> OTHER INFORMATION: peptide tag

<400> SEQUENCE: 55

Tyr Pro Tyr Asp Val Pro Asp Tyr Ala
1               5

<210> SEQ ID NO 56
<211> LENGTH: 166
<212> TYPE: PRT
<213> ORGANISM: Artificial Sequence
<220> FEATURE:
<223> OTHER INFORMATION: Synthetic construct

<400> SEQUENCE: 56

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Asn Phe Thr Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Phe Asn Thr
            100                 105                 110

Thr Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 57
<211> LENGTH: 166
<212> TYPE: PRT
<213> ORGANISM: Artificial Sequence
<220> FEATURE:
<223> OTHER INFORMATION: Synthetic construct

<400> SEQUENCE: 57
```

```
-continued

Met Ser Tyr Asn Leu Leu Gly Phe Leu Gln Arg Ser Ser Asn Phe Gln
 1           5                   10                  15

Ser Gln Arg Leu Leu Trp Gln Leu Asn Gly Arg Leu Glu Tyr Cys Leu
            20                  25                  30

Arg Asp Arg Met Asn Phe Asp Ile Pro Glu Glu Ile Arg Gln Leu Gln
            35                  40              45

Asn Phe Thr Lys Glu Asp Ala Ala Leu Thr Ile Tyr Glu Met Leu Gln
     50              55                  60

Asn Ile Phe Ala Ile Phe Arg Gln Asp Ser Ser Ser Thr Gly Trp Asn
 65              70              75                       80

Glu Thr Ile Val Glu Asn Leu Leu Ala Asn Val Tyr His Gln Ile Asn
                85              90              95

His Leu Lys Thr Val Leu Glu Glu Lys Leu Glu Lys Glu Phe Asn Thr
            100             105             110

Thr Gly Lys Leu Met Ser Ser Leu His Leu Lys Arg Tyr Tyr Gly Arg
            115             120             125

Ile Leu His Tyr Leu Lys Ala Lys Glu Tyr Ser His Cys Ala Trp Thr
     130             135                 140

Ile Val Arg Val Glu Ile Leu Arg Asn Phe Tyr Phe Ile Asn Arg Leu
145                 150             155                 160

Thr Gly Tyr Leu Arg Asn
                165
```

INTERFERON β VARIANTS AND CONJUGATES

CROSS-REFERENCE TO RELATED APPLICATIONS

This application claims priority from and benefit of U.S. Provisional Application No. 60/272,116 filed Feb. 27, 2001, U.S. Provisional Application No. 60/343,436 filed Dec. 21, 2001, U.S. Provisional Application No. 60/302,140 filed Jun. 29, 2001, U.S. Provisional Application No. 60/316,170 filed Aug. 30, 2001, and U.S. Provisional Application No. 60/357,945 filed Feb. 19, 2002. Pursuant to 35 U.S.C. §119(a)–(d), this application also claims priority from and benefit of Danish Patent Application No. PA 2001 00333 filed Mar. 1, 2001. This application is also a Continuation-In-Part of U.S. application Ser. No. 09/648,569 filed Aug. 25, 2000, now U.S. Pat. No. 6,531,122, which claims priority from and benefit of U.S. Provisional Application No. 60/160,782 filed Oct. 21, 1999, U.S. Provisional Application No. 60/169,077 filed Dec. 6, 1999, U.S. Provisional Application No. 60/189,599 filed Mar. 15, 2000, U.S. Provisional Application No. 60/202,248 filed May 5, 2000, Danish Patent Application No. PA 1999 01197 filed Aug. 27, 1999, Danish Patent Application No. PA 1999 01691 filed Nov. 26, 1999, Danish Patent Application No. PA 2000 00194 filed Feb. 7, 2000, Danish Patent Application No. PA 2000 00363 filed Mar. 7, 2000 and Danish Patent Application No. PA 2000 00642 filed Apr. 14, 2000. The disclosure of each application listed above is incorporated herein in its entirety for all purposes.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The present invention relates to new interferon β conjugates, methods of preparing such conjugates and the use of such conjugates in therapy, in particular for the treatment of multiple sclerosis. Moreover, the present invention relates to new interferon β (IFNB) molecules, methods of preparing such molecules and the use of such molecules in therapy, in particular for the treatment of multiple sclerosis, viral infections or cancer.

BACKGROUND OF THE INVENTION

Interferons are important cytokines characterized by antiviral, antiproliferative, and immunomodulatory activities. These activities form a basis for the clinical benefits that have been observed in a number of diseases, including hepatitis, various cancers and multiple sclerosis. The interferons are divided into the type I and type II classes. IFNB belongs to the class of type I interferons, which also includes interferons α, τ and ω, whereas interferon γ is the only known member of the distinct type II class.

Human IFNB is a regulatory polypeptide with a molecular weight of 22 kDa consisting of 166 amino acid residues. It can be produced by most cells in the body, in particular fibroblasts, in response to viral infection or exposure to other biologics. It binds to a multimeric cell surface receptor, and productive receptor binding results in a cascade of intracellular events leading to the expression of IFNB inducible genes which in turn produces effects which can be classified as antiviral, antiproliferative and immunomodulatory.

The amino acid sequence of human IFNB was reported by Taniguchi, Gene 10:11–15, 1980, and in EP 83069, EP 41313 and U.S. Pat. No. 4,686,191.

Crystal structures have been reported for human and murine IFNB, respectively (Proc. Natl. Acad. Sci. USA 94:11813–11818, 1997. J. Mol. Biol. 253:187–207, 1995). They have been reviewed in Cell Mol. Life Sci. 54:1203–1206, 1998.

Relatively few protein-engineered variants of IFNB have been reported (WO 9525170, WO 9848018, U.S. Pat. No. 5,545,723, U.S. Pat. No. 4,914,033, EP 260350, U.S. Pat. No. 4,588,585, U.S. Pat. No. 4,769,233, Stewart et al., DNA, Vol. 6, No. 2. 1987, pp. 119–128, Runkel et al., 1998, J. Biol. Chem. 273, No. 14, pp. 8003–8008).

Expression of IFNB in CHO cells has been reported (U.S. Pat. No. 4,966,843, U.S. Pat. No. 5,376,567 and U.S. Pat. No. 5,795,779).

Redlich et al., Proc. Natl. Acad. Sci., USA, Vol. 88. pp. 4040–4044, 1991 disclose immunoreactivity of antibodies against synthetic peptides corresponding to peptide stretches of recombinant human IFNB with the mutation C17S.

IFNB molecules with a particular glycosylation pattern and methods for their preparation have been reported (EP 287075 and EP 529300).

Various references disclose modification of polypeptides by polymer conjugation or glycosylation. Polymer modification of native IFNB or a C17S variant thereof has been reported (EP 229108, U.S. Pat. No. 5,382,657, EP 593868, U.S. Pat. No. 4,917,888 and WO 99/55377). U.S. Pat. No. 4,904,584 discloses PEGylated lysine depleted polypeptides, wherein at least one lysine residue has been deleted or replaced with any other amino acid residue. WO 99/67291 discloses a process for conjugating a protein with PEG, wherein at least one amino acid residue on the protein is deleted and the protein is contacted with PEG under conditions sufficient to achieve conjugation to the protein. WO 99/03887 discloses PEGylated variants of polypeptides belonging to the growth hormone superfamily, wherein a cysteine residue has been susbstituted with a non-essential amino acid residue located in a specified region of the polypeptide. IFNB is mentioned as one example of a polypeptide belonging to the growth hormone superfamily. WO 00/23114 discloses glycosylated and pegylated IFNB. WO 00/23472 discloses IFNB fusion proteins. WO 00/26354 discloses a method of producing a glycosylated polypeptide variant with reduced allergenicity, which as compared to a corresponding parent polypeptide comprises at least one additional glycosylation site. U.S. Pat. No. 5,218,092 discloses modification of granulocyte colony stimulating factor (G-CSF) and other polypeptides so as to introduce at least one additional carbohydrate chain as compared to the native polypeptide. IFNB is mentioned as one example among many polypeptides that allegedly can be modified according to the technology described in U.S. Pat. No. 5,218,092.

Commercial preparations of IFNB are sold under the names Betaseron® (also termed interferon β1b, which is non-glycosylated, produced using recombinant bacterial cells, has a deletion of the N-terminal methionine residue and the C17S mutation), and Avonex™ and Rebif® (also termed interferon β1a, which is glycosylated, produced using recombinant mammalian cells) for treatment of patients with multiple sclerosis, have shown to be effective in reducing the exacerbation rate, and more patients remain exacerbation-free for prolonged periods of time as compared with placebo-treated patients. Furthermore, the accumulation rate of disability is reduced (Neurol. 51:682–689, 1998).

Comparison of interferon β1a and β1b with respect to structure and function has been presented in Pharmaceut. Res. 15:641–649, 1998.

IFNB is the first therapeutic intervention shown to delay the progression of multiple sclerosis, a relapsing then progressive inflammatory degenerative disease of the central nervous system. Its mechanism of action, however, remains largely unclear. It appears that IFNB has inhibitory effects on the proliferation of leukocytes and antigen presentation. Furthermore, IFNB may modulate the profile of cytokine production towards an anti-inflammatory phenotype. Finally, IFNB can reduce T-cell migration by inhibiting the activity of T-cell matrix metalloproteases. These activities are likely to act in concert to account for the mechanism of IFNB in MS (Neurol. 51:682–689, 1998).

In addition, IFNB may be used for the treatment of osteosarcoma, basal cell carcinoma, cervical dysplasia, glioma, acute myeloid leukemia, multiple myeloma, Hodgkin's disease, breast carcinoma, melanoma, and viral infections such as papilloma virus, viral hepatitis, herpes genitalis, herpes zoster, herpetic keratitis, herpes simplex, viral encephalitis, cytomegalovirus pneumonia, and rhinovirus. Various side effects are associated with the use of current preparations of IFNB, including injection site reactions, fever, chills, myalgias, arthralgias, and other flu-like symptoms (Clin. Therapeutics, 19:883–893, 1997).

In addition, 6–40% of patients develop neutralizing antibodies to IFNB (Int. Arch. Allergy Immunol. 118:368–371, 1999). It has been shown that development of IFNB-neutralizing antibodies decreases the biological response to IFNB, and causes a trend towards decreased treatment effect (Neurol. 50:1266–1272, 1998). Neutralizing antibodies will likely also impede the therapeutic utility of IFNB in connection with treatment of other diseases (Immunol. Immuther. 39:263–268, 1994).

Given the magnitude of side effects with current IFNB products, their association with frequent injection, the risk of developing neutralizing antibodies impeding the desired therapeutic effect of IFNB, and the potential for obtaining more optimal therapeutic IFNB levels with concomitant enhanced therapeutic effect, there is clearly a need for improved IFNB-like molecules.

BRIEF DISCLOSURE OF THE INVENTION

This application discloses improved interferon β molecules providing one or more of the aforementioned desired benefits.

In particular conjugates are disclosed that exhibit interferon β activity and comprise at least one non-polypeptide moiety covalently attached to an interferon β polypeptide that comprises an amino acid sequence that differs from that of wildtype human interferon β with the amino acid sequence shown in SEQ ID NO:2 in at least one amino acid residue selected from an introduced or removed amino acid residue comprising an attachment group for the non-polypeptide moiety. Conjugates of the present invention have a number of improved properties as compared to human interferon β, including reduced immunogenicity, increased functional in vivo half-life, increased serum half-life, and/or increased bioavailability. Consequently, the conjugate of the invention offers a number of advantages over the currently available interferon β compounds, including longer duration between injections, fewer side effects, and/or increased efficiency due to reduction in antibodies. Moreover, higher doses of active protein and thus a more effective therapeutic response may be obtained by use of a conjugate of the invention. Furthermore, conjugates of the invention have demonstrated significantly reduced cross-reactivity with sera from patients treated with currently available interferon β products as defined hereinbelow.

In one aspect the invention relates to a conjugate exhibiting interferon β activity and comprising at least one first non-polypeptide moiety covalently attached to an interferon β polypeptide, the amino acid sequence of which differs from that of wild-type human interferon β in at least one introduced and at least one removed amino acid residue comprising an attachment group for said first non-polypeptide moiety.

In another aspect the invention relates to a conjugate exhibiting interferon β activity and comprising at least one first non-polypeptide moiety conjugated to at least one lysine residue of an interferon β polypeptide, the amino acid sequence of which differs from that of wild-type human interferon β in at least one introduced and/or at least one removed lysine residue.

In yet another aspect the invention relates to a conjugate exhibiting interferon β activity and comprising at least one first non-polypeptide moiety conjugated to at least one cysteine residue of an interferon β polypeptide, the amino acid sequence of which differs from at least one introduce cysteine residue into a position that in wild-type human interferon β is occupied by a surface exposed amino acid residue.

In yet another aspect the invention relates to a conjugate exhibiting interferon β activity and comprising at least one first non-polypeptide moiety having an acid group as an attachment group, which moiety is conjugated to at least one aspartic acid or glutamic acid residue of an interferon β polypeptide, the amino acid sequence of which differs from that of wild-type human interferon β in at least one introduced and/or at least one removed aspartic acid or glutamic acid residue.

In yet another aspect the invention relates to a conjugate exhibiting interferon β activity and comprising at least one polymer molecule and at least one sugar moiety covalently attached to an interferon β polypeptide, the amino acid sequence of which differs from that of wild-type human interferon β in a) at least one introduced and/or at least one removed amino acid residue comprising an attachment group for the polymer molecule, and
b) at least one introduced and/or at least one removed amino acid residue comprising an attachment group for the sugar moiety, provided that when the attachment group for the polymer molecule is a cysteine residue, and the sugar moiety is an N-linked sugar moiety, a cysteine residue is not inserted in such a manner that an N-glycosylation site is destroyed.

In yet another aspect the invention relates to a conjugate exhibiting interferon β activity and comprising an interferon β polypeptide, the amino acid sequence of which differs from that of wild-type human interferon β in at least one introduced glycosylation site, the conjugate further comprising at least one un-PEGylated sugar moiety attached to an introduced glycosylation site.

In yet another aspect the invention relates to a conjugate exhibiting interferon activity and comprising an interferon β polypeptide, the amino acid sequence of which differs from that of wild-type human interferon β in that a glycosylation site has been introduced or removed by way of introduction or removal of amino acid residue(s) constituting a part of a glycosylation site in a position that in wildtype human interferon β is occupied by a surface exposed amino acid residue.

In a still further aspect the invention relates to a conjugate exhibiting interferon β activity and comprising a sugar moiety covalently attached to an interferon β polypeptide, the amino acid sequence of which differs from that of wild-type human interferon β in at least one removed glycosylation site.

In a still further aspect the invention relates a glycosylated variant of a parent IFNB polypeptide comprising at least one in vivo glycosylation site, wherein an amino acid residue of said parent polypeptide located close to said glycosylation site has been modified to obtain a variant polypeptide having increased glycosylation as compared to the glycosylation of the parent IFNB polypeptide.

In a further aspect the invention relates to a method of increasing in vivo glycosylation of a parent IFNB molecule that comprises at least one in vivo glycosylation site, which method comprises i) substituting an amino acid residue occupying a first position located close to the in vivo glycosylation site of the parent IFNB molecule with a second amino acid residue to produce a variant IFNB molecule,
ii) measuring the degree of glycosylation of the variant relative to that of the parent IFNB molecule as obtained from expression in a glycosylating host cell under comparable conditions,
iii) if necessary repeating step i) to substitute the second amino acid residue with a third amino acid residue and/or to substitute an amino acid residue located in a second position close to the glycosylation site with a second amino acid residue and repeating step ii) of either the parent molecule or the variant molecule resulting from step i), steps i)–iii) being repeated until an increased in vivo glycosylation is obtained.

In a further aspect the invention relates to an interferon β polypeptide having an amino acid sequence which differs from that of wild-type human interferon β with the amino acid sequence shown in SEQ ID NO:2 and comprising one of the following sets of mutations:

D110F;
C17S+D110F;
C17S+Q49N+Q51T;
C17S+F111N+R113T;
C17S+Q49N+Q51T+F111N+R113T;
D110F+F111N+R113T;
C17S+D110F+F111N+R113T;
C17S+Q49N+Q51T+D110F+F111N+R113T;
C17S+K19R;
C17S+K33R;
C17S+K45R;
C17S+K19R+K33R+K45R; or
C17S+K19R+K33R+K45R+Q49N+Q51T+D110F+F111N+R113T, optionally comprising one or more polymers, eg one or more PEG molecules.

In a specific aspect the invention relates to an interferon β polypeptide having the amino acid sequence:

MSYNLLGFLQ RSSNFQSQKL LWQLNGRLEY CLKDRMNFDI PEEIKQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:56), optionally comprising one or more polymers, eg one or more PEG molecules.

In another specific aspect the invention relates to an interferon β polypeptide having the amino acid sequence:

MSYNLLGFLQ RSSNFQSQRL LWQLNGRLEY CLRDRMNFDI PEEIRQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:57), optionally comprising one or more polymers, eg one or more PEG molecules.

In a further aspect the invention relates to a glycosylated variant of an interferon β polypeptide having an amino acid sequence which differs from that of wild-type human interferon β with the amino acid sequence shown in SEQ ID NO:2 and comprising one of the following sets of mutations:

D110F;
C17S+D110F;
C17S+Q49N+Q51T;
C17S+F111N+R113T;
C17S+Q49N+Q51T+F111N+R113T;
D110F+F111N+R113T;
C17S+D110F+F111N+R113T;
C17S+Q49N+Q51T+D110F+F111N+R113T;
C17S+K19R;
C17S+K33R;
C17S+K45R;
C17S+K19R+K33R+K45R; or
C17S+K19R+K33R+K45R+Q49N+Q51T+D110F+F111N+R113T, optionally comprising one or more polymers, eg one or more PEG molecules.

In a specific aspect the invention relates to a glycosylated variant of an interferon β polypeptide having the amino acid sequence:

MSYNLLGFLQ RSSNFQSQKL LWQLNGRLEY CLKDRMNFDI PEEIKQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:56), optionally comprising one or more polymers, eg one or more PEG molecules.

In another specific aspect the invention relates to a glycosylated variant of an interferon β polypeptide having the amino acid sequence:

MSYNLLGFLQ RSSNFQSQRL LWQLNGRLEY CLRDRMNFDI PEEIRQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:57), optionally comprising one or more polymers, eg one or more PEG molecules.

In still further aspects the invention relates to means and methods for preparing a glycosylated variant IFNB polypeptide of the invention, including nucleotide sequences and expression vectors encoding the polypeptide as well as methods for preparing the polypeptide.

In still further aspects the invention relates to means and methods for preparing a conjugate or interferon β polypeptide for use in the invention, including nucleotide sequences and expression vectors encoding the polypeptide as well as methods for preparing the polypeptide or the conjugate.

In final aspects the invention relates to a therapeutic composition comprising a glycosylated variant IFNB polypeptide of the invention, to a composition of the invention for use in therapy, to the use of a composition in therapy or for the manufacture of a medicament for treatment of diseases.

In final aspects the invention relates to a therapeutic composition comprising a conjugate of the invention, to a conjugate or composition of the invention for use in therapy, to the use of a conjugate or composition in therapy or for the manufacture of a medicament for treatment of diseases.

DETAILED DESCRIPTION OF THE INVENTION

Definitions

Figure 1:
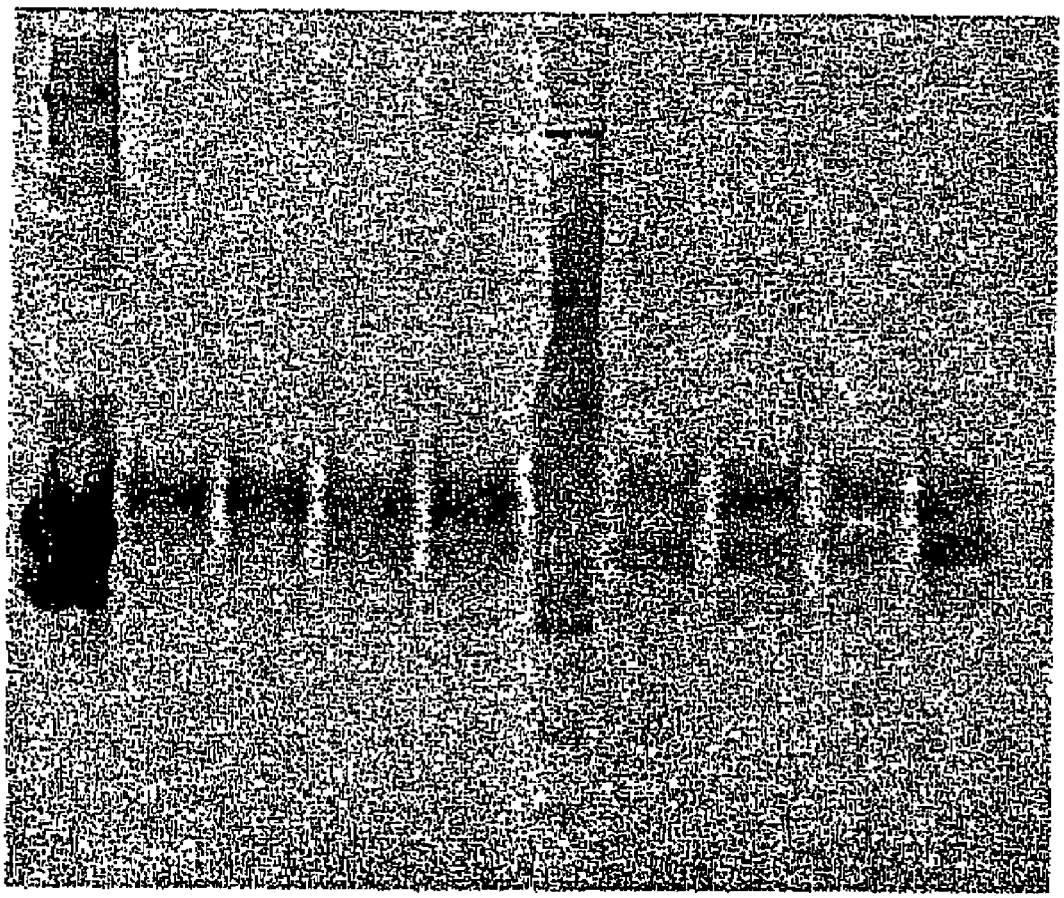
FIG. 1 is a Western blot of optimised glycosylation variants of hIFNB (as described in Examples 17 and 18). Lane 1, wt hIFNB, lane 2, [Q49N, Q51T]hIFNB, lane 3, [Q48F, Q49N, Q51T]hIFNB, lane 4, [Q48V, Q49N, Q51T] hIFNB, lane 5, [Q48W, Q49N, Q51T]hIFNB, lane 6, Marker, lane 7, [F111N, R113T]hIFNB, lane 8, [D110F, F111N, R113T]hIFNB, and lane 9 [D110V, F111N, R113T] hIFNB.

In the context of the present invention the following definitions apply:

The abbreviations "IFNB" or "IFN-β" are used interchangeably with "interferon β".

The term "conjugate" (or interchangeably "conjugated polypeptide") is intended to indicate a heterogeneous (in the sense of composite or chimeric) molecule formed by the covalent attachment of one or more polypeptide(s) to one or more non-polypeptide moieties. The term covalent attachment means that the polypeptide and the non-polypeptide moiety are either directly covalently joined to one another, or else are indirectly covalently joined to one another through an intervening moiety or moieties, such as a bridge, spacer, or linkage moiety or moieties using an attachment group present in the polypeptide. Preferably, the conjugate is soluble at relevant concentrations and conditions, i.e. soluble in physiological fluids such as blood. Examples of conjugated polypeptides of the invention include glycosylated and/or PEGylated polypeptides. The term "non-conjugated polypeptide" may be used about the polypeptide part of the conjugate.

The term "non-polypeptide moiety" is intended to indicate a molecule that is capable of conjugating to an attachment group of a polypeptide of the invention. Preferred examples of such molecule include polymer molecules, sugar moieties, lipophilic compounds, or organic derivatizing agents. When used in the context of a conjugate as described herein it will be understood that the non-polypeptide moiety is linked to the polypeptide part of the conjugate through an attachment group of the polypeptide.

The term "polymer molecule" is defined as a molecule formed by covalent linkage of two or more monomers, wherein none of the monomers is an amino acid residue, except where the polymer is human albumin or another abundant plasma protein. The term "polymer" may be used interchangeably with the term "polymer molecule". The term is intended to cover carbohydrate molecules attached by in vitro glycosylation, i.e. a synthetic glycosylation performed in vitro normally involving covalently linking a carbohydrate molecule to an attachment group of the polypeptide, optionally using a cross-linking agent. Carbohydrate molecules attached by in vivo glycosylation, such as N- or O-glycosylation (as further described below)) are referred to herein as "a sugar moiety". Except where the number of non-polypeptide moieties, such as polymer molecule(s) or sugar moieties in the conjugate is expressly indicated every reference to "a non-polypeptide moiety" contained in a conjugate or otherwise used herein shall be a reference to one or more non-polypeptide moieties, such as polymer molecule(s) or sugar moieties, in the conjugate.

The term "attachment group" is intended to indicate an amino acid residue group of the polypeptide capable of coupling to the relevant non-polypeptide moiety. For instance, for polymer, in particular PEG conjugation a frequently used attachment group is the ε-amino group of lysine or the N-terminal amino group. Other polymer attachment groups include a free carboxylic acid group (e.g. that of the C-terminal amino acid residue or of an aspartic acid or glutamic acid residue), suitably activated carbonyl groups, mercapto groups (e.g. that of cysteine residue), aromatic acid residues (e.g. Phe, Tyr, Trp), hydroxy groups (e.g. that of Ser, Thr or OH-Lys), guanidine (e.g. Arg), Imidazole (e.g. His), and oxidized carbohydrate moieties.

For in vivo N-glycosylation, the term "attachment group" is used in an unconventional way to indicate the amino acid residues constituting an N-glycosylation site (with the sequence N-X'-S/T/C-X", wherein X' is any amino acid residue except proline, X" any amino acid residue that may or may not be identical to X' and preferably is different from proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is an N-linked sugar moiety, the term "amino acid residue comprising an attachment group for the non-polypeptide moiety" as used in connection with alterations of the amino acid sequence of the parent polypeptide is to be understood as amino acid residues constituting an N-glycosylation site is/are to be altered in such a manner that either a functional N-glycosylation site is introduced into the amino acid sequence or removed from said sequence. For an "O-glycosylation site" the attachment group is the OH-group of a serine or threonine residue.

The term "one difference" or "differs from" as used in connection with specific mutations is intended to allow for additional differences being present apart from the specified amino acid difference. For instance, in addition to the removal and/or introduction of amino acid residues comprising an attachment group for the non-polypeptide moiety the IFNB polypeptide may comprise other substitutions that are not related to introduction and/or removal of such amino acid residues. The term "at least one" as used about a non-polypeptide moiety, an amino acid residue, a substitution, etc is intended to mean one or more. The terms "mutation" and "substitution" are used interchangeably herein.

In the present application, amino acid names and atom names (e.g. CA, CS, CD, CG, SG, NZ, N, O, C, etc) are used as defined by the Protein DataBank (PDB) (www website at pdb.org) which are based on the IUPAC nomenclature (IUPAC Nomenclature and Symbolism for Amino Acids and Peptides (residue names, atom names, etc.), Eur. J. Biochem., 138, 9–37 (1984) together with their corrections in Eur. J. Biochem., 152, 1 (1985). CA is sometimes referred to as Cα, CB as Cβ. The term "amino acid residue" is intended to indicate an amino acid residue contained in the group consisting of alanine (Ala or A), cysteine (Cys or C), asparric acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The terminology used for identifying amino acid positions/substitutions is illustrated as follows: C17 (indicates position #17 occupied by a cysteine residue in the amino acid sequence shown in SEQ ID NO:2). C17S (indicates that the cysreine residue of position 17 has been replaced with a serine). The numbering of amino acid residues made herein is made relative to the amino acid sequence shown in SEQ ID NO:2. "M1del" is used about a deletion of the methionine residue occupying position 1. Multiple substitutions are indicated with a "+", e.g. R71N+D73T/S means an amino acid sequence which comprises a substitution of the arginine residue in position 71 with an asparagine and a substitution of the aspartic acid residue in position 73 with a threonine or seine residue, preferably a threonine residue. T/S as used about a given substitution herein means either a T or S residue, preferably a T residue.

The term "nucleotide sequence" is intended to indicate a consecutive stretch of two or more nucleotide molecules. The nucleotide sequence may be of genomic, cDNA, RNA, semisynthetic, synthetic origin, or any combinations thereof.

The term "IFNB protein sequence family" is used in its conventional meaning, i.e. to indicate a group of polypeptides with sufficiently homologous amino acid sequences to allow alignment of the sequences, e.g. using the CLUSTALW program. An IFNB sequence family is available, e.g. from the PFAM families, version 4.0, or may be prepared by use of a suitable computer program such as CLUSTALW version 1.74 using default parameters (Thompson et al., 1994, CLUSTAL W: improving the sensitivity of progressive multiple sequence alignment through sequence weighting, position-specific gap penalties and weight matrix choice, Nucleic Acids Research, 22:4673–4680).

The term "polymerase chain reaction" or "PCR" generally refers to a method for amplification of a desired nucleotide sequence in vitro, as described, for example, in U.S. Pat. No. 4,683,195. In general, the PCR method involves repeated cycles of primer extension synthesis, using oligonucleotide primers capable of hybridising preferentially to a template nucleic acid.

"Cell", "host cell", "cell line" and "cell culture" are used interchangeably herein and all such terms should be understood to include progeny resulting from growth or culturing of a cell. "Transformation" and "transfection" are used interchangeably to refer to the process of introducing DNA into a cell.

"Operably linked" refers to the covalent joining of two or more nucleotide sequences, by means of enzymatic ligation or otherwise, in a configuration relative to one another such that the normal function of the sequences can be performed. For example, the nucleotide sequence encoding a presequence or secretory leader is operably linked to a nucleotide sequence for a polypeptide if it is expressed as a preprotein that participates in the secretion of the polypeptide: a promoter or enhancer is operably linked to a coding sequence if it affects the transcription of the sequence; a ribosome binding site is operably linked to a coding sequence if it is positioned so as to facilitate translation. Generally, "operably linked" means that the nucleotide sequences being linked are contiguous and, in the case of a secretory leader, contiguous and in reading phase. Linking is accomplished by ligation at convenient restriction sites. If such sites do not exist, then synthetic oligonucleotide adaptors or linkers are used, in conjunction with standard recombinant DNA methods.

The term "introduce" is primarily intended to mean substitution of an existing amino acid residue, but may also mean insertion of an additional amino acid residue. The term "remove" is primarily intended to mean substitution of the amino acid residue to be removed by another amino acid residue, but may also mean deletion (without substitution) of the amino acid residue to be removed.

The term "immunogenicity" as used in connection with a given substance is intended to indicate the ability of the substance to induce a response from the immune system. The immune response may be a cell or antibody mediated response (see, e.g., Roitt: Essential Immunology ($8^{th}$ Edition, Blackwell) for further definition of immunogenicity). Immunogenicity may be determined by use of any suitable method known in the art, e.g. in vivo or in vitro, e.g. using the in vitro immunogenicity test outlined in the Materials and Methods section below. The term "reduced immunogenicity" as used about a given polypeptide or conjugate is intended to indicate that the conjugate or polypeptide gives rise to a measurably lower immune response than a reference molecule, such as wildtype human IFNB e.g. Rebif or Avonex, or a variant of wild-type human IFNB such as Betaseron, as determined under comparable conditions. When reference is made herein to commercially available IFNB products (i.e. Betaseron, Avonex and Rebif), it should be understood to mean either the formulated product or the IFNB polypeptide part of the product (as appropriate). Normally, reduced antibody reactivity (e.g. reactivity towards antibodies present in serum from patients treated with commercial IFNB products) is an indication of reduced immunogenicity.

The term "functional in vivo half-life" is used in its normal meaning, i.e. the time at which 50% of a given functionality of the polypeptide or conjugate is retained (such as the time at which 50% of the biological activity of the polypeptide or conjugate is still present in the body/target organ, or the time at which the activity of the polypeptide or conjugate is 50% of the initial value). As an alternative to determining functional in vivo half-life, "serum half-life" may be determined, i.e. the time in which 50% of the polypeptide or conjugate molecules circulate in the plasma or bloodstream prior to being cleared. Determination of serum half-life is often more simple than determining functional in vivo half-life and the magnitude of serum half-life is usually a good indication of the magnitude of functional in vivo half-life. Alternative terms to serum half-life include "plasma half-life", "circulating half-life", "serum clearance", "plasma clearance" and "clearance half-life". The functionality to be retained is normally selected from antiviral, antiproliferative, immunomodulatory or receptor binding activity. Functional in vivo half-life and serum half-life may be determined by any suitable method known in the art as further discussed in the Materials and Methods section hereinafter.

The polypeptide or conjugate is normally cleared by the action of one or more of the reticuloendothelial systems (RES), kidney, spleen or liver, or by specific or unspecific proteolysis. Clearance taking place by the kidneys may also be referred to as "renal clearance" and is e.g. accomplished by glomerular filtration, tubular excretion or tubular elimination. Normally, clearance depends on physical characteristics of the polypeptide or conjugate, including molecular weight, size (diameter) (relative to the cut-off for glomerular filtration), charge, symmetry, shape/rigidity, attached carbohydrate chains, and the presence of cellular receptors for the protein. A molecular weight of about 67 kDa is considered to be an important cut-off-value for renal clearance.

Reduced renal clearance may be established by any suitable assay, e.g. an established in vivo assay. Typically, the renal clearance is determined by administering a labelled (e.g. radiolabelled or fluorescence labelled) polypeptide or polypeptide conjugate to a patient and measuring the label activity in urine collected from the patient. Reduced renal clearance is determined relative to the corresponding non-conjugated polypeptide or the non-conjugated corresponding wild-type polypeptide or a commercial IFNB product under comparable conditions.

The term "increased" as used about the functional in vivo half-life or serum half-life is used to indicate that the relevant half-life of the conjugate or polypeptide is statistically significantly increased relative to that of a reference molecule, such as an un-conjugated wildtype human IFNB (e.g. Avonex or Rebif) or an unconjugated variant human IFNB (e.g. Betaseron) as determined under comparable conditions.

The term "reduced immunogenicity and/or increased functional in vivo half-life and/or increased serum half-life" is to be understood as covering any one, two or all of these properties. Preferably, a conjugate or polypeptide as described herein has at least two of these properties, i.e. reduced immunogenicity and increased functional in vivo half-life, reduced immunogenicity and increased serum half-life or increased functional in vivo half-life and increased serum half-life. Most preferably, the conjugate or polypeptide has all properties.

The term "under comparable conditions" as used about measuring of relative (rather than absolute) properties of a molecule of the invention and a reference molecule is intended to indicate that the relevant property of the two molecules is assayed using the same assay (i.e. the assay is performed under the same conditions including the same internal standard), and, when relevant, the same type of animals.

The term "exhibiting IFNB activity" is intended to indicate that the polypeptide or conjugate has one or more of the functions of native IFNB, in particular human wildtype IFNB with the amino acid sequence shown in SEQ ID NO:2 (which is the mature sequence) optionally expressed in a glycosylating host cell or any of the commercially available IFNB products. Such functions include capability to bind to an interferon receptor that is capable of binding IFNB and initiating intracellular signalling from the receptor, in particular a type I interferon receptor constituted by the receptor subunits IFNAR-2 and IFNAR-1 (Domanski et al., The Journal of Biological Chemistry, Vol. 273, No. 6, pp 3144–3147, 1998, Mogensen et al., Journal of Interferon and Cytokine Research, 19: 1069–1098, 1999), and antiviral, antiproliferative or immunomodulatory activity (which can be determined using assays known in the art (e.g. those cited in the following disclosure)). IFNB activity may be assayed by methods known in the art as exemplified in the Materials and Methods section hereinafter.

The polypeptide or conjugate "exhibiting" or "having" IFNB activity is considered to have such activity, when it displays a measurable function, e.g. a measurable receptor binding and stimulating activity (e.g. as determined by the primary or secondary assay described in the Materials and Methods section). The polypeptide exhibiting IFNB activity may also be termed "IFNB molecule", IFNB variant polypeptide" or "IFNB polypeptide" herein. The terms "IFNB polypeptide", "IFNB variant" and "variant polypeptide" are primarily used herein about modified polypeptides of the invention.

The term "parent IFNB" is intended to indicate the starting molecule to be improved in accordance with the present invention and/or as described in co-pending U.S. application Ser. No. 09/648,569. Preferably, the parent IFNB belongs to the IFNB sequence family. While the parent IFNB may be of any origin, such as vertebrate or mammalian or primate origin (e.g. any of the origins defined in WO 00/23472), the parent IFNB is preferably wild-type human IFNB with the amino acid sequence shown in SEQ ID NO:2 or a variant thereof. In the context of a parent IFNB polypeptide, a "variant" is a polypeptide, which differs in one or more amino acid residues from a parent polypeptide, normally in 1, 2,3, 4, 5, 6, 7, 8, 9, 10, 11, 12, 13, 14 or 15 amino acid residues. Examples of wild-type human IFNB include the polypeptide part of Avonex or Rebif. An example of a parent IFNB variant is Betaseron. Alternatively, the parent IFNB polypeptide may comprise an amino acid sequence, which is a hybrid molecule between IFNB and another homologous polypeptide, such as interferon α, interferon τ, or interferon ω, optionally containing one or more additional substitutions introduced into the hybrid molecule. Such a hybrid molecule may contain an amino acid sequence, which differs in more than 10 amino acid residues from the amino acid sequence shown in SEQ ID NO:2. In order to be useful as a parent polypeptide the hybrid molecule exhibits IFNB activity (e.g. as determined in the secondary assay described in the Materials and Methods section herein). Other examples of variants of wild-type human IFNB that may serve as parent IFNB molecules in the present invention include, for example: polypeptides described in U.S. Ser. No. 09/648,569 having introduced and/or removed amino acid residues comprising an attachment group for a non-polypeptide moiety, and any IFNB molecule described in WO 00/23114, WO 00/23472, WO 99/3887. Any wild-type IFNB or variant thereof available in the art may serve as a parent IFNB molecule in the present invention.

The term "functional site" as pertaining to a polypeptide or conjugate of the invention is intended to indicate one or more amino acid residues which is/are essential for or otherwise involved in the function or performance of IFNB, and thus "located at" the functional site. The functional site is e.g. a receptor binding site and may be determined by methods known in the art, preferably by analysis of a structure of the polypeptide complexed to a relevant receptor, such as the type I interferon receptor constituted by IFNAR-1 and IFNAR-2.

Polypeptide Variants of the Invention

Variants with Increased Glycosylation

It has surprisingly been found that glycosylation at a given glycosylation site of an IFNB molecule may be increased by modifying one or more amino acid residues located close to said glycosylation site, whether it is an introduced site or a naturally-occurring site.

Accordingly, in one aspect the present invention relates to a glycosylated variant of a parent IFNB polypeptide comprising at least one in vivo glycosylation site, wherein an amino acid residue of said parent polypeptide located close to said glycosylation site has been modified to obtain a variant polypeptide having an increased glycosylation as compared to the glycosylation of the parent polypeptide.

The term "variant" is used to denote that amino acid residues of the parent polypeptide have been changed. The glycosylated variant may also be termed an IFNB conjugate (comprising a non-polypeptide moiety being a sugar moiety attached to the polypeptide part of the conjugate).

Normally, the in vivo glycosylation site is an N-glycosylation site, but also an O-glycosylation site is contemplated as relevant for the present invention.

In the present context the term "increased glycosylation" is intended to indicate increased levels of attached carbohydrate molecules, normally obtained as a consequence of increased (or better) utilization of glycosylation site(s). The increased glycosylation may be determined by any suitable method known in the art for analyzing attached carbohydrate structures. One convenient assay for determining attached carbohydrate structures is the method described in Example 17 and 18 hereinafter.

An amino acid residue "located close to" a glycosylation site is usually located in position −4, −3, −2, −1, +1, +2, +3 or +4 relative to the amino acid residue of the glycosylation site to which the carbohydrate is attached, in particular in position −2, −1, +1, or +2, such as position −1 or +1. Thus, the amino acid residue located close to an N-glycosylation site (having the sequence N-X'-S/T/C-X") may be located in position −4, −3, −2, −1 relative to the N-residue, at position X' or X" (in which case the amino acid residue to be introduced is preferably different from proline), or at position +1 relative to the X" residue.

The amino acid modification is normally a substitution, the substitution being made with any other amino acid residue that gives rise to an increased glycosylation of the IFNB variant as compared to that of the parent IFNB polypeptide. Such other amino acid residue may be determined by trial and error type of experiments (i.e. by substitution of the amino acid residue of the relevant position to any other amino acid residue, and determination of the resulting glycosylation of the resulting variant).

In principle the parent IFNB polypeptide to be modified in accordance with the present invention may be any polypeptide exhibiting IFNB activity and having at least one glycosylation site, in particular an N-glycosylation site. Suitable parent polypeptides are given in the section hereinabove entitled "Definitions" and may include a wildtype IFNB e.g. wt human IFNB, or a non-naturally occurring IFNB polypeptide, e.g. a variant or fragment of wt human IFNB.

The parent IFNB polypeptide may comprise more than one glycosylation site, e.g. 2–10, such as 2–7 or 2–5 glycosylation sites. The glycosylation site may be a naturally-occurring glycosylation site or an introduced glycosylation site, preferably an N-glycosylation site. The N-glycosylation site defined by N80 and T82 of wildtype human IFNB is an example of a naturally occurring glycosylation site.

When the parent IFNB polypeptide comprises at least one introduced N-glycosylation site, said site is preferably located in a position which is equivalent to or being any of those described in the section entitled "Conjugate of the invention" or "Conjugate of the invention wherein the non-polypeptide moiety is a sugar moiety".

An "equivalent position" is intended to indicate a position in the amino acid sequence of a given IFNB polypeptide, which is homologous (i.e. corresponding in position in either primary or tertiary structure) to the relevant position in the amino acid sequence shown in SEQ ID NO:2. The "equivalent position" is conveniently determined on the basis of an alignment of members of the IFNB protein sequence family, e.g. using the program CLUSTALW version 1.74 using default parameters (Thompson et al., 1994, CLUSTAL W: improving the sensitivity of progressive multiple sequence alignment through sequence weighting, position-specific gap penalties and weight matrix choice, Nucleic Acids Research, 22:4673–4680) or from published alignments.

In a specific embodiment, the parent IFNB polypeptide is wt human IFNB comprising one or more introduced glycosylation sites, which site(s) is/are introduced by means of substitution(s) as defined in the section entitled "Conjugate of the invention wherein the non-polypeptide moiety is a sugar moiety". When the parent IFNB polypeptide is derived from wt human IFNB it normally also comprises naturally-occurring glycosylation site at position N80.

For instance, the parent IFNB polypeptide comprises an introduced glycosylation site in a position equivalent to at least one of the following positions 2, 49, 51 or 111 of the amino acid sequence of wt human IFNB with the amino acid sequence shown in SEQ ID NO:2 (as defined by the amino acid substitutions S2N+N4T/S, Q49N+Q51T/S, Q51N+E53T/S or F111N+R113T/S, respectively) and/or comprises a glycosylation site in a corresponding position of that of the wt human IFNB sequence defined by N80+T82. The variant according to the invention prepared from such parent IFNB polypeptide further comprises an amino acid substitution in a position located close to the N-glycosylation site, e.g. in a position corresponding to or being position 1, 48, 50, 79 or 110 of SEQ ID NO:2, the substitution being with an amino acid residue which is different from that occupying the relevant position in the parent polypeptide and capable of giving rise to an increased glycosylation at the relevant glycosylation site as compared to the parent IFNB polypeptide.

More specifically, in accordance with one embodiment of the present invention the variant is prepared from a parent IFNB polypeptide comprising an introduced glycosylation site defined by a substitution equivalent to or being Q49N+Q51T/S of SEQ ID NO:2, the variant further comprising a substitution of the amino acid residue located in an equivalent position to or being K45, Q46, L47, Q48, F50, or K52 of SEQ ID NO:2, the substitution being made to an amino acid residue which gives rise to increased glycosylation at said introduced glycosylation site as compared to that of the parent IFNB polypeptide. Preferably, the amino acid residue to be substituted is located in a position equivalent to or being Q48.

In another embodiment the variant is prepared from a parent IFNB polypeptide comprising an introduced glycosylation site defined by a substitution equivalent to or being F111N+R113T/S of SEQ ID NO:2, the variant further comprising a substitution of the amino acid residue located in an equivalent position to or being E107, K108, E109, D110, T112, or G114 of SEQ ID NO:2, the substitution being made to an amino acid residue which gives rise to increased glycosylation at said introduced glycosylation site as compared to that of the parent IFNB polypeptide. Preferably, the amino acid residue to be substituted is located in a position equivalent to or being D110.

In yet another embodiment the variant is prepared from a parent IFNB polypeptide comprising an introduced glycosylation site defined by a substitution equivalent to or being Q51N+E53T/S of SEQ ID NO:2, the variant further comprising a substitution of the amino acid residue located in an equivalent position to or being L47, Q48, Q49, F50, K52, or D54 of SEQ ID NO:2, the substitution being made to an amino acid residue which gives rise to increased glycosylation at said introduced glycosylation site as compared to that of the parent IFNB polypeptide. Preferably, the amino acid residue to be substituted is located in a position equivalent to or being Q49.

In yet another embodiment the variant is prepared from a parent IFNB polypeptide comprising an introduced glycosylation site defined by a substitution equivalent to or being S2N+N4T/S of SEQ ID NO:2, the variant further comprising a substitution of the amino acid residue located in an equivalent position to or being M1, Y3 or L5 of SEQ ID NO:2, the substitution being made to an amino acid residue which gives rise to increased glycosylation at said introduced glycosylation site as compared to that of the parent IFNB polypeptide. Preferably, the amino acid residue to be substituted is located in a position equivalent to or being M1. By use of the www website at cbs.dtu.dk/services/SignalP/, it has been verified that all amino acid substitutions are allowed in position 1 of SEQ ID NO:2 (i.e. allows for correct signal peptide cleavage).

In yet another embodiment the variant is prepared from a parent IFNB polypeptide comprising a naturally occurring glycosylation site located in a position equivalent to or being N80 and T82 of SEQ ID NO:2, the variant further comprising a substitution of the amino acid residue located in an equivalent position to or being S76, T77, E78, W79, E81 or I83 of SEQ ID NO:2, the substitution being made to an amino acid residue which gives rise to increased glycosylation at said introduced glycosylation site as compared to that of the parent IFNB polypeptide. Preferably, the amino acid residue to be substituted is located in a position equivalent to or being W79.

For instance, the variant according to this aspect comprises at least one of the following sets of mutations:
Q48F,V,W,Y+Q49N+Q51T/S;
D110F,V,Y+F111N+R113T/S all mutations being indicated relative to the amino acid sequence shown in SEQ ID NO:2.

It will be understood that glycosylation from glycosylation sites introduced in other positions than those specifically mentioned above (e.g. in a position occupied by any surface exposed amino acid residue as defined herein and/or in U.S. Ser. No. 09/648,569) may be modified analogously to what has been described above.

Furthermore, it is presently preferred that the parent IFNB polypeptide to be modified according to this aspect is free from a free cysteine residue, e.g. from the cysteine residue located in position 17 of SEQ ID NO:2. Preferably, when the parent polypeptide is derived from wt human IFNB the parent comprises a non-cysteine amino acid residue in position 17, e.g. the mutation C17S, relative to the amino acid sequence shown in SEQ ID NO:2.

In yet another embodiment the parent IFNB polypeptide to be modified in accordance with this aspect comprises at least one introduced and/or removed amino acid residue comprising an attachment group for a second non-polypeptide moiety. For instance, the introduced and/or removed amino acid residue is as described in the section entitled "Conjugate of the invention", "Conjugate of the invention wherein the non-polypeptide moiety is a molecule that has lysine as an attachment group", "Conjugate of the invention wherein the non-polypeptide moiety binds to a cysteine residue", or "Conjugate of the invention wherein the non-polypeptide moiety binds to an acid group", and thus the parent IFNB polypeptide is the polypeptide part of a conjugate as described in any of these sections.

The amino acid residue comprising an attachment group for a non-polypeptide moiety is, e.g., a lysine residue. In a specific embodiment the parent IFNB polypeptide comprises at least one substitution of an amino acid residue located in an equivalent position to or being K19, K33, K45 and K123, the lysine residue preferably being substituted with an R residue.

More specifically, the parent IFNB polypeptide may comprise one of the following sets of mutations (indicated relative to SEQ ID NO:2):
C17S+Q49N+Q51T+F111N+R113T;
S2N+N4T+C17S+Q51N+E53T;
C17S+K19R+K45R+Q49N+Q51T+F111N+R113T+ K123R;
C17S+K19R+K33R+K45R+Q49N+Q51T+F111N+ R113T+K123R;
S2N+N4T+C17S+K19R+K45R+Q51N+E53T+K123R;
S2N+N4T+C17S+K19R+K33R+K45R+Q51N+E53T+ K123R;
S2N+N4T+C17S+K19R+K45R+Q51N+E53T+F111N+ R113T+K123R; or
S2N+N4T+C17S+K19R+K33R+K45R+Q51N+E53T+ F111N+R113T+K123R.

When the parent IFNB polypeptide comprises the mutation Q49N+Q51T/S, the variant according to this aspect preferably further comprises the substitution Q48F,V,W,Y. When the parent IFNB polypeptide comprises the mutations F111N+R113T/S, the variant preferably further comprises the substitution D110F,V,Y.

It will be understood that when the parent IFNB polypeptide and thus the variant comprises an introduced and/or removed amino acid residue comprising an attachment group for a second non-polypeptide moiety, the variant is preferably not only glycosylated, but also conjugated to the second non-polypeptide moiety via at least one introduced and/or removed attachment group. The second non-polypeptide moiety is usually different from a sugar moiety, and is normally a polymer, such as PEG. The section entitled "Non-polypeptide moiety of a conjugate of the invention" describes suitable polymers and other types of non-polypeptide moieties which can be used as second non-polypeptide moieties for conjugation of the variants according to this aspect.

In a further aspect the invention relates to an interferon β polypeptide having an amino acid sequence which differs from that of wild-type human interferon β with the amino acid sequence shown in SEQ ID NO:2 and comprising one of the following sets of mutations:
D110F;
C17S+D110F;
C17S+Q49N+Q51T;
C17S+F111N+R113T;
C17S+Q49N+Q51T+F111N+R113T;

D110F+F111N+R113T;
C17S+D110F+F111N+R113T;
C17S+Q49N+Q51T+D110F+F111N+R113T;
C17S+K19R;
C17S+K33R;
C17S+K45R;
C17S+K19R+K33R+K45R; or
C17S+K19R+K33R+K45R+Q49N+Q51T+D110F+F111N+R113T, optionally comprising one or more polymers, eg one or more PEG molecules. Each of these sets of mutations is considered an individual embodiment, and may be the subject of a claim.

In a specific aspect the invention relates to an interferon β polypeptide having the amino acid sequence:
MSYNLLGFLQ RSSNFQSQKL LWQLNGRLEY CLKDRMNFDI PEEIKQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:56), optionally comprising one or more polymers, eg one or more PEG molecules.

In another specific aspect the invention relates to an interferon β polypeptide having the amino acid sequence:
MSYNLLGFLQ RSSNFQSQRL LWQLNGRLEY CLRDRMNFDI PEEIRQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:57), optionally comprising one or more polymers, eg one or more PEG molecules.

In a further embodiment the interferon β polypeptide further comprises a PEG molecule, in particular a 12 kDa or 20 kDa PEG, eg. mono-PEG 20 kDa. When the interferon beta molecule is PEGylated it usually comprises 1–5 polyethylene glycol (PEG) molecules. In a further embodiment the interferon molecule comprises 1–5 PEG molecules, such as 1, 2 or 3 PEG molecules. In a further embodiment each PEG molecule has a molecular weight of about 5 kDa (kilo Dalton) to 100 kDa. In a further embodiment each PEG molecule has a molecular weight of about 10 kDa to 40 kDa. In a further embodiment each PEG molecule has a molecular weight of about 12 kDa. In a further embodiment each PEG molecule has a molecular weight of about 20 kDa. Preferably the interferon molecule comprises 1–3 PEG molecules each having a molecular weight of about 12 kDa, or 1 PEG molecule having a molecular weight of about 20 kDa. Suitable PEG molecules are available from Shearwater Polymers, Inc. and Enzon, Inc. and may be selected from SS-PEG, NPC-PEG, aldehyd-PEG, mPEG-SPA, mPEG-SCM, mPEG-BTC, SC-PEG, tresylated mPEG (U.S. Pat. No. 5,880,255), or oxycarbonyl-oxy-N-dicarboxyimide-PEG (U.S. Pat. No. 5,122,614).

In a still further aspect the invention relates to a method of increasing in vivo glycosylation of a parent IFNB polypeptide that comprises at least one in vivo glycosylation site, which method comprises i) substituting an amino acid residue occupying a first position located close to the in vivo glycosylation site of the parent IFNB polypeptide with a second amino acid residue to produce a variant IFNB polypeptide, ii) measuring the degree of glycosylation of the variant relative to that of the parent IFNB polypeptide as obtained from expression in a glycosylating host cell, under comparable conditions, iii) if necessary repeating step i) to substitute the second amino acid residue with a third amino acid residue and/or to substitute an amino acid residue located in a second position close to the glycosylation site with a second amino acid residue and repeating step ii) of either the parent polypeptide or the variant polypeptide resulting from step i), steps i)–iii) being repeated until an increased in vivo glycosylation is obtained.

The parent polypeptide may comprise a naturally-occurring or a non-naturally occurring glycosylation site, and is e.g. a parent polypeptides as defined herein above. The amino acid residue located close to a glycosylation site is, e.g., any of those identified in the present section.

In a further aspect the invention relates to a glycosylated variant of an interferon β polypeptide having an amino acid sequence which differs from that of wild-type human interferon β with the amino acid sequence shown in SEQ ID NO:2 and comprising one of the following sets of mutations:
D110F;
C17S+D110F;
C17S+Q49N+Q51T;
C17S+F111N+R113T;
C17S+Q49N+Q51T+F111N+R113T;
D110F+F111N+R113T;
C17S+D110F+F111N+R113T;
C17S+Q49N+Q51T+D110F+F111N+R113T;
C17S+K19R;
C17S+K33R;
C17S+K45R;
C17S+K19R+K33R+K45R; or
C17S+K19R+K33R+K45R+Q49N+Q51T+D110F+F111N+R113T, optionally comprising one or more polymers, eg one or more PEG molecules. Each of these sets of mutations is considered an individual embodiment, and may be the subject of a claim.

In a specific aspect the invention relates to a glycosylated variant of an interferon β polypeptide having the amino acid sequence:
MSYNLLGFLQ RSSNFQSQKL LWQLNGRLEY CLKDRMNFDI PEEIKQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:56), optionally comprising one or more polymers, eg one or more PEG molecules.

In another specific aspect the invention relates to a glycosylated variant of an interferon β polypeptide having the amino acid sequence:
MSYNLLGFLQ RSSNFQSQRL LWQLNGRLEY CLRDRMNFDI PEEIRQLQNF TKEDAALTIY EMLQNIFAIF RQDSSSTGWN ETIVENLLAN VYHQINHLKT VLEEKLEKEF NTTGKLMSSL HLKRYYGRIL HYLKAKEYSH CAWTIVRVEI LRNFYFINRL TGYLRN (SEQ ID NO:57), optionally comprising one or more polymers, eg one or more PEG molecules.

In one embodiment, the interferon molecule is glycosylated and PEGylated. In a further embodiment, the interferon molecule is glycosylated.

In a further embodiment the glycosylated interferon β polypeptide comprises one to five sugar moieties, such as one to three sugar moieties. When the interferon molecule is glycosylated it is preferably N-glycosylated. When the interferon molecule is glycosylated it usually comprises 1–5 sugar moieties, such as 1–3 sugar moieties. In a further embodiment, the interferon molecule is N-glycosylated, and comprises 1–5 sugar moieties, such as 1–3 sugar moieties. In a further embodiment, the interferon molecule is N-glycosylated, and comprises 3 sugar moieties. According to the specific aspects above, the interferon β polypeptide has three sugar moieties, that are in positions N49, N80, and N111.

In a further embodiment the glycosylated interferon β polypeptide further comprises a PEG molecule, in particular a 12 kDa or 20 kDa PEG, eg. mono-PEG 20 kDa. When the interferon molecule is PEGylated it usually comprises 1–5 polyethylene glycol (PEG) molecules. In a further embodiment the interferon molecule comprises 1–5 PEG molecules, such as 1, 2 or 3 PEG molecules. In a further embodiment each PEG molecule has a molecular weight of about 5 kDa (kilo Dalton) to 100 kDa. In a further embodiment each PEG molecule has a molecular weight of about 10 kDa to 40 kDa. In a further embodiment each PEG molecule has a molecular weight of about 12 kDa. In a further embodiment each PEG molecule has a molecular weight of about 20 kDa. Preferably the interferon molecule comprises 1–3 PEG molecules each having a molecular weight of about 12 kDa, or 1 PEG molecule having a molecular weight of about 20 kDa. According to the specific aspects above, in a particular embodiment, the interferon β polypeptide contains 1–3 12 kDa PEG molecules. According to the specific aspects above, in a particular embodiment, the interferon β polypeptide contains one 20 kDa PEG molecule. Suitable PEG molecules are available from Shearwater Polymers, Inc. and Enzon, Inc. and may be selected from SS-PEG, NPC-PEG, aldehyd-PEG, mPEG-SPA, mPEG-SCM, mPEG-BTC, SC-PEG, tresylated mPEG (U.S. Pat. No. 5,880,255), or oxy-carbonyl-oxy-N-dicarboxyimide-PEG (U.S. Pat. No. 5,122,614).

The glycosylated variants according to this aspect are expressed recombinantly in a glycosylating host cell, preferably a mammalian host cell such as any of those mentioned in the section entitled "Coupling to a sugar moiety".

Preferably, the variant according to this aspect has retained most or all of the IFNB expression level (IU/ml) of the parent IFNB polypeptide. However, when the increase in glycosylation obtained by substitution of an amino acid residue located close to a glycosylation site is very high a decrease in expression level may be acceptable as long as the overall performance of the variant is improved as compared to that of the parent IFNB polypeptide.

It will be understood that the variants according to this aspect normally has any of the improved properties that are described for conjugates according to U.S. Ser. No. 09/648, 569, e.g. any of the improved properties described further above in the section entitled “Conjugate of the invention”.

Variants with Specific Amino Acid Substitutions

In a further embodiment of the present invention the variant is one which comprises the mutation L98P relative to a parent IFNB molecule, in particular wild-type human IFNB with the amino acid sequence shown in SEQ ID NO:2. The variant may comprise L98P as the only mutation, or may comprise additional mutations, e.g. any of the mutations described in any of the sections herein, the title of which starts with “Conjugate of the invention . . . ” or the section entitled “Variants with increased glycosylation”. For instance the variant may comprise the following mutations:

Q49N+Q51T+L98P+F111N+R113T
C17S+Q49N+Q51T+L98P+F111N+R113T

Further specific glycosylated variants of the invention include the following amino acid substitutions (relative to SEQ ID NO:2):

C17S+Q49N+Q51T+F111N+R113T
S2N+N4T+C17S+Q51N+E53T
S2N+N4T+C17S+Q51N+E53T+F111N+R113T

Further specific glycosylated variants of the invention include the following amino acid substitutions (relative to SEQ ID NO:2):

S2N+N4T+C17S+K19R+Q51N+E53T+K123R
S2N+N4T+C17S+K19R+Q51N+E53T+F111N+R113T+K123R
S2N+N4T+C17S+K19R+K45R+Q51N+E53T+F111N+R113T+K123R

These variants are typically conjugated to a second non-polypeptide moiety, such as a polymer, e.g. PEG.

It will be understood that the variants according to this aspect normally have any of the improved properties that are described for conjugates according to U.S. Ser. No. 09/648, 569, e.g. any of the improved properties described further above in the section entitled “Conjugate of the invention”.

Variants which are Fusion Proteins

In a further aspect the invention relates to a variant IFNB polypeptide which is a fusion protein comprising a) an IFNB polypeptide and b) a human serum albumin polypeptide (HSA). The variant IFNB polypeptide is, e.g., the polypeptide part of a conjugate as described in herein and/or in U.S. Ser. No. 09/648,569 or a glycosylated variant according to the present invention.

The HSA is, e.g., wt human serum albumin or a fragment or variant thereof, e.g. any of the human serum albumin fragments disclosed in WO 97/24445. Fusion to human serum albumin is also described in WO 93/15199, WO 93/15200 and EP 413 622.

The IFNB polypeptide and the human serum albumin part of the fusion protein may be directly linked or linked via a linker peptide, e.g. as disclosed in WO 97/24445. HSA may be linked to the C-terminal end of the IFNB polypeptide or to the N-terminal end, optionally via a linker peptide. It is contemplated that fusion of an IFNB polypeptide to human serum albumin or a variant or fragment thereof results in an overall increased stability of the resulting fusion protein.

It will be understood that a variant according to this aspect normally has any of the improved properties that are described for conjugates according to U.S. Ser. No. 09/648, 569, e.g. any of the improved properties described further above in the section entitled “Conjugate of the invention”.

Conjugate of the Invention

A first aspect of the invention relates to a conjugate exhibiting IFNB activity and comprising at least one first non-polypeptide moiety covalently attached to an IFNB polypeptide, the amino acid sequence of which differs from that of wildtype human IFNB in at least one introduced and at least one removed amino acid residue comprising an attachment group for said first non-polypeptide moiety.

By removing and/or introducing amino acid residues comprising an attachment group for the non-polypeptide moiety it is possible to specifically adapt the polypeptide so as to make the molecule more susceptible to conjugation to the non-polypeptide moiety of choice, to optimize the conjugation pattern (e.g. to ensure an optimal distribution of non-polypeptide moieties on the surface of the IFNB molecule and thereby, e.g., effectively shield epitopes and other surface parts of the polypeptide without significantly impairing the function thereof). For instance, by introduction of attachment groups, the IFNB polypeptide is boosted or otherwise altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g. to an amino acid residue located at or near a functional site of the polypeptide (since conjugation at such a site may result in inactivation or reduced IFNB activity of the resulting conjugate due to impaired receptor recognition). Further, it may be advantageous to remove an attachment group located closely to another attachment group in order to avoid heterogeneous conjugation to such groups.

It will be understood that the amino acid residue comprising an attachment group for a non-polypeptide moiety, either it be removed or introduced, is selected on the basis of the nature of the non-polypeptide moiety and, in most instances, on the basis of the conjugation method to be used. For instance, when the non-polypeptide moiety is a polymer molecule, such as a polyethylene glycol or polyalkylene oxide derived molecule, amino acid residues capable of functioning as an attachment group may be selected from the group consisting of lysine, cysteine, aspartic acid, glutamic acid and arginine. When the non-polypeptide moiety is a sugar moiety the attachment group is an in vivo glycosylation site, preferably an N-glycosylation site.

Whenever an attachment group for a non-polypeptide moiety is to be introduced into or removed from the IFNB polypeptide in accordance with the invention, the position of the IFNB polypeptide to be modified is conveniently selected as follows:

The position is preferably located at the surface of the IFNB polypeptide, and more preferably occupied by an amino acid residue that has more than 25% of its side chain exposed to the solvent, preferably more than 50% of its side chain exposed to the solvent. Such positions have been identified on the basis of an analysis of a 3D structure of the human IFNB molecule as described in the Methods section herein.

Alternatively or additionally, the position to be modified is identified on the basis of an analysis of an IFNB protein sequence family. More specifically, the position to be modified can be one, which in one or more members of the family other than the parent IFNB, is occupied by an amino acid residue comprising the relevant attachment group (when such amino acid residue is to be introduced) or which in the parent IFNB, but not in one or more other members of the family, is occupied by an amino acid residue comprising the relevant attachment group (when such amino acid residue is to be removed).

In order to determine an optimal distribution of attachment groups, the distance between amino acid residues located at the surface of the IFNB molecule is calculated on the basis of a 3D structure of the IFNB polypeptide. More specifically, the distance between the CB's of the amino acid residues comprising such attachment groups, or the distance between the functional group (NZ for lysine, CG for aspartic acid, CD for glutamic acid, SG for cysteine) of one and the CB of another amino acid residue comprising an attachment group are determined. In case of glycine, CA is used instead of CB. In the IFNB polypeptide part of a conjugate of the invention, any of said distances is preferably more than 8 Å, in particular more than 10 Å in order to avoid or reduce heterogeneous conjugation.

Furthermore, in the IFNB polypeptide part of a conjugate of the invention attachment groups located at the receptor-binding site of IFNB has preferably been removed, preferably by substitution of the amino acid residue comprising such group.

A still further generally applicable approach for modifying an IFNB polypeptide is to shield, and thereby destroy or otherwise inactivate an epitope present in the parent IFNB, by conjugation to a non-polypeptide moiety. Epitopes of human IFNB may be identified by use of methods known in the art, also known as epitope mapping, see, e.g. Romagnoli et al., J. Biol Chem, 1999, 380(5):553–9, DeLisser H M, Methods Mol Biol, 1999, 96:11–20, Van de Water et al., Clin Immunol Immunopathol, 1997, 85(3):229–35, Saint-Remy J M, Toxicology, 1997, 119(1):77–81, and Lane D P and Stephen C W, Curr Opin Immunol, 1993, 5(2):268–71. One method is to establish a phage display library expressing random oligopeptides of e.g. 9 amino acid residues. IgG1 antibodies from specific antisera towards human IFNB are purified by immunoprecipitation and the reactive phages are identified by immunoblotting. By sequencing the DNA of the purified reactive phages, the sequence of the oligopeptide can be determined followed by localization of the sequence on the 3D-structure of the IFNB. Alternatively, epitopes can be identified according to the method described in U.S. Pat. No. 5,041,376. The thereby identified region on the structure constitutes an epitope that then can be selected as a target region for introduction of an attachment group for the non-polypeptide moiety. Preferably, at least one epitope, such as two, three or four epitopes of human recombinant IFNB (optionally comprising the C17S mutation) are shielded by a non-polypeptide moiety according to the invention. Accordingly, in one embodiment, the conjugate of the invention has at least one shielded epitope as compared to wild type human IFNB, optionally comprising the C17S mutation, including any commercially available IFNB. Preferably, the conjugate of the invention comprises a polypeptide that is modified so as to shield the epitope located in the vicinity of amino acid residue Q49 and/or F111. This may be done by introduction of an attachment group for a non-polypeptide moiety into a position located in the vicinity of (i.e. within 4 amino acid residues in the primary sequence or within about 10 Å in the tertiary sequence) of Q49 and/or F111. The 10 Å distance is measured between CB's (CA's in case of glycine). Such specific introductions are described in the following sections.

In case of removal of an attachment group, the relevant amino acid residue comprising such group and occupying a position as defined above is preferably substituted with a different amino acid residue that does not comprise an attachment group for the non-polypeptide moiety in question.

In case of introduction of an attachment group, an amino acid residue comprising such group is introduced into the position, preferably by substitution of the amino acid residue occupying such position.

The exact number of attachment groups available for conjugation and present in the IFNB polypeptide is dependent on the effect desired to be achieved by conjugation. The effect to be obtained is, e.g., dependent on the nature and degree of conjugation (e.g. the identity of the non-polypeptide moiety, the number of non-polypeptide moieties desirable or possible to conjugate to the polypeptide, where they should be conjugated or where conjugation should be avoided, etc.). For instance, if reduced immunogenicity is desired, the number (and location of) attachment groups should be sufficient to shield most or all epitopes. This is normally obtained when a greater proportion of the IFNB polypeptide is shielded. Effective shielding of epitopes is normally achieved when the total number of attachment groups available for conjugation is in the range of 1–10 attachment groups, in particular in the range of 2–8, such as 3–7.

Functional in vivo half-life is i.a. dependent on the molecular weight of the conjugate and the number of attachment groups needed for providing increased half-life thus depends on the molecular weight of the non-polypeptide moiety in question. In one embodiment, the conjugate of the invention has a molecular weight of at least 67 kDa, in particular at least 70 kDa as measured by SDS-PAGE according to Laemmli, U.K., Nature Vol 227 (1970), p 680–85. IFNB has a molecular weight of about 20 kDa, and therefore additional about 50 kDa is required to obtain the desired effect. This may be, e.g., be provided by 5, 10, 12, or 20 kDa PEG molecules or as otherwise described herein.

In order to avoid too much disruption of the structure and function of the parent human IFNB molecule the total number of amino acid residues to be altered in accordance with the invention (as compared to the amino acid sequence shown in SEQ ID NO:2) typically does not exceed 15. Preferably, the IFNB polypeptide comprises an amino acid sequence, which differs in 1–15 amino acid residues from the amino acid sequence shown in SEQ ID NO:2, such as in 1–8 or in 2–8 amino acid residues, e.g. in 1–5 or in 2–5 amino acid residues from the amino acid sequence shown in SEQ ID NO:2. Thus, normally the IFNB polypeptide comprises an amino acid sequence that differs from the amino acid sequence shown in SEQ ID NO:2 in 1, 2, 3, 4, 5, 6, 7, 8, 9, 10, 11, 12, 13, 14 or 15 amino acid residues. Preferably, the above numbers represent either the total number of introduced or the total number of removed amino acid residues comprising an attachment group for the relevant non-polypeptide moiety, or the total number of introduced and removed amino acid residues comprising such group.

In the conjugate of the invention it is preferred that at least about 50% of all conjugatable attachment groups, such as at least about 80% and preferably all of such groups are occupied by the relevant non-polypeptide moiety. Accordingly, in a preferred embodiment the conjugate of the invention comprises, e.g., 1–10 non-polypeptide moieties, such as 2–8 or 3–6.

The conjugate of the invention has one or more of the following improved properties (determined under comparable conditions):

Reduced immunogenicity as compared to wild-type human IFNB (e.g. Avonex or Rebif) or to Betaseron, e.g. a reduction of at least 25%, such as at least 50%, and more preferably at least 75%;

Increased functional in vivo half-life and/or increased serum half-life as compared to wild-type human IFNB (e.g. Avonex or Rebif) or to Betaseron;

Reduced or no reaction with neutralizing antibodies from patients treated with wildtype human IFNB (e.g. Rebif or Avonex) or with Betaseron, e.g. a reduction of neutralisation of at least 25%, such as of at least 50%, and preferably of at least 75% as compared to the wildtype human IFNB.

The magnitude of the antiviral activity of a conjugate of the invention may not be critical, and thus be reduced (e.g. by up to 75%) or increased (e.g. by at least 5%) or equal to that of wild-type human IFNB ((e.g. Avonex or Rebif) or to Betaseron as determined under comparable conditions.

Furthermore, the degree of antiviral activity as compared to antiproliferative activity of a conjugate of the invention may vary, and thus be higher, lower or equal to that of wildtype human IFNB.

Conjugate of the Invention, wherein the Non-polypeptide Moiety is a Molecule that has Lysine as an Attachment Group In a preferred aspect of the invention the first non-polypeptide moiety has lysine as an attachment group, and thus the IFNB polypeptide is one that comprises an amino acid sequence that differs from that of wildtype human IFNB in at least one introduced and/or at least one removed lysine residue. While the non-polypeptide moiety may be any of those binding to a lysine residue, e.g. the epsilon ($\epsilon$)-amino group thereof, such as a polymer molecule, a lipophilic group, an organic derivatizing agent or a carbohydrate moiety, it is preferably any of the polymer molecule mentioned in the section entitled "Conjugation to a polymer molecule", in particular a branched or linear PEG or polyalkylene oxide. Most preferably, the polymer molecule is PEG and the activated molecule to be used for conjugation is SS-PEG, NPC-PEG, aldehyd-PEG, mPEG-SPA, mPEG-SCM, mPEG-BTC from Shearwater Polymers, Inc, SC-PEG from Enzon, Inc., tresylated mPEG as described in U.S. Pat. No. 5,880,255, or oxycarbonyl-oxy-N-dicarboxyimide-PEG (U.S. Pat. No. 5,122,614). Normally, for conjugation to a lysine residue the non-polypeptide moiety has a molecular weight of about 5, 10, 12 or 20 kDa.

In one embodiment of the invention the amino acid sequence of the IFNB polypeptide differs from that of human wildtype IFNB in at least one removed lysine residue, such as 1–5 removed lysine residues, in particular 1–4 or 1–3 removed lysine residues. The lysine residue(s) to be removed, preferably by replacement, is selected from the group consisting of K19, K33, K45, K52, K99, K105, K108, K115, K123, K134, and K136. The lysine residue(s) may be replaced with any other amino acid residue, but is preferably replaced by an arginine or a glutamine residue in order to give rise to the least structural difference. In particular, the polypeptide part may be one, wherein K19, K45, K52 and/or K123, preferably K19, K45 and/or K123 has/have been replaced with another any other amino acid residue, preferably arginine or glutamine. For instance, the IFNB polypeptide part of a conjugate of the invention comprises a combination of amino acid substitutions selected from the following list:

K19R+K45R+K123R;
K19Q+K45R+K123R;
K19R+K45Q+K123R;
K19R+K45R+K123Q;
K19Q+K45Q+K123R;
K19R+K45Q+K123Q;
K19Q+K45R+K123Q;
K19Q+K45Q+K123Q;
K45R+K123R;
K45Q+K123R;
K45Q+K123Q;
K45R+K123Q;
K19R+K123R;
K19Q+K123R;
K19R+K123Q;
K19Q+K123Q;
K19R+K45R;
K19Q+K45R;
K19R+K45Q; or
K19Q+K45Q.

In addition or alternatively to the amino acid substitutions mentioned in the above list the polypeptide part may comprise at least one substitution selected from the group consisting of K33R, K33Q, K52R, K52Q, K99R, K99Q, K105R, K105Q, K108R, K108Q, K115R, K115Q, K134R, K134Q, K136R, and K136Q, e.g. at least one of the following substitutions:
K52R+K134R;
K99R+K136R;
K33R+K105R+K136R;
K52R+K108R+K134R;
K99R+K115R+K136R;
K19R+K33R+K45R+K123R;
K19R+K45R+K52R+K123R;
K19R+K33R+K45R+K52R+K123R; or
K19R+K45R+K52R+K99R+K123R.

In a further embodiment of the invention the amino acid sequence of the IFNB polypeptide differs from that shown in SEQ ID NO:2 in that a lysine residue has been introduced by substitution of at least one amino acid residue occupying a position that in the parent IFNB molecule is occupied by a surface exposed amino acid residue, preferably an amino acid residue having at least 25%, such as at least 50% of its side chain exposed to the surface. Preferably, the amino acid residue to be substituted is selected from the group consisting of N4, F8, L9, R11, S12, F15, Q16, Q18, L20, W22, Q23, G26, R27, L28, E29, Y30, L32, R35, M36, N37, D39, P41, E42, E43, LA7, Q48, Q49, T58, Q64, N65, F67, A68, R71, Q72, D73, S75, S76, G78, N80, E81, I83, E85, N86, A89, N90, Y92, H93, H97, T100, L102, E103, L106, E107, E109, D110, F111, R113, G114, L116, M117, L120, H121, R124, G127, R128, L130, H131, E137, Y138, H140, I145, R147, V148, E149, R152, Y155, F156, N158, R159, G162, Y163, R165 and N166 of SEQ ID NO:2.

More preferably, the amino acid sequence of the IFNB polypeptide differs from the amino acid sequence shown in SEQ ID NO:2 in that a lysine residue has been introduced, by substitution, of at least one amino acid residue occupying a position selected from the group consisting of N4, F8, L9, R11, S12, G26, R27, E29, R35, N37, D39, E42, L47, Q48, Q49, A68, R71, Q72, D73, S75, G78, N80, E85, N86, A89, Y92, H93, D110, F111, R113, L116, H121, R124, G127, R128, R147, V148, Y155, N158, R159, G162 and R165, even more preferably selected from the group consisting of N4, R11, G26, R27, Q48, Q49, R71, D73, S75, N80, E85, A89, Y92, H93, F111, R113, L116, R124, G127, R128, Y155, N158 and G162, and most preferably selected from the group consisting of R11, Q49, R71, S75, N80, E85, A89, H93, F111, R113, L116 and Y155, and most preferably Q49 and F111.

In accordance with this embodiment of the invention, the IFNB polypeptide comprises a substitution to lysine in one or more of the above positions, in particular in 1–15, such as 1–8 or 1–5, and preferably in at least two positions, such as 2–8 or 2–5 positions.

In a further embodiment of the invention the amino acid sequence of the IFNB polypeptide part of a conjugate differs in at least one removed and at least one introduced lysine residue, such as 1–5 or 2–5 removed lysine residues and 1–5 or 2–5 introduced lysine residues. It will be understood that the lysine residues to be removed and introduced preferably are selected from those described in the present section.

In accordance with this embodiment of the invention, the total number of conjugatable lysine residues is preferably in the range of 1–10, such as 2–8 or 3–7.

For instance, the IFNB polypeptide part of the conjugate according to this embodiment of the invention may comprise at least one of the following substitutions: R11K, Q48K, Q49K, R71 K, S75K, N80K, E85K, A89K, H93K, F111K, R113K, L116K and Y155K; more preferably R11K, Q49K, R71K, S75K, N80K, E85K, A89K, H93K, F111K, R113K, L116K and Y155K, in combination with at least one of the substitutions: K19R/Q K33R/Q K45R/Q, K52R/Q, K99R/Q, K105R/Q, K108R/Q, K115R/Q, K123R/Q, K134R/Q, and K136R/Q, wherein R/Q indicates substitution to an R or a Q residue, preferably an R residue. More preferably, the IFNB polypeptide comprises at least one of the following substitutions R11K, Q49K, R71K, S75K, N80K, E85K, A89K, H93K, F111K, R113K, L116K and Y155K, in particular Q49K, F111K and/or N80K, in combination with substitution of at least one of K19, K45, K52 and/or K123, preferably to an R or a Q residue. In particular, the IFNB polypeptide comprises at least one of the substitutions Q49K, F111K and N80K in combination with at least one of the substitutions mentioned above for removal of a lysine residue. For instance, the IFNB polypeptide may comprise the following substitutions:

Y+Z+K19R+K45R+K123R;
Y+Z+K19Q+K45R+K123R;
Y+Z+K19R+K45Q+K123R;
Y+Z+K19R+K45R+K123Q;
Y+Z+K19Q+K45Q+K123R;
Y+Z+K19R+K45Q+K123Q;
Y+Z+K19Q+K45R+K123Q;
Y+Z+K19Q+K45Q+K123Q;
Y+Z+K45R+K123R;
Y+Z+K45Q+K123R;
Y+Z+K45Q+K123Q;
Y+Z+K45R+K123Q;
Y+Z+K19R+K123R;
Y+Z+K19Q+K123R;
Y+Z+K19R+K123Q;
Y+Z+K19Q+K123Q;
Y+Z+K19R+K45R;
Y+Z+K19Q+K45R;
Y+Z+K19R+K45Q; or
Y+Z+K19Q+K45Q, wherein Y is selected from the group of Q49K, F111K, N80K, Q49K+F111K, Q49K+N80K, F111K+N80K and Q49K+F111K+N80K and Z is absent or comprises at least one substitution selected from the group consisting of K33R, K33Q, K52R, K52Q, K99R, K99Q, K105R, K105Q, K108R, K108Q, K115R, K115Q, K134R, K134Q, K136R, and K136Q. Preferably, the IFNB polypeptide comprises the following substitution Y+Z+K19R+K45Q+K123R, wherein Y and Z have the above meaning.

More specifically, according to this embodiment of the invention the IFNB polypeptide may comprise one of the following substitutions:

K19R+K45R+F111K+K123R;
K19R+K45R+Q49K+F111K+K123R;
K19R+K45R+Q49K+K123R;
K19R+K45R+F111K;
K19R+K45R+Q49K+F111K;
K19R+Q49K+K123R;
K19R+Q49K+F111K+K123R;
K45Q+F111K+K123Q;
K45R+Q49K+K123R; or
K45R+Q49K+F111K+K123R.

Especially for expression in a non-glycosylating host such as *E. coli* the IFNB polypeptide may contain the substitution N80K or C17S+N80K, optionally in combination with one or more of K19R/Q; K45R/Q; K52R/Q or K123R/Q. The substitution N80K is of particular interest, when the IFNB polypeptide is expressed in a non-glycosylating host cell, since N80 constitutes part of an inherent glycosylation site of human IFNB and conjugation at such site may mimic natural glycosylation.

Furthermore, it is preferred that the conjugate according to this aspect of the invention comprises at least two first non-polypeptide moieties, such as 2–8 moieties.

Conjugate of the Invention wherein the Non-polypeptide Moiety Binds to a Cysteine Residue In a still further aspect, the invention relates a conjugate exhibiting IFNB activity and comprising at least one first non-polypeptide conjugated to at least one cysteine residue of an IFNB polypeptide, the amino acid sequence of which differs from that of wildtype human IFNB in that at least one cysteine residue has been introduced, preferably by substitution, into a position that in the parent IFNB molecule is occupied by an amino acid residue that is exposed to the surface of the molecule, preferably one that has at least 25%, such as at least 50% of its side chain exposed to the surface. For instance, the amino acid residue is selected from the group consisting of F8, L9, R11, S12, F15, Q16, Q18, L20, W22, L28, L32, M36, P41, T58, Q64, N65, F67, I83, E85, N86, A89, N90, Y92, H93, H97, T100, L102, E103, L106, M117, L120, H121, R124, G127, R128, L130, H131, H140, I145, R147, V148, E149, R152, Y155, and F156 of SEQ ID NO:2.

Additionally or alternatively, the substitution is preferably performed at a position occupied by a threonine or serine residue. For instance, such position is selected from the group consisting of S2, S12, S13, T58, S74, S75, S76, T77, T82, T100, T112, S118, S119, S139, T144, and T161, more preferably S2, S12, S13, S74, S75, S76, T77, T82, T100, T112, S118, S119, S139, and T144 (side chain surface exposed), still more preferably S2, S12, S75, S76, T82, T100, S119 and S139 (at least 25% of its side chain exposed), and even more preferably S12, S75, T82 and T100 (at least 50% of its side chain exposed).

Of the above threonine or serine substitutions, serine substitutions are preferred. Accordingly, in even more preferred embodiments of the invention, the position is selected from the group consisting of S2, S12, S13, S74, S75, S76, S118, S119 and S139, more preferably S2, S12, S13, S74, S75, S76, S118, S119 and S139, even more preferably S2, S12, S75, S76, S119 and S139, and still more preferably S12 and S75.

In one embodiment, only one cysteine residue is introduced into the IFNB polypeptide in order to avoid formation of disulphide bridges between two or more introduced cysteine residues. In this connection C17 present in wildtype human IFNB may be removed, preferably by substitution, in particular by substitution with S or A. In another embodiment, two or more cysteine residues are introduced, such as 2–6 or 2–4 cysteine residues. Preferably, the IFNB polypeptide part of the conjugate according to this embodiment of the invention comprises the mutation L47C, Q48C, Q49C, D110C, F111C or R113C, in particular only one of these mutations, optionally in combination with the mutation C17S. Also, the IFNB polypeptide may comprise the substitution C17S+N80C.

While the first non-polypeptide moiety according to this aspect of the invention may be any molecule which, when using the given conjugation method has cysteine as an attachment group (such as a carbohydrate moiety, a lipophilic group or an organic derivatizing agent), it is preferred that the non-polypeptide moiety is a polymer molecule. The polymer molecule may be any of the molecules mentioned in the section entitled "Conjugation to a polymer molecule", but is preferably selected from the group consisting of linear or branched polyethylene glycol or polyalkylene oxide. Most preferably, the polymer molecule is VS-PEG. The conjugation between the polypeptide and the polymer may be achieved in any suitable manner, e.g. as described in the section entitled "Conjugation to a polymer molecule", e.g. in using a one step method or in the stepwise manner referred to in said section. When the IFNB polypeptide comprises only one conjugatable cysteine residue, this is preferably conjugated to a first non-polypeptide moiety with a molecular weight of at least 20 kDa, either directly conjugated or indirectly through a low molecular weight polymer (as disclosed in WO 99/55377). When the conjugate comprises two or more first non-polypeptide moieties, normally each of these has a molecular weight of 5 or 10 kDa.

Conjugate of the Invention wherein the Non-polypeptide Moiety Binds to an Acid Group In a still further aspect the invention relates to a conjugate exhibiting IFNB activity and comprising at least one first non-polypeptide moiety having an acid group as the attachment group, which moiety is conjugated to at least one aspartic acid residue or one glutamic acid residue of an IFNB polypeptide, the amino acid sequence of which differs from that of wildtype human IFNB in at least one introduced and/or at least one removed aspartic acid or glutamic acid residue, respectively. The relevant amino acid residue may be introduced in any position occupied by a surface exposed amino acid residue, preferably by an amino acid residue having more than 25% of its side chain surface exposed. Preferably, at least one amino acid residue occupying a position selected from the group consisting of N4, L5, L6, F8, L9, Q10, R11, S12, S13, F15, Q16, Q18, K19, L20, W22, Q23, L24, N25, G26, R27, Y30, M36, Q46, Q48, Q49, I66, F67, A68, I69, F70, R71, S75, T82, I83, L87, A89, N90, V91, Y92, H93, Q94, I95, N96, H97, K108, F111, L116, L120, K123, R124, Y126, G127, R128, L130, H131, Y132, K134, A135, H140, T144, R147, Y155, F156, N158, R159, G162, Y163 and R165 has been substituted with an aspartic acid residue or a glutamic acid residue.

More preferably, the position is selected from the group consisting of N4, L5, F8, L9, R11, S12, F15, Q16, Q18, K19, W22, Q23, G26, R27, Y30, M36, Q46, Q48, Q49, A68, R71, S75, T82, A89, N90, Y92, H93, N96, H97, K108, F111, L116, L120, K123, R124, G127, R128, L130, H131, K134, A135, H140, Y155, N158, R159, G162, Y163 and R165, such as from the group consisting of N4, L5, F8, S12, F15, Q16, K19, W22, Q23, R27, Y30, M36, Q46, Q48, Q49, R71, S75, T82, A89, Y92, H93, K108, F111, L116, K123, R124, G127, H131, K134, A135, Y155 and R165, still more preferably from the group consisting of N4, L5, F8, S12, F15, Q16, K19, W22, Q23, R27, Y30, Q46, Q48, Q49, S75, T82, A89, Y92, H93, K108, F111, L116, R124, G127, H131, K134, Y155 and R165, such as from the group consisting of L5, F8, S12, F15, Q16, K19, W22, Q23, Q48, Q49, Y92, H93, R124, G127, H131 and Y155, even more preferably from the group consisting of S12, Q16, K19, Q23, Q48, Q49, Y92, H93, R124, G127, H131 and Y155, such as from the group consisting of S12, Q16, K19, Q23, Q48, Y92, H93, R124, G127, H131 and Y155, in particular from the group consisting of S12, Q16, K19, Q23, Q48, H93 and H131, even more preferably from the group consisting of S12, Q16, K19, Q48, H93 and H131, and most preferably from the group consisting of Q16 and Q48.

Furthermore, in order to obtain a sufficient number of non-polypeptide moieties it is preferred that at least two aspartic acid residues or at least two glutamic acid residues be introduced, preferably in two positions selected from any of the above lists. Also, it is preferred that the conjugate according to this aspect of the invention comprises at least two first non-polypeptide moieties.

In case of removal of an amino acid residue, the amino acid sequence of the IFNB polypeptide differs from that of human wildtype IFNB in at least one removed aspartic acid or glutamic acid residue, such as 1–5 removed residues, in particular 1–4 or 1–3 removed aspartic acid or glutamic acid residues. The residue(s) to be removed, preferably by replacement, is selected from the group consisting of D34, D39, D54, D73, D110, E29, E42, E43, E53, E61, E81, E85, E103, E104, E107, E109, E137 and E149. The aspartic acid or glutamic acid residue(s) may be replaced with any other amino acid residue, but is preferably replaced by an arginine or a glutamine residue. While the first non-polypeptide moiety can be any non-polypeptide moiety with such property, it is presently preferred that the non-polypeptide moiety is a polymer molecule or an organic derivatizing agent having an acid group as an attachment group, in particular a polymer molecule such as PEG, and the conjugate is prepared, e.g., as described by Sakane and Pardridge, Pharmceutical Research, Vol. 14, No. 8, 1997, pp 1085–1091. Normally, for conjugation to an acid group the non-polypeptide moiety has a molecular weight of about 5 or 10 kDa.

Conjugate of the Invention Comprising a Second Non-polypeptide Moiety

In addition to a first non-polypeptide moiety (as described in the preceding sections), the conjugate of the invention may comprise a second non-polypeptide moiety of a different type as compared to the first non-polypeptide moiety. Preferably, in any of the above described conjugates wherein the first non-polypeptide moiety is, e.g., a polymer molecule such as PEG, a second non-polypeptide moiety is a sugar moiety, in particular an N-linked sugar moiety. While the second non-polypeptide moiety may be attached to a natural glycosylation site of human IFNB, e.g. the N-linked glycosylation site defined by N80, it is normally advantageous to introduce at least one additional glycosylation site in the IFNB polypeptide. Such site is e.g. any of those described in the immediately subsequent section entitled "Conjugate of the invention wherein the non-polypeptide moiety is a sugar moiety". Furthermore, in case at least one additional glycosylation site is introduced this may be accompanied by removal of an existing glycosylation site as described below.

It will be understood that in order to obtain an optimal distribution of attached first and second non-polypeptide moieties, the IFNB polypeptide may be modified in the number and distribution of attachment groups for the first as well as the second non-polypeptide moiety so as to have e.g. at least one removed attachment group for the first non-polypeptide moiety and at least one introduced attachment group for the second non-polypeptide moiety or vice versa. For instance, the IFNB polypeptide comprises at least two (e.g. 2–5) removed attachment groups for the first non-polypeptide moiety and at least one (e.g. 1–5) introduced attachment groups for the second non-polypeptide moiety or vice versa.

Of particular interest is a conjugate wherein the first non-polypeptide moiety is a polymer molecule such as PEG having lysine as an attachment group, and the second non-polypeptide moiety is an N-linked sugar moiety.

More specifically, the conjugate of the invention may be one exhibiting IFNB activity and comprising at least one polymer molecule, preferably PEG, and at least one sugar moiety covalently attached to an IFNB polypeptide, the amino acid sequence of which differs from that of wild-type human IFNB in a) at least one introduced and/or at least one removed amino acid residue comprising an attachment group for the polymer molecule; and b) at least one introduced and/or at least one removed in vivo glycosylation site, in particular an N-glycosylation site, provided that when the attachment group for the polymer molecule is a cysteine residue, and the sugar moiety is an N-linked sugar moiety, a cysteine residue is not inserted in such a manner that an N-glycosylation site is destroyed. WO 99/03887 suggests that a cysteine residue can be introduced into the natural N-glycosylation site of interferon β.

In a specific embodiment, the IFNB polypeptide comprises one of the following sets of mutations:
K19R+K45R+Q49N+Q51T+F111N+R113T+K123R;
K19R+K45R+Q49N+Q51T+F111N+R113T; or
K19R+K45R+Q49N+Q51T+K123R.

Conjugate of the Invention wherein the Non-polypeptide Moiety is a Sugar Moiety

When the conjugate of the invention comprises at least one sugar moiety attached to an in vivo glycosylation site, in particular an N-glycosylation site, this is either the natural N-glycosylation site of wild-type human IFNB at position N80, i.e. defined by amino acid residues N80, E81, T82 and I83, or a new in vivo glycosylation site introduced into the IFNB polypeptide. The in vivo glycosylation site may be an O-glycosylation site, but is preferably an N-glycosylation site.

More specifically, one aspect the invention relates to a conjugate exhibiting IFNB activity and comprising an IFNB polypeptide, the amino acid sequence of which differs from that of wild-type human IFNB in at least one introduced glycosylation site, the conjugate further comprising at least one un-PEGylated sugar moiety attached to an introduced glycosylation site.

In another aspect the invention relates to a conjugate exhibiting IFNB activity and comprising an IFNB polypeptide, the amino acid sequence of which differs from that of wild-type human IFNB in that a glycosylation site has been introduced or removed, provided that if only a glycosylation site is removed (and thus that no glycosylation site is introduced) the IFNB polypeptide does not comprise one or more of the following substitutions: N80C, E81C or T82C. The latter substitution is suggested in WO 99/03887.

For instance, an in vivo glycosylation site is introduced into a position of the parent IFNB molecule occupied by an amino acid residue exposed to the surface of the molecule, preferably with more than 25% of the side chain exposed to the solvent, in particular more than 50% exposed to the solvent (these positions are identified in the Methods section herein). The N-glycosylation site is introduced in such a way that the N-residue of said site is located in said position. Analogously, an O-glycosylation site is introduced so that the S or T residue making up such site is located in said position. Furthermore, in order to ensure efficient glycosylation it is preferred that the in vivo glycosylation site, in particular the N residue of the N-glycosylation site or the S or T residue of the O-glycosylation site, is located within the first 141 amino acid residues of the IFNB polypeptide, more preferably within the first 116 amino acid residues. Still more preferably, the in vivo glycosylation site is introduced into a position wherein only one mutation is required to create the site (i.e. where any other amino acid residues required for creating a functional glycosylation site is already present in the molecule).

Substitutions that lead to introduction of an additional N-glycosylation site at positions exposed at the surface of the IFNB molecule and occupied by amino acid residues having more than 25% of the side chain exposed to the surface include: S2N+N4S/T, L6S/T, L5N+G7S/T, F8N+ Q10S/T, L9N+R11S/T, R11N, R11N+S13T, S12N+N14S/T, F15N+C17S/T, Q16N+Q18S/T, Q18N+L20S/T, K19N+ L21S/T, W22N+L24S/T, Q23N+H25S/T, G26N+L28S/T, R27N+E29S/T, L28S+Y30S/T, Y30N+L32S/T, L32N+ D34S/T, K33N+R35S/T, R35N+N37S/T, M36N+F38S/T, D39S/T, D39N+P41S/T, E42N+I44S/T, Q43N+K45S/T, K45N+L47S/T, Q46N+Q48S/T, L47N+Q49T/S, Q48N+ F50S/T, Q49N+Q51S/T, Q51N+E53S/T, K52N+D54S/T, L57N+I59S/T, Q64N+I66S/T, A68N+F70S/T, R71N+D73S/ T, Q72N, Q72N+S74T, D73N, D73N+S75T, S75N+T77S, S75N, S76N+G78S/T, E81N+I83S/T, T82N+V84S/T, E85N+L87S/T, L88S/T, A89N+V91S/T, Y92S/T, Y92N+ Q94S/T, H93N+I95S/T, L98S/T, H97N+K99S/T, K99N+ V101S/T, T100N+L102S/T, E103N+K105S/T, E104N+L+ 106S/T, K105N+E107S/T, E107N+E109S/T, K108N+ D110S/T, E109N+F111S/T, D110N+T112S, D110N, F111N+R113S/T, R113N+K115S/T, G114N+L116S/T, K115N+M117S/T, L116N, L116N+S118T, S119N+H212S/ T, L120N+L122S/T, H121N+K123S/T, K123N+Y125S/T, R124N+Y126S/T, G127N+I129S/T, R128N+L130S/T, L130N+Y132S/T, H131N+L133S/T, K134N+K136S/T, A135N+E137S/T, K136N+Y138S/T, E137N, Y138N+ H140S/T, H140N+A142S/T, V148N+I150S/T, R152N+ F154S/T, Y155N+I157S/T, L160S/T, R159N+T161S, R159N, G162N+L164S/T, and Y163N+R165S/T.

Substitutions that lead to introduction of an additional N-glycosylation site at positions exposed at the surface of the IFNB molecule having more than 50% of the side chain exposed to the surface include:

L6S/T, L5N+G7S/T, F8N+Q10S/T, L9N+R11S/T, S12N+ N14S/T, F15N+C17S/T, Q16N+Q18S/T, K19N+L21S/T, W22N+L24S/T, Q23N+H25S/T, G26N+L28S/T, R27N+ E29S/T, Y30S/T, Y30N+L32S/T, K33N+R35S/T, R35N+N37S/T, M36N+F38S/T, D39S/T, D39N+P41S/T, E42N+I44S/T, Q46N+Q48S/T, Q48N+F50S/T, Q49N+Q51S/T, Q51N+ E53S/T, K52N+D54S/T, L57N+I59S/T, R71N+D73S/T, D73N, D73N+S75T, S75N+T77S, S75N, S76N+G78S/T, E81N+I83S/T, T82N+V84S/T, E85N+L87S/T, A89N+ V91S/T, Y92S/T, Y92N+Q94S/T, H93N+I95S/T, T100N+L102S/T, E103N+K105S/T, E104N+L106S/T, E107N+E109S/T, K108N+D110S/T, D110N+T112S, D110N, F111N+R113S/T, R113N+K115S/T, L116N, L116N+S118T, K123N+Y125S/T, R124N+Y126S/T, G127N+I129S/T, H131N+L133S/T, K134N+K136S/T, A135N+E137S/T, E137N, V148N+I150S/T, and Y155N+ I157S/T.

Among the substitutions mentioned in the above lists, those are preferred that have the N residue introduced among the 141 N-terminal amino acid residues, in particular among the 116 N-terminal amino acid residues.

Substitutions that lead to introduction of an N-glycosylation site by only one amino acid substitution include: L6S/T, R11N, D39S/T, Q72N, D73N, S75N, L88S/T, Y92S/ T, L98S/T, D110N, L116N, E137N, R159N and L160S/T. Among these, a substitution is preferred that is selected from the group consisting of L6S/T, R11N, D39S/T, Q72N, D73N, S75N, L88S/T, Y92S/T, L98S/T, D110N and L116N, more preferably from the group consisting of L6S/T, D39S/ T, D73N, S75N, L88S/T, D110N, L116N and E137N; and most preferably selected from the group consisting of L6S/T, D39S/T, D73N, S75N, L88S/T, D110N and L116N.

The presently most preferred IFNB polypeptide according to this aspect includes at least one of the following substitutions:
S2N+N4T/S, L9N+R11T/S, R11N, S12N+N14T/S, F15N+ C17S/T, Q16N+Q18T/S, K19N+L21T/S, Q23N+H25T/ S, G26N+L28T/S, R27N+E29T/S, L28N+Y30T/S, D39T/S, K45N+L47T/S, Q46N+Q48T/S, Q48N+F50T/S, Q49N+Q51T/S, Q51N+E53T/S, R71N+D73T/S, Q72N, D73N, S75N, S76N+G78T/S, L88T/S, Y92T/S, N93N+ I95T/S, L98T/S, E103N+K105T/S, E104N+L106T/S, E107N+E109T/S, K108N+D110T/S, D110N, F111N+ R113T/S, or L116N, more preferably at least one of the following substitutions: S2N+N4T, L9N+R11T, 49N+ Q51T or F111N+R113T or R71N+D73T, in particular 49N+Q51T or F111N+R113T or R71N+D73T. For instance, the IFNB polypeptide comprises one of the following sets of substitutions:

Q49N+Q51T+F111N+R113T;
Q49N+Q51T+R71N+D73T+F111N+R113T;
S2N+N4T+F111N+R113T;
S2N+N4T+Q49N+Q51T;
S2N+N4T+Q49N+Q51T+F111N+R113T;
S2N+N4T+L9N+R11T+Q49N+Q51T;
S2N+N4T+L9N+R11T+F111N+R113T;
S2N+N4T+L9N+R11T+Q49N+Q51T+F111N+R113T;
L9N+R11T+Q49N+Q51T;
L9N+R11T+Q49N+Q51T+F111N+R113T ; or
L9N+R11T+F111N+R113T

It will be understood that in order to introduce a functional in vivo glycosylation site the amino acid residue in between the N-residue and the S/T residue is different from proline. Normally, the amino acid residue in between will be that occupying the relevant position in the amino acid sequence shown in SEQ ID NO:2. For instance, in the polypeptide comprising the substitutions Q49N+Q51S, position 50 is the position in between.

The IFNB polypeptide part of a conjugate of the invention may contain a single in vivo glycosylation site. However, in order to obtain efficient shielding of epitopes present on the surface of the parent polypeptide it is often desirable that the polypeptide comprises more than one in vivo glycosylation site, in particular 2–7 in vivo glycosylation sites, such as 2, 3, 4, 5, 6 or 7 in vivo glycosylation sites. Thus, the IFNB polypeptide may comprise one additional glycosylation site, or may comprise two, three, four, five, six, seven or more introduced in vivo glycosylation sites, preferably introduced by one or more substitutions described in any of the above lists.

As indicated above, in addition to one or more introduced glycosylation sites, existing glycosylation sites may have been removed from the IFNB polypeptide. For instance, any of the above listed substitutions to introduce a glycosylation site may be combined with a substitution to remove the natural N-glycosylation site of human wild-type IFNB. For instance, the IFNB polypeptide may comprise a substitution of N80, e.g. one of the substitutions N80K/C/D/E, when a first non-polypeptide polypeptide is one having one of K, C, D, E as an attachment group. For instance, the IFNB polypeptide may comprise at least one of the following substitutions: S2N+N4T/S, L9N+R11T/S, R11N, S12N+ N14T/S, F15N+C17S/T, Q16N+Q18T/S, K19N+L21T/S, Q23N+H25T/S, G26N+L28T/S, R27N+E29T/S, L28N+ Y30T/S, D39T/S, K45N+LA7T/S, Q46N+Q48T/S, Q48N+ F50T/S, Q49N+Q51T/S, Q51N+E53T/S, R71N+D73T/S, Q72N, D73N, S75N, S76N+G78T/S, L88T/S, Y92T/S, N93N+I95T/S, L98T/S, E103N+K105T/S, E104N+L106T/S, E107N+E109T/S, K108N+D110T/S, D110N, F111N+R113T/S, or L116N in combination with N80K/C/D/E. More specifically, the IFNB polypeptide may comprise the substitution: Q49N+Q51T or F111N+R113T or R71N+D73T, in particular Q49N+Q51T+F111N+R113T or Q49N+Q51T+R71N+D73T+F111N+R113T, in combination with N80K/C/D/E.

Any of the glycosylated variants disclosed in the present section having introduced and/or removed at least one glycosylation site, such as the variant comprising the substitutions Q48N+F50T/S, Q48N+F50T/S+F111N+R113T/S, Q49N+Q51T/S, F111N+R113T/S, or Q49N+Q51T/S+F111N+R113T/S, may further be conjugated to a polymer molecule, such as PEG, or any other non-polypeptide moiety. For this purpose the conjugation may be achieved by use of attachment groups already present in the IFNB polypeptide or attachment groups may have been introduced and/or removed, in particular such that a total of 1–6, in particular 3–4 or 1, 2, 3, 4, 5, or 6 attachment groups are available for conjugation. Preferably, in a conjugate of the invention wherein the IFNB polypeptide comprises two glycosylation sites, the number and molecular weight of the non-polypeptide moiety is chosen so as that the total molecular weight added by the non-polypeptide moiety is in the range of 20–40 kDa, in particular about 20 kDa or 30 kDa.

In particular, the glycosylated variant may be conjugated to a non-polypeptide moiety via a lysine attachment group, and one or more lysine residues of the parent polypeptide may have been removed, e.g. by any of the substitutions mentioned in the section entitled "Conjugate of the invention, wherein the non-polypeptide moiety is a molecule which has lysine as an attachment group", in particular the substitutions K19R+K45R+K123R. Alternatively or additionally, a lysine residue may have been introduced, e.g. by any of the substitutions mentioned in said section, in particular the substitution R71 K. Accordingly, one specific conjugate of the invention is one, which comprises a glycosylated IFNB polypeptide comprising the mutations Q49N+Q51T+F111N+R113T+K19R+K45R+K123R or Q49N+Q51T+F111N+R113T+K19R+K45R+K123R+R71K further conjugated to PEG. The glycosylated polypeptide part of said conjugate is favourably produced in CHO cells and PEGylated subsequent to purification using e.g. SS-PEG, NPC-PEG, aldehyd-PEG, mPEG-SPA, mPEG-SCM, mPEG-BTC from Shearwater Polymers, Inc, SC-PEG from Enzon, Inc., tresylated mPEG as described in U.S. Pat. No. 5,880,255, or oxycarbonyl-oxy-N-dicarboxyimide-PEG (U.S. Pat. No. 5,122,614).

Alternatively, to PEGylation via a lysine group, the glycosylated conjugate according to this embodiment of the invention may be PEGylated via a cysteine group as described in the section entitled "Conjugate of the invention, wherein the non-polypeptide moiety is a molecule that has cysteine as an attachment group" (for this purpose the IFNB polypeptide may, e.g. comprising at least one of the mutations N80C, R71C and C17S), via an acid group as described in the section entitled "Conjugation of the invention wherein the non-polypeptide moiety binds to an acid group", or via any other suitable group.

Other Conjugates of the Invention

In addition to the introduction and/or removal of amino acid residues comprising an attachment group for the non-polypeptide moiety of choice (as described in any of the sections above entitled "Conjugate of the invention . . . ") the IFNB polypeptide part of the conjugate may contain further substitutions. A preferred example is a substitution of any of the residues, M1, C17, N80 or V101, e.g. one or more of the following substitutions: C17S; N80K/C/D/E; V101Y/W/F/, H; a deletion of M1; or M1K. The substitution M1K is of particular interest when the IFNB polypeptide is expressed with a tag, e.g. a His-14tag, where such tag is to be removed by DAP (diaminopeptidase) subsequent to purification and/or conjugation.

Non-polypeptide Moiety of a Conjugate of the Invention

As indicated further above the non-polypeptide moiety of the conjugate of the invention is preferably selected from the group consisting of a polymer molecule, a lipophilic compound, a sugar moiety (by way of in vivo glycosylation) and an organic derivatizing agent. All of these agents may confer desirable properties to the polypeptide part of the conjugate, in particular reduced immunogenicity and/or increased functional in viva half-life and/or increased serum half-life. The polypeptide part of the conjugate may be conjugated to only one type of non-polypeptide moiety, but may also be conjugated to two or more different types of non-polypeptide moieties, e.g. to a polymer molecule and a sugar moiety, to a lipophilic group and a sugar moiety, to an organic derivatizing agent and a sugar moiety, to a lipophilic group and a polymer molecule, etc. The conjugation to two or more different non-polypeptide moieties may be done simultaneous or sequentially. The choice of non-polypeptide moiety/ies, e.g. depends on the effect desired to be achieved by the conjugation. For instance, sugar moieties have been found particularly useful for reducing immunogenicity, whereas polymer molecules such as PEG are of particular use for increasing functional in vivo half-life and/or serum half-life. Using a polymer molecule as a first non-polypeptide moiety and a sugar moiety as a second non-polypeptide moiety may result in reduced immunogenicity and increased functional in vivo or serum half-life.

Methods of Preparing a Conjugate of the Invention

In the following sections "Conjugation to a lipophilic compound", "Conjugation to a polymer molecule", "Conjugation to a sugar moiety" and "Conjugation to an organic derivatizing agent" conjugation to specific types of non-polypeptide moieties is described.

Conjugation to a Lipophilic Compound

For conjugation to a lipophilic compound the following polypeptide groups may function as attachment groups: the N-terminal or C-terminal of the polypeptide, the hydroxy groups of the amino acid residues Ser, Thr or Tyr, the ε-amino group of Lys, the SH group of Cys or the carboxyl group of Asp and Glu. The polypeptide and the lipophilic compound may be conjugated to each other, either directly or by use of a linker. The lipophilic compound may be a natural compound such as a saturated or unsaturated fatty acid, a fatty acid diketone, a terpene, a prostaglandin, a vitamin, a carotenoid or steroid, or a synthetic compound such as a carbon acid, an alcohol, an amine and sulphonic acid with one or more alkyl-, aryl-, alkenyl- or other multiple unsaturated compounds. The conjugation between the polypeptide and the lipophilic compound, optionally through a linker may be done according to methods known in the art, e.g. as described by Bodanszky in Peptide Synthesis, John Wiley, New York, 1976 and in WO 96/12505.

Conjugation to a Polymer Molecule

The polymer molecule to be coupled to the polypeptide may be any suitable polymer molecule, such as a natural or synthetic homo-polymer or heteropolymer, typically with a molecular weight in the range of 300–100,000 Da, such as 300–20,000 Da, more preferably in the range of 500–10,000 Da, even more preferably in the range of 500–5000 Da.

Examples of homo-polymers include a polyol (i.e. poly-OH), a polyamine (i.e. poly-$NH_2$) and a polycarboxylic acid (i.e. poly-COOH). A hetero-polymer is a polymer, which comprises one or more different coupling groups, such as, e.g., a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), polycarboxylate, poly-(vinylpyrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared, e.g., to polysaccharides such as dextran, and the like. In particular, monofunctional PEG, e.g monomethoxy-polyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control. When the interferon molecule is PEGylated it usually comprises 1–5 polyethylene glycol (PEG) molecules. In a further embodiment the interferon molecule comprises 1–5 PEG molecules, such as 1, 2 or 3 PEG molecules. In a further embodiment each PEG molecule has a molecular weight of about 5 kDa (kilo Dalton) to 100 kDa. In a further embodiment each PEG molecule has a molecular weight of about 10 kDa to 40 kDa. In a further embodiment each PEG molecule has a molecular weight of about 12 kDa. In a further embodiment each PEG molecule has a molecular weight of about 20 kDa. Preferably the interferon molecule comprises 1–3 PEG molecules each having a molecular weight of about 12 kDa, or 1 PEG molecule having a molecular weight of about 20 kDa. Suitable PEG molecules are available from Shearwater Polymers, Inc. and Enzon, Inc. and may be selected from SS-PEG, NPC-PEG, aldehyd-PEG, mPEG-SPA, mPEG-SCM, mPEG-BTC, SC-PEG, tresylated mPEG (U.S. Pat. No. 5,880,255), or oxycarbonyl-oxy-N-dicarboxyimide-PEG (U.S. Pat. No. 5,122,614).

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidyl carboxymethylate (SCM), benzotriazole carbonate (BTC), N-hydroxysuccinimide (NHS), aldehyde, nitrophenylcarbonate (NPC), and tresylate (TRES)). Suitably activated polymer molecules are commercially available, e.g. from Shearwater Polymers, Inc., Huntsville, Ala., USA or Poly-Masc, UK. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference). Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG), BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which references are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 5,382,657, EP 510 356, EP 400 472, EP 183 503 and EP 154 316.

The conjugation of the polypeptide and the activated polymer molecules is conducted by use of any conventional method, e.g. as described in the following references (which also describe suitable methods for activation of polymer molecules): Harris and Zalipsky, eds., Poly(ethylene glycol) Chemistry and Biological Applications, AZC, Washington; R. F. Taylor, (1991), "Protein immobilisation. Fundamental and applications", Marcel Dekker, N.Y.; S. S. Wong, (1992), "Chemistry of Protein Conjugation and Crosslinking", CRC Press, Boca Raton; G. T. Hermanson et al., (1993), "Immobilized Affinity Ligand Techniques", Academic Press, N.Y.). The skilled person will be aware that the activation method and/or conjugation chemistry to be used depends on the attachment group(s) of the IFNB polypeptide as well as the functional groups of the polymer (e.g. being amino, hydroxyl, carboxyl, aldehyde or sulfydryl). The PEGylation may be directed towards conjugation to all available attachment groups on the polypeptide (i.e. such attachment groups that are exposed at the surface of the polypeptide) or may be directed towards specific attachment groups, e.g. the N-terminal amino group (U.S. Pat. No. 5,985,265). Furthermore, the conjugation may be achieved in one step or in a stepwise manner (e.g. as described in WO 99/55377).

It will be understood that the PEGylation is designed so as to produce the optimal molecule with respect to the number of PEG molecules attached, the size and form (e.g. whether they are linear or branched) of such molecules, and where in the polypeptide such molecules are attached. For instance, the molecular weight of the polymer to be used may be chosen on the basis of the desired effect to be achieved. For instance, if the primary purpose of the conjugation is to achieve a conjugate having a high molecular weight (e.g. to reduce renal clearance) it is usually desirable to conjugate as few high Mw polymer molecules as possible to obtain the desired molecular weight. When a high degree of epitope shielding is desirable this may be obtained by use of a sufficiently high number of low molecular weight polymer (e.g. with a molecular weight of about 5,000 Da) to effectively shield all or most epitopes of the polypeptide. For instance, 2–8, such as 3–6 such polymers may be used.

In connection with conjugation to only a single attachment group on the protein (as described in U.S. Pat. No. 5,985,265), it may be advantageous that the polymer molecule, which may be linear or branched, has a high molecular weight, e.g. about 20 kDa.

Normally, the polymer conjugation is performed under conditions aiming at reacting all available polymer attachment groups with polymer molecules. Typically, the molar ratio of activated polymer molecules to polypeptide is 1000-1, in particular 200-1, preferably 100-1, such as 10-1 or 5-1 in order to obtain optimal reaction. However, also equimolar ratios may be used.

It is also contemplated according to the present invention to couple the polymer molecules to the polypeptide through a linker. Suitable linkers are well known to the skilled person. A preferred example is cyanuric chloride (Abuchowski et al., (1977), J. Biol. Chem., 252, 3578–3581; U.S. Pat. No. 4,179,337; Shafer et al., (1986), J. Polym. Sci. Polym. Chem. Ed., 24, 375–378.

Subsequent to the conjugation residual activated polymer molecules are blocked according to methods known in the art, e.g. by addition of primary amine to the reaction mixture, and the resulting inactivated polymer molecules removed by a suitable method.

Covalent in vitro coupling of a carbohydrate moiety to amino acid residues of IFNB may be used to modify or increase the number or profile of carbohydrate substituents. Depending on the coupling mode used, the carbohydrate(s) may be attached to a) arginine and histidine (Lundblad and Noyes, Chemical Reagents for Protein Modification, CRC Press Inc. Boca Raton, Fla.), b) free carboxyl groups (e.g. of the C-terminal amino acid residue, asparagine or glutamine), c) free sulfhydryl groups such as that of cysteine, d) free hydroxyl groups such as those of serine, threonine, tyrosine or hydroxyproline, e) aromatic residues such as those of phenylalanine or tryptophan or f) the amide group of glutamine. These amino acid residues constitute examples of attachment groups for a carbohydrate moiety, which may be introduced and/or removed in the IFNB polypeptide. Suitable methods of in vitro coupling are described in WO 87/05330 and in Aplin et al., CRC Crit. Rev. Biochem., pp. 259–306, 1981. The in vitro coupling of carbohydrate moieties or PEG to protein- and peptide-bound Gln-residues can also be carried out by transglutaminases (TGases), e.g. as described by Sato et al., 1996 Biochemistry 35, 13072–13080 or in EP 725145.

Coupling to a Sugar Moiety

In order to achieve in vivo glycosylation of an IFNB polypeptide as described herein, e.g. one that has been modified by introduction of one or more glycosylation sites (see the section "Conjugates of the invention wherein the non-polypeptide moiety is a sugar moiety") or by modification of an amino acid residue located close to a glycosylation site (as described in the section entitled "Variants with increased glycosylation"), the nucleotide sequence encoding the polypeptide part of the conjugate must be inserted in a glycosylating, eucaryotic expression host. The expression host cell may be selected from fungal (filamentous fungal or yeast), insect, mammalian, animal and transgenic plain cells or from transgenic animals. Furthermore, the glycosylation may be achieved in the human body when using a nucleotide sequence encoding a polypeptide described herein in gene therapy. In one embodiment the host cell is a mammalian cell, such as an CHO cell, BHK or HEK cell, e.g. HEK293, or an insect cell, such as an SF9 cell, or a yeast cell, e.g. *Saccharomyces cerevisiae, Pichia pasroris* or any other suitable glycosylating host, e.g. as described further below. Optionally, sugar moieties attached to the IFNB polypeptide by in vivo glycosylation are further modified by use of glycosyltransferases, e.g. using the glycoAdvance™ technology marketed by Neose, Horsham, Pa., USA. Thereby, it is possible to, e.g., increase the sialylation of the glycosylated IFNB polypeptide following expression and in vivo glycosylation by CHO cells.

Coupling to an Organic Derivatizing Agent

Covalent modification of the IFNB polypeptide may be performed by reacting (an) attachment group(s) of the polypeptide with an organic derivatizing agent. Suitable derivatizing agents and methods are welt known in the art. For example, cysteinyl residues most commonly are reacted with α-haloacetates (and corresponding amines), such as chloroacetic acid or chloroacetamide, to give carboxymethyl or carboxyaminomethyl derivatives. Cysteinyl residues also are derivatized by reaction with bromotrifluoroacetone, α-bromo-β-(4-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole. Histidyl residues are derivatized by reaction with diethylpyrocarbonate at pH 5.5–7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anbydrides. Derivatization with these agents has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourca; 2,4-pentanedione; and transaminase-catalyzed reaction with glyoxylate. Arginyl residues are modified by reaction with one or several conventional reagents, among them phenylglyoxal, 2,3-buranedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine guanidino group. Carboxyl side groups (aspartyl or glutamyl or C-terminal amino acid residue) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and gluraminyl residues by reaction with ammonium ions.

Blocking of Functional Site

It has been reported that excessive polymer conjugation can lead to a loss of activity of the interferon β polypeptide to which the polymer is conjugated. This problem can be eliminated, e.g., by removal of attachment groups located at the functional site or by blocking the functional site prior to conjugation. These latter strategies constitute further embodiments of the invention (the first strategy being exemplified further above, e.g. by removal of lysine residues which may be located close to a functional site). More specifically, according to the second strategy the conjugation between the interferon β polypeptide and the non-polypeptide moiety is conducted under conditions where the functional site of the polypeptide is blocked by a helper molecule capable of binding to the functional site of the polypeptide. Preferably, the helper molecule is one, which specifically recognizes a functional site of the polypeptide, such as a receptor, in particular the type I interferon receptor. Alternatively, the helper molecule may be an antibody, in particular a monoclonal antibody recognizing the interferon β polypeptide. In particular, the helper molecule may be a neutralizing monoclonal antibody.

The polypeptide is allowed to interact with the helper molecule before effecting conjugation. This ensures that the functional site of the polypeptide is shielded or protected and consequently unavailable for derivatization by the non-polypeptide moiety such, as a polymer. Following its elution from the helper molecule, the conjugate between the non-polypeptide moiety and the polypeptide can be recovered with at least a partially preserved functional site.

The subsequent conjugation of the polypeptide having a blocked functional site to a polymer, a lipophilic compound, an organic derivatizing agent or any other compound is conducted in the normal way, e.g. as described in the sections above entitled "Conjugation to . . . ".

Irrespectively of the nature of the helper molecule to be used to shield the functional site of the polypeptide from conjugation, it is desirable that the helper molecule is free from or comprises only a few attachment groups for the non-polypeptide moiety of choice in part(s) of the molecule, where the conjugation to such groups will hamper the desorption of the conjugated polypeptide from the helper molecule. Hereby, selective conjugation to attachment groups present in non-shielded parts of the polypeptide can be obtained and it is possible to reuse the helper molecule for repeated cycles of conjugation. For instance, if the non-polypeptide moiety is a polymer molecule such as PEG, which has the epsilon amino group of a lysine or N-terminal amino acid residue as an attachment group, it is desirable that the helper molecule is substantially free from conjugatable epsilon amino groups, preferably free from any epsilon amino groups. Accordingly, in a preferred embodiment the helper molecule is a protein or peptide capable of binding to the functional site of the polypeptide, which protein or peptide is free from any conjugatable attachment groups for the non-polypeptide moiety of choice.

In a further embodiment the helper molecule is first covalently linked to a solid phase such as column packing materials, for instance Sephadex or agarose beads, or a surface, e.g. reaction vessel. Subsequently, the polypeptide is loaded onto the column material carrying the helper molecule and conjugation carried out according to methods known in the art, e.g. as described in the sections above entitled "Conjugation to . . . ". This procedure allows the polypeptide conjugate to be separated from the helper molecule by elution. The polypeptide conjugate is eluated by conventional techniques under physico-chemical conditions that do not lead to a substantive degradation of the polypeptide conjugate. The fluid phase containing the polypeptide conjugate is separated from the solid phase to which the helper molecule remains covalently linked. The separation can be achieved in other ways: For instance, the helper molecule may be derivatised with a second molecule (e.g. biotin) that can be recognized by a specific binder (e.g. streptavidin). The specific binder may be linked to a solid phase thereby allowing the separation of the polypeptide conjugate from the helper molecule-second molecule complex through passage over a second helper-solid phase column which will retain, upon subsequent elution, the helper molecule-second molecule complex, but not the polypeptide conjugate. The polypeptide conjugate may be released from the helper molecule in any appropriate fashion. De-protection may be achieved by providing conditions in which the helper molecule dissociates from the functional site of the interferon β to which it is bound. For instance, a complex between an antibody to which a polymer is conjugated and an anti-idiotypic antibody can be dissociated by adjusting the pH to an acid or alkaline pH.

Conjugation of a Tagged Interferon β Polypeptide

In an alternative embodiment the interferon β polypeptide is expressed, as a fusion protein, with a tag, i.e. an amino acid sequence or peptide stretch made up of typically 1–30, such as 1–20 or 1–15 or 1–10 amino acid residues. Besides allowing for fast and easy purification, the tag is a convenient tool for achieving conjugation between the tagged polypeptide and the non-polypeptide moiety. In particular, the tag may be used for achieving conjugation in microtiter plates or other carriers, such as paramagnetic beads, to which the tagged polypeptide can be immobilised via the tag. The conjugation to the tagged polypeptide in, e.g., microtiter plates has the advantage that the tagged polypeptide can be immobilised in the microtiter plates directly from the culture broth (in principle without any purification) and subjected to conjugation. Thereby, the total number of process steps (from expression to conjugation) can be reduced. Furthermore, the tag may function as a spacer molecule ensuring an improved accessibility to the immobilised polypeptide to be conjugated. The conjugation using a tagged polypeptide may be to any of the non-polypeptide moieties disclosed herein, e.g. to a polymer molecule such as PEG.

The identity of the specific tag to be used is not critical as long as the tag is capable of being expressed with the polypeptide and is capable of being immobilised on a suitable surface or carrier material. A number of suitable tags are commercially available, e.g. from Unizyme Laboratories, Denmark. For instance, the tag may be any of the following sequences:

```
His-His-His-His-His-His                                      (SEQ ID NO:49)

Met-Lys-His-His-His-His-His-His                              (SEQ ID NO:50)

Met-Lys-His-His-Ala-His-His-Gln-His-His                      (SEQ ID NO:51)

Met-Lys-His-Gln-His-Gln-His-Gln-His-Gln-His-Gln-His-Gln      (SEQ ID NO:52)

(vectors useful for providing such tags are available from Unizyme
Laboratories, Denmark)
```

-continued
or any of the following:

EQKLI SEEDL (a C-terminal tag described in Mol. Cell. Biol. 5:3610-16, 1985; SEQ ID NO:53)

DYKDDDDK (a C- or N-terminal tag; SEQ ID NO:54)

YPYDVPDYA (SEQ ID NO:55)

Antibodies against the above tags are commercially available, e.g. from ADI, Aves Lab and Research Diagnostics.

A convenient method for using a tagged polypeptide for PEGylation is given in the Materials and Methods section below.

The subsequent cleavage of the tag from the polypeptide may be achieved by use of commercially available enzymes.

Polypeptides of the Invention

In further aspects the invention relates to generally novel interferon β polypeptides described herein that, as compared to human wildtype interferon β has at least one introduced and/or at least one removed attachment group for a non-polypeptide moiety. The novel polypeptides are important intermediate compounds for the preparation of a conjugate of the invention. In addition, the polypeptides themselves may have interesting properties.

Examples of such polypeptides include those that comprises an amino acid sequence which differs from that of wild-type human interferon β in that at least one amino acid residue selected from the group consisting of N4, F8, L9, Q10, R11, S13, L24, N25, G26, L28, E29, N37, F38, Q48, Q49, Q64, N65, I66, F67, A68, I69, F70, R71, Q72, D73, S74, S75, S76, T77, G78, W79, N80, E81, T82, I83, V84, L87, L88, A89, N90, V91, Y92, H93, Q94, D110, F111, T112, R113, R128, H140, T144, I145, R147, V148, L151, R152, F154, Y155, N158 and N166 is replaced with a different amino acid residue selected from the group consisting of K, R, D, E, C and N. The amino acid residues specified above are located in positions, which are exposed at the surface of human interferon β molecule as demonstrated by the solved 3D structure of human interferon β. By replacing one or more of these residue with either of K, R, D, E, C and N attachment group(s) for a non-polypeptide moiety, in particular a polymer attachment group or an amino acid residue susceptible to modification by a carbohydrate moiety, is/are introduced into human interferon β. The resulting modified human interferon β molecule is a suitable starting compound for the preparation of an interferon β conjugate having improved properties as compared to the unmodified human interferon β molecule.

In a further aspect the invention relates to an interferon β polypeptide comprising an amino acid sequence which differs from that of wild-type human interferon P in that an least one amino acid residue selected from the group consisting of N4, F8, L9, Q10, R11, S12, S13, L24, N25, G26, L28, E29, N37, F38, D39, Q48, Q49, Q64, N65, I66, F67, A68, i69, F70, R71, Q72, D73, S74, S75, S76, T77, G78, W79, N80, E81, T82, I83, V84, P85, L87, L28, A89, N90, V91, Y92, H93, Q94, D110, F111, T112, R113, R128, H140, T144, I145, R147, V148, L151, R152, F154, Y155, N158, G162, and N166 is replaced with a lysine residue, provided that the polypepticle is different from the one having the amino acid sequence of wild-type human interferon β with the following substitutions: D54N+E85K+V91I+V101M and different from one which is a hybrid molecule between interferon β and interferon α which as a consequence of being a hybrid has a lysine in position 39. The first of the disclaimed polypeptides is disclosed by Stewart et al., DNA, Vol. 6, No. 2, 1987, pp. 119–128 and was found to be inactive, the second is disclosed in U.S. Pat. No. 4,769,233 and was constructed with the purpose of improving the biological activity of interferon β. None of the disclaimed polypeptides were made for or described as being suitable intermediates for the preparation of interferon β conjugates with reduced immunogenicity and/or prolonged functional in vivo half-life and/or serum half-life.

A still further example includes an interferon β polypeptide comprising an amino acid sequence which differs from that of SEQ ID NO:2 in one or more substitutions selected from the group consisting of N4K, F15K, Q16K, R27K, R35K, D39K, Q49K, E85K, A89K, E103K, E109K, R124K, E137K and R159K, provided that when the substitution is R27K the polypeptide is different from the one having the amino acid sequence of wild-type human interferon β with the following substitutions: R27K+E43K. The disclaimed polypeptide is disclosed by Stewart et al., DNA. Vol. 6, No. 2, 1987, pp. 119–128 and was found to have a low activity. The polypeptide was made in the course of a study of function-structure relationship and was not mentioned as a possible intermediate product for the preparation of improved interferon β conjugate molecules. For instance, the interferon β polypeptide comprises an amino acid sequence, which differs from that of SEQ ID NO:2 in that it comprises the substitution R27K in combination with at least one additional substitution that is different from E43K, or the substitution R35K in combination with at least one additional substitution provided that the polypeptide has an amino acid sequence which is different from the amino acid sequence of wild-type human interferon β modified with the following substitutions:

G7E+S12N'C17Y+R35K. The disclaimed polypeptide is disclosed by Stewart et al., DNA, Vol. 6, No. 2, 1987, pp. 119–128 as having a retained antiproliferative activity on Daudi cells relative to their antiviral activity, but reduced overall activity as compared to wild type interferon β. The disclaimed polypeptide was not prepared with the purpose of reducing the immunogenicity and/or increasing the functional in vivo half-life and/or serum half-life, but was made in the course of a study of the structural functional relationship of interferon β.

The polypeptide of the invention may, in addition to any of the above specified substitutions, additionally comprise the substitution C17S and/or a deletion of M1 or the substitution M1K. Furthermore, the polypeptide of the invention may comprise an amino acid sequence, which further differs from that of SEQ ID NO:2 in the removal, preferably by substitution, of at least one lysine residue selected from the group consisting of K19, K33, K45, K52, K99, K105, K108, K115, K123, K134, and K136. The lysine residue(s) may be replaced with any other amino acid residue, but is preferably replaced by an arginine or a glutamine. In particular, the polypeptide of the invention may be one, wherein K45, K52 and/or K123 has/have been replaced with another amino acid residue, but preferably an arginine or a glutamine residue. Also, the polypeptide may be expressed with a tag.

A still further example of an interferon β polypeptide of the invention includes one, that comprises an amino acid sequence which differs from that of wild-type human interferon β in that at least one lysine residue selected from the group consisting of K19, K33, K45, K52, K99, K105, K108, K115, K123, K134, and K136 has been replaced with any other amino acid residue, provided that the interferon β polypeptide is different from a hybrid between interferon β and interferon α, which as a consequence of being a hybrid has a phenylalanine in position 45. Preferably, at least K19, K45, K52 and/or K123 is/are are replaced. While the lysine residue may be deleted in accordance with this aspect of the invention, it is preferred that it be replaced with any other amino acid residue, preferably an arginine or a glutamine. Normally, the polypeptide of the invention comprises an amino acid sequence which differs in 1–15 amino acid residues from the amino acid sequence shown in SEQ ID NO:2 as further discussed above. Examples of polypeptides of the invention are selected from the group consisting of those that comprises an amino acid sequence, which differs from that of SEQ ID NO:2 in at least the following substitutions:

R27K+R159K;
R27K+K45R+R159K;
R27K+Q49K+E85K+A89K;
R27K+K45R+Q49K+E85K+A89K;
R27K+D39K+Q49K+E85K+A89K;
R27K+D39K+K45R+Q49K+E85K+A89K;
N4K+R7K+D39K+Q49K+E85K+A89K;
N4K+R27K+D39K+K45R+Q49K+E85K+A89K;
R27K+K123R+R159K;
R27K+K45R+K123R+R159K;
R27K+Q49K+E85K+A89K+K123R;
R27K+K45R+Q49K+E85K+A89K+K123R;
R27K+D39K+Q49K+E85K+A89K+K123R;
R27K+D39K+K45R+Q49K+E85K+A89K+K123R;
N4K+R27K+D39K+Q49K+E85K+A89K+K123R; and
N4K+R27K+D39K+K45R+Q49K+E85K+A89K+K123R.

It will be understood that any polypeptide of the invention disclosed herein may be used to prepare a conjugate of the invention, i.e. be covalently coupled to any of the non-polypeptide moieties disclosed herein. In particular, when a polypeptide of the invention is expressed in a glycosylating microorganism the polypeptide may be provided in glycosylated form. It will be further understood that any polypeptide of the invention disclosed herein may be utilised as a parent IFNB polypeptide to prepare a polypeptide variant of the invention, as described avove.

Methods of Preparing an IFNB Polypeptide of the Invention

The polypeptide of the present invention, optionally in glycosylated form, may be produced by any suitable method known in the art. Such methods include constructing a nucleotide sequence encoding the polypeptide and expressing the sequence in a suitable transformed or transfected host. However, polypeptides of the invention may be produced, albeit less efficiently, by chemical synthesis or a combination of chemical synthesis or a combination of chemical synthesis and recombinant DNA technology.

The nucleotide sequence of the invention encoding an IFNB polypeptide may be constructed by isolating or synthesizing a nucleotide sequence encoding the parent IFNB, e.g. with the amino acid sequence shown in SEQ ID NO:2, and then changing the nucleotide sequence so as to effect introduction (i.e. insertion or substitution) or deletion (i.e. removal or substitution) of the relevant amino acid residue(s).

The nucleotide sequence is conveniently modified by site-directed mutagenesis in accordance with well-known methods, see, e.g., Mark et al., "Site-specific Mutagenesis of the Human Fibroblast Interferon Gene", Proc. Natl. Acad. Sci. USA, 81, pp. 5662–66 (1984); and U.S. Pat. No. 4,588,585.

Alternatively, the nucleotide sequence is prepared by chemical synthesis, e.g. by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction (LCR). The individual oligonucleotides typically contain 5' or 3' overhangs for complementary assembly.

Once assembled (by synthesis, site-directed mutagenesis or another method), the nucleotide sequence encoding the IFNB polypeptide is inserted into a recombinant vector and operably linked to control sequences necessary for expression of the IFNB in the desired transformed host cell.

It should of course be understood that not all vectors and expression control sequences function equally well to express the nucleotide sequence encoding a polypeptide variant described herein. Neither will all hosts function equally well with the same expression system. However, one of skill in the art may make a selection among these vectors, expression control sequences and hosts without undue experimentation. For example, in selecting a vector, the host must be considered because the vector must replicate in it or be able to integrate into the chromosome. The vector's copy number, the ability to control that copy number, and the expression of any other proteins encoded by the vector, such as antibiotic markers, should also be considered. In selecting an expression control sequence, a variety of factors should also be considered. These include, for example, the relative strength of the sequence, its controllability, and its compatibility with the nucleotide sequence encoding the polypeptide, particularly as regards potential secondary structures. Hosts should be selected by consideration of their compatibility with the chosen vector, the toxicity of the product coded for by the nucleotide sequence, their secretion characteristics, their ability to fold the polypeptide correctly, their fermentation or culture requirements, and the ease of purification of the products coded for by the nucleotide sequence.

The recombinant vector may be an autonomously replicating vector, i.e. a vector which exists as an extrachromosomal entity, the replication of which is independent of chromosomal replication, e.g. a plasmid. Alternatively, the vector is one which, when introduced into a host cell, is integrated into the host cell genome and replicated together with the chromosome(s) into which it has been integrated.

The vector is preferably an expression vector, in which the nucleotide sequence encoding the polypeptide of the invention is operably linked to additional segments required for transcription of the nucleotide sequence. The vector is typically derived from plasmid or viral DNA. A number of suitable expression vectors for expression in the host cells mentioned herein are commercially available or described in the literature. Useful expression vectors for eukaryotic hosts, include, for example, vectors comprising expression control sequences from SV40, bovine papilloma virus, adenovirus and cytomegalovirus. Specific vectors are. e.g., pCDNA3.1 (+)\Hyg (Invitrogen, Carlsbad, Calif., USA) and pCI-neo (Stratagene, La Jolla, Calif., USA). Useful expression vectors for bacterial hosts include known bacterial plasmids, such as plasmids from *E. coli*, including pBR322, pET3a and pET12a (both from Novagen Inc., WI, USA), wider host range plasmids, such as RP4, phage DNAs, e.g., the numerous derivatives of phage lambda, e.g., NM989, and other DNA phages, such as M13 and filamentous single stranded DNA phages. Useful expression vectors for yeast cells include the 2μ plasmid and derivatives thereof, the POT1 vector (U.S. Pat. No. 4,931,373), the pJSO37 vector described in (Okkels, Ann. New York Aced. Sci. 782, 202–207, 1996) and pPICZ A, B or C (Invitrogen). Useful vectors for insect cells include pVL941, pBG311 (Cate et al., "Isolation of the Bovine and Human Genes for Mullerian Inhibiting Substance And Expression of the Human Gene In Animal Cells", Cell, 45, pp. 685–98 (1986), pBluebac 4.5 and pMelbac (both available from Invitrogen).

Other vectors for use in this invention include those that allow the nucleotide sequence encoding the polypeptide variant to be amplified in copy number. Such amplifiable vectors are well known in the art. They include, for example, vectors able to be amplified by DHFR amplification (see, e.g., Kaufman, U.S. Pat. No. 4,470,461, Kaufman and Sharp, "Construction Of A Modular Dihydrofolate Reductase cDNA Gene: Analysis Of Signals Utilized For Efficient Expression", Mol. Cell. Biol., 2, pp. 1304–19 (1982)) and glutamine synthetase ("GS") amplification (see, e.g., U.S. Pat. No. 5,122,464 and EP 338,841).

The recombinant vector may further comprise a DNA sequence enabling the vector to replicate in the host cell in question. An example of such a sequence (when the host cell is a mammalian cell) is the SV40 origin of replication. When the host cell is a yeast cell, suitable sequences enabling the vector to replicate are the yeast plasmid 2μ replication genes REP 1–3 and origin of replication.

The vector may also comprise a selectable marker, e.g. a gene the product of which complements a defect in the host cell, such as the gene coding for dihydrofolate reductase (DHFR) or the *Schizosaccharomyces pombe* TPI gene (described by P. R. Russell, Gene 40, 1985, pp. 125–130), or one which confers resistance to a drug, e.g. ampicillin, kanamycin, tetracyclin, chloramphenicol, neomycin, hygromycin or methotrexate. For filamentous fungi, selectable markers include amdS, pyrG, arcB, niaD, sC.

The term "control sequences" is defined herein to include all components, which are necessary or advantageous for the expression of the IFNB polypeptide. Each control sequence may be native or foreign to the nucleic acid sequence encoding the polypeptide. Such control sequences include, but are not limited to, a leader, polyadenylation sequence, propeptide sequence, promoter, enhancer or upstream activating sequence, signal peptide sequence, and transcription terminator. At a minimum, the control sequences include a promoter.

A wide variety of expression control sequences may be used in the present invention. Such useful expression control sequences include the expression control sequences associated with structural genes of the foregoing expression vectors as well as any sequence known to control the expression of genes of prokaryotic or eukaryotic cells or their viruses, and various combinations thereof.

Examples of suitable control sequences for directing transcription in mammalian cells include the early and late promoters of SV40 and adenovirus, e.g. the adenovirus 2 major late promoter, the MT-1 (metallothionein gene) promoter, the human cytomegalovirus immediate-early gene promoter (CMV), the human elongation factor 1α (EF-1α) promoter, the *Drosophila* minimal heat shock protein 70 promoter, the Rous Sarcoma Virus (RSV) promoter, the human ubiquitin C (UbC) promoter, the human growth hormone terminator, SV40 or adenovirus Elb region polyadenylation signals and the Kozak consensus sequence (Kozak, M. *J Mol Biol* 1987 Aug. 20;196(4):947–50).

In order to improve expression in mammalian cells a synthetic intron may be inserted in the 5' untranslated region of the nucleotide sequence encoding the polypeptide of interest. An example of a synthetic intron is the synthetic intron from the plasmid pCI-Neo (available from Promega Corporation, WI, USA).

Examples of suitable control sequences for directing transcription in insect cells include the polyhedrin promoter, the P10 promoter, the *Autographa californica* polyhedrosis virus basic protein promoter, the baculovirus immediate early gene 1 promoter and the baculovirus 39K delayed-early gene promoter, and the SV40 polyadenylation sequence.

Examples of suitable control sequences for use in yeast host cells include the promoters of the yeast α-mating system, the yeast triose phosphate isomerase (TPI) promoter, promoters from yeast glycolytic genes or alcohol dehydogenase genes, the ADH2-4c promoter and the inducible GAL promoter.

Examples of suitable control sequences for use in filamentous fungal host cells include the ADH3 promoter and terminator, a promoter derived from the genes encoding *Aspergillus oryzae* TAKA amylase triose phosphate isomerase or alkaline protease, an *A. niger* α-amylase, *A. niger* or *A. nidulans* glucoamylase, *A. nidulans* acetamidase, *Rhizomucor miehei* aspartic proteinase or lipase, the TPI1 terminator and the ADH3 terminator.

Examples of suitable control sequences for use in bacterial host cells include promoters of the lac system, the trp system, the TAC or TRC system and the major promoter regions of phage lambda.

The nucleotide sequence of the invention encoding an IFNB polypeptide, whether prepared by site-directed mutagenesis, synthesis or other methods, may or may not also include a nucleotide sequence that encode a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with human IFNB) or heterologous (i.e. originating from another source than human IFNB) to the polypeptide or may be homologous or heterologous to the host cell, i.e. be a signal peptide normally expressed from the host cell or one which is not normally expressed from the host cell. Accordingly, the signal peptide may be prokaryotic, e.g. derived from a bacterium such as *E. coli*, or eukaryotic, e.g. derived from a mammalian, or insect or yeast cell.

The presence or absence of a signal peptide will, e.g., depend on the expression host cell used for the production of the polypeptide, the protein to be expressed (whether it is an intracellular or extracellular protein) and whether it is desirable to obtain secretion. For use in filamentous fungi, the signal peptide may conveniently be derived from a gene encoding an *Aspergillus* sp. amylase or glucoamylase, a gene encoding a *Rhizomucor miehei* lipase or protease or a *Humicola lanuginosa* lipase. The signal peptide is preferably derived from a gene encoding *A. oryzae* TAKA amylase, *A. niger* neutral α-amylase, *A. niger* acid-stable amylase, or *A. niger* glucoamylase. For use in insect cells, the signal peptide may conveniently be derived from an insect gene (cf. WO 90/05783), such as the lepidopteran *Manduca sexta* adipokinetic hormone precursor, (cf. U.S. Pat. No. 5,023,328), the honeybee melittin (Invitrogen), ecdysteroid UDPglucosyltransferase (egt) (Murphy et al., Protein Expression and Purification 4, 349–357 (1993) or human pancreatic lipase (hpl) (Methods in Enzymology 284, pp. 262–272, 1997).

A preferred signal peptide for use in mammalian cells is that of human IFNB apparent from the examples hereinafter or the murine Ig kappa light chain signal peptide (Coloma, M (1992) J. 1 mm. Methods 152:89–104). For use in yeast cells suitable signal peptides have been found to be the α-factor signal peptide from *S. cereviciae*. (cf. U.S. Pat. No. 4,870,008), the signal peptide of mouse salivary amylase (cf. O. Hagenbuchle et al., Nature 289, 1981, pp. 643–646), a modified carboxypeptidase signal peptide (cf. L. A. Valls et al., Cell 48, 1987, pp. 887–897), the yeast BAR1 signal peptide (cf. WO 87/02670), and the yeast aspartic protease 3 (YAP3) signal peptide (cf. M. Egel-Mitani et al., Yeast 6, 1990, pp. 127–137).

Any suitable host may be used to produce the IFNB polypeptide, including bacteria, fungi (including yeasts), plant, insect, mammal, or other appropriate animal cells or cell lines, as well as transgenic animals or plants. Examples of bacterial host cells include grampositive bacteria such as strains of Bacillus, e.g. *B. brevis* or *B. subtilis*, *Pseudomonas* or *Streptomyces*, or gramnegative bacteria, such as strains of *E. coli*. The introduction of a vector into a bacterial host cell may, for instance, be effected by protoplast transformation (see, e.g., Chang and Cohen, 1979, *Molecular General Genetics* 168: 111–115), using competent cells (see, e.g., Young and Spizizin, 1961, *Journal of Bacteriology* 81: 823–829, or Dubnau and Davidoff-Abelson, 1971, *Journal of Molecular Biology* 56: 209–221), electroporation (see, e.g., Shigekawa and Dower, 1988, *Biotechniques* 6: 742–751), or conjugation (see, e.g., Koehler and Thorne, 1987, *Journal of Bacteriology* 169: 5771–5278).

Examples of suitable filamentous fungal host cells include strains of *Aspergillus*, e.g. *A. oryzae*, *A. niger*, or *A. nidulans*, *Fusarium* or *Trichoderma*. Fungal cells may be transformed by a process involving protoplast formation, transformation of the protoplasts, and regeneration of the cell wall in a manner known per se. Suitable procedures for transformation of *Aspergillus* host cells are described in EP 238 023 and U.S. Pat. No. 5,679,543. Suitable methods for transforming *Fusarium* species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology*, Methods in Enzymology, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

Examples of suitable yeast host cells include strains of *Saccharomyces*, e.g. *S. cerevisiae*, *Schizosaceharomyces*, *Klyveromyces*, *Pichia*, such as *P. pastoris* or *P. methanolica*, *Hansenula*, such as *H. Polymorpha* or *Yarrowia*. Methods for transforming yeast cells with heterologous DNA and producing heterologous polypeptides therefrom are disclosed by Clontech Laboratories, Inc. Palo Alto, Calif., USA (in the product protocol for the Yeastmaker™ Yeast Transformation System Kit), and by Reeves et al., FEMS Microbiology Letters 99 (1992) 193–198, Manivasakam and Schiestl, Nucleic Acids Research, 1993, Vol. 21, No. 18, pp. 4414–4415 and Ganeva et al., FEMS Microbiology Letters 121 (1994) 159–164.

Examples of suitable insect host cells include a *Lepidoptora* cell line, such as *Spodoptera frugiperda* (Sf9 or Sf21) or *Trichoplusioa ni* cells (High Five) (U.S. Pat. No. 5,077, 214). Transformation of insect cells and production of heterologous polypeptides therein may be performed as described by Invitrogen.

Examples of suitable mammalian host cells include Chinese hamster ovary (CHO) cell lines, (e.g. CHO-K1; ATCC CCL-61), Green Monkey cell lines (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. Additional suitable cell lines are known in the art and available from public depositories such as the American Type Culture Collection, Rockville, Md. Also, the mammalian cell, such as a CHO cell, may be modified to express sialyltransferase, e.g. 1,6-sialyltransferase, e.g. as described in U.S. Pat. No. 5,047,335, in order to provide improved glycosylation of the IFNB polypeptide.

Methods for introducing exogenous DNA into mammalian host cells include calcium phosphare-mediated transfection, electroporation, DEAE-dextran mediated transfection, liposome-mediated transfection, viral vectors and the transfection methods described by Life Technologies Ltd, Paisley, UK using Lipofectamin 2000 and Roche Diagnostics Corporation, Indianapolis, USA using FuGENE 6. These methods are well known in the arc and e.g. described by Ausbel et al. (eds.), 1996, Current Protocols in Molecular Biology, John Wiley & Sons, New York, USA. The cultivation of mammalian cells are conducted according to established methods, e.g. as disclosed in (Animal Cell Biotechnology, Methods and Protocols, Edited by Nigel Jenkins, 1999, Human Press Inc. Totowa, N.J., USA and Harrison Mass. and Rae IF, General Techniques of Cell Culture, Cambridge University Press 1997).

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The resulting polypeptide may be recovered by methods known in the art. For example, the polypeptide may be recovered from the nutrient medium by conventional procedures including, but not limited to, centrifugation, filtration, extraction, spray drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989). Specific methods for purifying polypeptides exhibiting IFNB activity are disclosed in U.S. Pat. No. 4,289,689, U.S. Pat. No. 4,359,389, U.S. Pat. No. 4,172,071, U.S. Pat. No. 4,551,271, U.S. Pat. No. 5,244,655, U.S. Pat. No. 4,485,017, U.S. Pat. No. 4,257,938 and U.S. Pat. No. 4,541,952. A specific purification method is based on immunoaffinity purification (see, e.g., Okamura et al., "Human Fibroblastoid Interferon: Immunosorbent Column Chromatography And N-Terminal Amino Acid Sequence", Biochem., 19, pp. 3831–35 (1980)). Also, hydroxyapatite chromatography may be used. Furthermore, purification may be based on the use of IFNAR 1 and/or IFNAR 2, in particular IFNAR 2.

The biological activity of the IFNB polypeptides can be assayed by any suitable method known in the art. Such assays include antibody neutralization of antiviral activity, induction of protein kinase, oligoadenylate 2,5-A synthetase or phosphodiesterase activities, as described in EP 41313 B1. Such assays also include immunomodulatory assays (see, e.g., U.S. Pat. No. 4,753,795), growth inhibition assays, and measurement of binding to cells that express interferon receptors. Specific assays for determining the biological activity of polypeptides or conjugates of the invention are disclosed in the Materials and Methods section hereinafter.

Cell Culture of the Invention

In a further aspect the invention relates to a cell culture comprising a) a host cell transformed with a nucleotide sequence encoding a polypeptide exhibiting interferon β activity, and b) a culture medium comprising said polypeptide produced by expression of said nucleotide sequence in a concentration of at least 800,000 IU/ml of medium, preferably in a concentration in the range of 800,000–3,500,000 IU/ml medium. While the polypeptide exhibiting interferon β activity may be a wild-type interferon β, e.g. human interferon β or a variant thereof (e.g. interferon β 1a or 1b) the polypeptide is preferably an interferon β polypeptide as described herein.

In a still further aspect the invention relates to a method of producing an interferon β polypeptide as described herein, the method comprising:

(a) culturing a cell expressing an interferon β polypeptide variant in a culture medium, such that the concentration of the interferon β polypeptide variant in the medium is at least 800,000 IU/ml medium, in particular in the range of between 800,000 and 3,500,000 IU/ml medium; and (b) recovering the interferon β polypeptide.

Other Methods of the Invention

In a still further aspect the invention relates to a method reducing immunogenicity and/or of increasing functional in vivo half-life and/or serum half-life of an interferon β polypeptide, which method comprises introducing an amino acid residue constituting an attachment group for a first non-polypeptide moiety into a position exposed at the surface of the protein that does not contain such group and/or removing an amino acid residue constituting an attachment group for a first non-polypeptide moiety and subjecting the resulting modified polypeptide to conjugation with the first non-polypeptide moiety.

Preferably, the amino acid residue to be introduced and/or removed is as defined in the present application. The non-polypeptide moiety is normally selected from the group consisting of a polymer molecule, a sugar moiety, a lipophilic group and an organic derivatizing agent.

In a still further aspect the invention relates to a method for preparing a conjugate of the invention, wherein the interferon β polypeptide is reacted with the non-polypeptide moiety to which it is to be conjugated under conditions conducive for the conjugation to take place, and the conjugate is recovered.

Pharmaceutical Composition and Uses of a Conjugate of the Invention

The IFNB molecule or conjugate of the invention is administered at a dose approximately paralleling that employed in therapy with human IFNB such as Avonex, Rebif and Betaseron, or a higher dose. The exact dose to be administered depends on the circumstances. Normally, the dose should be capable of preventing or lessening the severity or spread of the condition or indication being treated. It will be apparent to those of skill in the art that an effective amount of an IFNB molecule or conjugate depends, inter alia, upon the disease, the dose, the administration schedule, whether the molecule or conjugate is administered alone or in conjunction with other therapeutic agents, the serum half-life of the compositions, and the general health of the patient.

The IFNB molecule or conjugate of the invention can be used "as is" and/or in a salt form thereof. Suitable salts include, but are not limited to, salts with alkali metals or alkaline earth metals, such as sodium, potassium, lithium, calcium and magnesium, as well as e.g. zinc salts. These salts or complexes may by present as a crystalline and/or amorphous structure.

The molecule or conjugate of the invention is preferably administered in a composition further including a pharmaceutically acceptable carrier or excipient. "Pharmaceutically acceptable" means a carrier or excipient that does not cause any untoward effects in patients to whom it is administered. Such pharmaceutically acceptable carriers and excipients are well known in the art.

The molecule or conjugate of the invention can be formulated into pharmaceutical compositions by well-known methods. Suitable formulations are described in U.S. Pat. No. 5,183,746, Remington's Pharmaceutical Sciences by E. W. Martin, 18$^{th}$ edition, A. R. Gennaro, Ed., Mack Publishing Company [1990]; Pharmaceutical Formulation Development of Peptides and Proteins, S. Frokjaer and L. Hovgaard, Eds., Taylor & Francis [2000]; and Handbook of Pharmaceutical Excipients, 3rd edition, A. Kibbe, Ed., Pharmaceutical Press [2000]).

The molecule or conjugate of the invention may be formulated into a pharmaceutical composition in a variety of forms, including liquid, gel, lyophilized, pulmonary dispersion, or any other suitable form, e.g. as a compressed solid. The preferred form will depend upon the particular indication being treated and will be apparent to one of skill in the art.

The pharmaceutical composition of the invention may be administered parenterally (e.g. intravenously, intramuscularly, intraperitoneally, or subcutaneously), orally, intracerebrally, intradermally, intranasally, intrapulmonary, by inhalation, or in any other acceptable manner, e.g. using PowderJect or ProLease technology. The preferred mode of administration will depend upon the particular indication being treated and will be apparent to one of skill in the art.

Pharmaceutical Composition Comprising an IFNB Polypeptide without Free Cysteine

It has surprisingly been found that IFNB polypeptides that do not have a free cysteine, e.g., the C17 of human IFNB derived polypeptides, has a significantly reduced tendency to aggregate as compared to IFNB polypeptides comprising a free cysteine. This observation has important implications not only in the production of IFNB polypeptides (which becomes less complicated), but also with respect to the need of using stabilizers minimizing the aggregation of IFNB polypeptides when formulated into pharmaceutical products.

Accordingly, in a further aspect the invention relates to a pharmaceutical composition comprising a glycosylated IFNB polypeptide that comprises the substitution C17S (relative to SEQ ID NO:2), the composition comprising a reduced amount of stabilizer as compared to the amount required to prepare a pharmaceutical composition comprising a glycosylated IFNB polypeptide comprising C17 but otherwise having the same amino acid sequence. For instance, the amount of stabilizer may be reduced by at least 50%, such as by at least 75% or an even higher percentage. Of particular interest is a pharmaceutical composition comprising an IFNB polypeptide that comprises the substitution C17S (relative to SEQ ID NO:2), the composition being substantially free from a stabilizer.

The IFNB polypeptide according to this aspect may be any glycosylated IFNB free from a free cysteine, and may, e.g., be any of the parent IFNB molecules, the polypeptide part of a conjugate (glycosylated and optionally conjugated to a second non-polypeptide moiety), or a glycosylated variant as described herein (i.e. in the sections "Conjugate of the invention wherein the non-polypeptide moiety is a sugar moiety" or "Variants with increased glycosylation"). When the IFNB polypeptide is derived from human IFNB it has an amino acid residue different from cysteine in position 17, and comprises, e.g., the mutation C17S.

The stabilizer which is reduced or not present may be any of those mentioned in the sections below. For instance, the stabilizer is HAS or a non-ionic surfactant such as Tween, e.g. Tween 20 or Tween 80.

Parenterals

An example of a pharmaceutical composition is a solution designed for parenteral administration. Although in many cases pharmaceutical solution formulations are provided in liquid form, appropriate for immediate use, such parenteral formulations may also be provided in frozen or in lyophilized form. In the former case, the composition must be thawed prior to use. The latter form is often used to enhance the stability of the active compound contained in the composition under a wider variety of storage conditions, as it is recognized by those skilled in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

In case of parenterals, they are prepared for storage as lyophilized formulations or aqueous solutions by mixing, as appropriate, the polypeptide having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from about 2 mM to about 50 mM Suitable buffering agents for use with the present invention include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives are added to retard microbial growth, and are typically added in amounts of about 0.2%–1% (w/v). Suitable preservatives for use with the present invention include phenol, benzyl alcohol, meta-cresol, methyl paraben, propyl paraben, octadecyldimethylbenzyl ammonium chloride, benzalkonium halides (e.g. benzalkonium chloride, bromide or iodide), hexamethonium chloride, alkyl parabens such as methyl or propyl paraben, catechol, resorcinol, cyclohexanol and 3-pentanol.

Isotonicifiers are added to ensure isotonicity of liquid compositions and include polyhydric sugar alcohols, preferably trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur-containing reducing agents, such as urea, glutathione, thioctic acid, sodium thioglycolate, thioglycerol, α-monothioglycerol and sodium thiosulfate; low molecular weight polypeptides (i.e. <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Non-ionic surfactants or detergents (also known as "wetting agents") may be present to help solubilize the therapeutic agent as well as to protect the therapeutic polypeptide against agitation-induced aggregation, which also permits the formulation to be exposed to shear surface stress without causing denaturation of the polypeptide. Suitable non-ionic surfactants include polysorbates (20, 80, etc.), polyoxamers (184, 188 etc.), Pluronic® polyols, polyoxyethylene sorbitan monoethers (Tween®-20, Tween®-80, etc.).

Stabilizers are typically present in the range of from 0.1 to 10,000 parts by weight based on the active protein weight, but may be reduced or absent in case of a pharmaceutical composition of the invention as defined in the section entitled "Pharmaceutical composition comprising an IFNB polypeptide without free cysteine".

Additional miscellaneous excipients include bulking agents or fillers (e.g. starch), chelating agents (e.g. EDTA), antioxidants (e.g., ascorbic acid, methionine, vitamin E) and cosolvents. The active ingredient may also be entrapped in microcapsules prepared, for example, by coacervation techniques or by interfacial polymerization, for example hydroxymethylcellulose, gelatin or poly-(methylmethacylate) microcapsules, in colloidal drug delivery systems (for example liposomes, albumin microspheres, microemulsions, nano-particles and nanocapsules) or in macroemulsions. Such techniques are disclosed in Remington's Pharmaceutical Sciences, supra. A typical parenteral liquid formulation comprises any one of the glycosylated IFNbeta variants disclosed herein, such as the glycosylated variants having a 12 kDa PEG or 20 kDa PEG attached, and Captisol® in a concentration from about 10 mg/ml to 50 mg/ml. In addition, the formulation may comprise mannitol in a concentration up to 50 mg/ml, such as 32, or 34 mg/ml. Suitably, the initial variant concentration is 5–15 MIU/ml, such as 5–10, or 10–14 MIU/ml, in a buffer selected from acetate, or succinate, said buffer having a concentration ranging from 10–50 mM, eg 10 mM, and a pH of from 5–6, such as 5.5. Moreover, Tween 20 or Tween 80 may be added to the formulation in a concentration up to 2 mg/ml.

Parenteral formulations to be used for in vivo administration must be sterile. This is readily accomplished, for example, by filtration through sterile filtration membranes.

Sustained Release Preparations

Suitable examples of sustained-release preparations include semi-permeable matrices of solid hydrophobic polymers containing the molecule or conjugate of the invention, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the ProLease® technology or Lupron Depot® (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Pulmonary Delivery

Conjugate or polypeptide formulations suitable for use with a nebulizer, either jet or ultrasonic, will typically comprise the molecule or conjugate dissolved in water at a concentration of, e.g., about 0.01 to 25 mg of conjugate per mL of solution, preferably about 0.1 to 10 mg/mL. The formulation may also include a buffer and a simple sugar (e.g., for protein stabilization and regulation of osmotic pressure), and/or human serum albumin ranging in concentration from 0.1 to 10 mg/ml. Examples of buffers that may be used are sodium acetate, citrate and glycine. Preferably, the buffer has a composition and molarity suitable to adjust the solution to a pH in the range of 3 to 9. Generally, buffer molarities of from 1 mM to 50 mM are suitable for this purpose. Examples of sugars which can be utilized are lactose, maltose, mannitol, sorbitol, trehalose, and xylose, usually in amounts ranging from 1% to 10% by weight of the formulation.

The nebulizer formulation may also contain a surfactant to reduce or prevent surface induced aggregation of the protein caused by atomization of the solution in forming the aerosol. Various conventional surfactants can be employed, such as polyoxyethylene fatty acid esters and alcohols, and polyoxyethylene sorbitan fatty acid esters. Amounts generally range between 0.001% and 4% by weight of the formulation. An especially preferred surfactant for purposes of this invention is polyoxyethylene sorbitan monooleate.

Specific formulations and methods of generating suitable dispersions of liquid particles of the invention are described in WO 9420069, U.S. Pat. No. 5,915,378, U.S. Pat. No. 5,960,792, U.S. Pat. No. 5,957,124, U.S. Pat. No. 5,934,272, U.S. Pat. No. 5,915,378, U.S. Pat. No. 5,855,564, U.S. Pat. No. 5,826,570, and U.S. Pat. No. 5,522,385 which are hereby incorporated by reference.

Three specific examples of commercially available nebulizers suitable for the practice of this invention are the Ultravent nebulizer, manufactured by Mallinckrodt, Inc., St. Louis, Mo., the Acorn II nebulizer, manufactured by Marquest Medical Products, Englewood, Colo., and the AERx pulmonary drug delivery system manufactured by Aradigm Corporation, Hayward, Calif.

Formulations of the invention for use with a metered dose inhaler device generally comprise a finely divided powder. This powder may be produced by lyophilizing and then milling a liquid formulation and may also contain a stabilizer such as human serum albumin (HSA). Typically, more than 0.5% (w/w) HSA is added. Additionally, one or more sugars or sugar alcohols may be added to the preparation if necessary. Examples include lactose maltose, mannitol, sorbitol, sorbitose, trehalose, xylitol, and xylose. The amount added to the formulation can range from about 0.01 to 200% (w/w), preferably from approximately 1 to 50%, of the conjugate present. Such formulations are then lyophilized and milled to the desired particle size.

The properly sized particles are then suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2-tetrafluoroethane, or combinations thereof. Suitable surfactants include sorbitan trioleate and soya lecithin. Oleic acid may also be useful as a surfactant.

This mixture is then loaded into the delivery device. An example of a commercially available metered dose inhaler suitable for use in the present invention is the Ventolin metered dose inhaler, manufactured by Glaxo Inc., Research Triangle Park, N.C.

Such formulations for powder inhalers will comprise a finely divided dry powder containing the IFNB molecule or conjugate and may also include a bulking agent, such as lactose, sorbitol, sucrose, or mannitol in amounts which facilitate dispersal of the powder from the device, e.g., 50% to 90% by weight of the formulation. The particles of the powder shall have aerodynamic properties in the lung corresponding to particles with a density of about 1 g/cm$^2$ having a median diameter less than 10 micrometers, preferably between 0.5 and 5 micrometers, most preferably of between 1.5 and 3.5 micrometers.

An example of a powder inhaler suitable for use in accordance with the teachings herein is the Spinhaler powder inhaler, manufactured by Fisons Corp., Bedford, Mass.

The powders for these devices may be generated and/or delivered by methods disclosed in U.S. Pat. No. 5,997,848, U.S. Pat. No. 5,993,783, U.S. Pat. No. 5,985,248, U.S. Pat. No. 5,976,574, U.S. Pat. No. 5,922,354, U.S. Pat. No. 5,785,049, U.S. Pat. No. 6,123,936 and U.S. Pat. No. 5,565,4007.

The pharmaceutical composition containing the molecule or conjugate of the invention may be administered by a wide range of mechanical devices designed for pulmonary delivery of therapeutic products, including but limited to nebulizers, metered dose inhalers, and powder inhalers, all of which are familiar to those of skill in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, N.C.; the Spinhaler powder inhaler, manufactured by Fisons Corp., Bedford, Mass.; the "standing cloud" device of Inhale Therapeutic Systems, Inc., San Carlos, Calif.; the AIR inhaler manufactured by Alkermes, Cambridge, Mass.; and the AERx pulmonary drug delivery system manufactured by Aradigm Corporation, Hayward, Calif.

The pharmaceutical composition of the invention may be administered in conjunction with other therapeutic agents. These agents may be incorporated as part of the same pharmaceutical composition or may be administered separately from the IFNB molecule of the invention, either concurrently or in accordance with any other acceptable treatment schedule. In addition, the molecule or pharmaceutical composition of the invention may be used as an adjunct to other therapies.

Accordingly, this invention provides compositions and methods for treating most types of viral infections, cancers or tumors or tumour angiogenesis, Chrohn's disease, ulcerative colitis, Guillain-Barré syndrome, glioma, idiopathic pulmonary fibrosis, abnormal cell growth, or for immunomodulation in any suitable animal, preferably mammal, and in particular human. For example, the molecule or composition of the invention or conjugate of the invention may be used in the treatment of osreosarcoma, basal cell carcinoma, ovarian carcinoma, cervical dysplasia, cervical carcinoma, laryngeal papillomatosis, mycosis fungoides, glioma, acute myeloid leukemia, multiple myeloma, Hodgkin's disease, melanoma, breast carcinoma, non-small cell lung cancer, malignant melanoma (adjuvant, late stage, as well as prophylactic), carcinoid tumour, B-cell lymphoma, T-cell lymphoma, follicular lymphoma, Kaposi's sarcoma, chronic myelogenous leukaemia, renal cell carcinoma, recurrent superficial bladder cancer, colorectal carcinoma, hairy cell leukaemia, and viral infections such as papilloma virus, viral hepatitis, herpes genitalis, herpes zoster, herpetic keratitis, herpes simplex, viral encephalitis, cytomegalovirus pneumonia, rhinovirus chronic persistent hepatitis, chronic active HCV (type I), chronic active HCV (type II) and chronic hepatitis B.

In this connection, a conjugate or a variant according to the present invention may be used for CML monotherapy or in combination with cytarabne, for B-cell lymphoma monotherapy or in combination with doxorubicin-based regimens, for follicular lymphoma therapy as an adjunct to CHOP-like regimen, for hepatitis C monotherapy or in combination with ribavirin, for multiple myeloma monotherapy or in combination with VBMCP, BCNU or VBMCP+HiCy, or for renal carcinoma monotherapy or in combination with Vinblastine, floxuridine, 5-fluoruouracil or IL-10.

In particular the molecule or conjugate or composition of the invention may be used for the treatment of multiple sclerosis (MS), such as any of the generally recognized four types of MS (benign, relapsing remitting MS (RRMS), primary progressive MS (PPMS) and secondary progressive MS (SPMS)) and for monosymptomatic MS), cancer or tumours, hepatitis, e.g. hepatitis B and hepatitis C, or a herpes infection (the latter treatment optionally being combined with a treatment with IL-10).

In a further aspect the invention relates to a method of treating a mammal having circulating antibodies against IFNB 1a, such as Avonex™ or Rebif®, or 1b, such as Betaseron®, which method comprises administering a variant or conjugate of the invention which has a reduced or no reaction with said antibodies. The compound is administered in an effective amount. The mammal is preferably a human being. The mammals to be treated may suffer from any of the diseases listed above for which interferon β is a useful treatment. In particular, this aspect of the invention is of interest for the treatment of multiple sclerosis (any of the types listed above), hepatitis or cancer. Furthermore, the invention relates to a method of making a pharmaceutical product for use in treatment of mammals having circulating antibodies against interferon β 1a, such as Avonex™ or Rebif®, or 1b, such as Betaseron®, wherein a variant or conjugate of the present invention which has reduced reaction or no reaction with such circulation antibodies (e.g. the reaction is reduced by at least 25%, such as by at least 50%, and preferably by at least 75% such as about 100% (i.e. no reaction) is formulated into an injectable or otherwise suitable formulation as further described above. The term "circulating antibodies" is intended to indicate antibodies, in particular neutralizing antibodies, formed in a mammal in response to having been treated with any of the commercially available IFNB preparations (Rebif, Betaseron, Avonex).

In a further aspect the invention relates to a method of treating a patient in need of treatment with a pharmaceutical composition with at least some of the therapeutically beneficial properties of IFNB (e.g. a patient suffering from any of the diseases mentioned herein which is treatable by IFNB) comprising administering a composition comprising a variant or conjugate of the invention, said treatment having reduced or removed adverse psychological effects as compared to treatment with current commercial IFNB products. In a still further aspect the invention relates to a pharmaceutical composition useful for such treatment.

Also contemplated is use of a nucleotide sequence encoding a polypeptide variant or conjugate of the invention in gene therapy applications. In particular, it may be of interest to use a nucleotide sequence encoding a polypeptide as described in the section above entitled "Variants with increased glycosylation" or "Variants with specific amino acid substitutions" or "Variants which are fusion proteins". The glycosylation of the polypeptides is thus achieved during the course of the gene therapy, i.e. after expression of the nucleotide sequence in the human body.

Gene therapy applications contemplated include treatment of those diseases in which the polypeptide is expected to provide an effective therapy due to its antiviral activity, e.g., viral diseases, including hepatitis such as hepatitis C, and particularly HPV, or other infectious diseases that are responsive to IFNB or infectious agents sensitive to IFNB. Furthermore, the conjugate or polypeptide of the invention may be used in the treatment of chronic inflammatory demyelinating polyradiculoneuropathy, and of severe necrotising cutaneous lesions. Also, gene therapy in connection with the treatment of any MS type is contemplated. Similarly, this invention contemplates gene therapy applications for immunomodulation, as well as in the treatment of those diseases in which IFNB is expected to provide an effective therapy due to its antiproliferative activity, e.g., tumors and cancers, or other conditions characterized by undesired cell proliferation, such as restenosis. A further description of such gene therapy is provided in WO 95/25170.

Local delivery of IFNB using gene therapy may provide the therapeutic agent to the target area while avoiding potential toxicity problems associated with non-specific administration.

Both in vitro and in vivo gene therapy methodologies are contemplated.

Several methods for transferring potentially therapeutic genes to defined cell populations are known. For further reference see, e.g., Mulligan, "The Basic Science Of Gene Therapy", Science, 260, pp. 926–31 (1993). These methods include:

Direct gene transfer, e.g., as disclosed by Wolff et al., "Direct Gene transfer Into Mouse Muscle In vivo", Science 247, pp. 1465–68 (1990);

Liposome-mediated DNA transfer, e.g., as disclosed by Caplen et al., "Liposome-mediated CFTR Gene Transfer to the Nasal Epithelium Of Patients With Cystic Fibrosis" Nature Med., 3, pp. 39–46 (1995); Crystal, "The Gene As A Drug", Nature Med., 1, pp.-15–17 (1995); Gao and Huang, "A Novel Cationic Liposome Reagent For Efficient Transfection of Mammalian Cells", Biochem. Biophys Res. Comm., 179, pp. 280–85 (1991);

Retrovirus-mediated DNA transfer, e.g., as disclosed by Kay et al., "In vivo Gene Therapy of Hemophilia B: Sustained Partial Correction In Factor IX-Deficient Dogs", Science, 262, pp. 117–19 (1993); Anderson, "Human Gene Therapy", Science, 256, pp. 808–13(1992);

DNA Virus-mediated DNA transfer. Such DNA viruses include adenoviruses preferably Ad-2 or Ad-5 based vectors), herpes viruses (preferably herpes simplex virus based vectors), and parvoviruses (preferably "defective" or non-autonomous parvovirus based vectors, more preferably adeno-associated virus based vectors, most preferably AAV-2 based vectors). See, e.g., Ali et al., "The Use Of DNA Viruses as Vectors for Gene Therapy", Gene Therapy, 1, pp. 367–84 (1994); U.S. Pat. No. 4,797,368, and U.S. Pat. No. 5,139,941.

The invention is further described in the following examples. The examples should not, in any manner, be understood as limiting the generality of the present specification and claims.

EXAMPLES

Materials

HeLa cells—(available from American Type Culture Collection (ATCC)

ISRE-Luc (Stratagene, La Jolla USA)

pCDNA 3.1/hygro (Invitrogen, Carlsbad USA)

pGL3 basic vector (Promega)

Human genomic DNA (CloneTech, USA)

DMEM medium: Dulbecco's Modified Eagle Media (DMEM), 10% fetal bovine serum (available from Life Technologies A/S, Copenhagen, Denmark)

Assays

Interferon Assay Outline

It has previously been published that IFNB interacts with and activates Interferon type I receptors on HeLa cells. Consequently, transcription is activated at promoters containing an Interferon Stimulated Response Element (ISRE). It is thus possible to screen for agonists of interferon receptors by use of an ISRE coupled luciferase reporter gene (ISRE-luc) placed in HeLa cells.

Primary Assay

HeLa cells are co-transfected with ISRE-Luc and pCDNA 3.1/hygro and foci (cell clones) are created by selection in DMEM media containing Hygromycin B. Cell clones are screened for luciferase activity in the presence or absence of IFNB. Those clones showing the highest ratio of stimulated to unstimulated luciferase activity are used in further assays.

To screen muteins, 15,000 cells/well are seeded in 96 well culture plates and incubated overnight in DMEM media. The next day muteins as well as a known standard are added to the cells in various concentrations. The plates are incubated for 6 hours at 37° C. in a 5% $CO_2$ air atmosphere LucLite substrate (Packard Bioscience, Groningen The Netherlands) is subsequently added to each well. Plates are sealed and luminescence measured on a TopCount luminometer (Packard) in SPC (single photon counting) mode. Each individual plate contains wells incubated with IFNB as a stimulated control and other wells containing normal media as an unstimulated control. The ratio between stimulated and unstimulated luciferase activity serves as an internal standard for both mutein activity and experiment-to-experiment variation.

Secondary Assay

Currently, there are 18 non-allelic interferon α genes and one IFNB gene. These proteins exhibit overlapping activities and thus it is critical to ensure that muteins retain the selectivity and specificity of IFNB.

The β-R1 gene is activated by IFNB but not by other interferons. The transcription of β-R1 thus serves as a second marker of IFNB activation and is used to ensure that muteins retain IFNB activity. A 300 bp promoter fragment of β-R1 shown to drive interferon sensitive transcription (Rani, M. R., et al. (1996) JBC 271 22878–22884) was isolated by PCR from human genomic DNA and inserted into the pGL3 basic vector (Proniega). The resulting β-R1:luciferase gene is used in assays similar to the primary assay described above. In astrocytoma cells, the resulting β-R1:luciferase gene has been described to show 250-fold higher sensitivity to IFNB than to interferon α (Rani et al., op. cir.).

ELISA Assay

The concentration of IFNB is quantitated by use of a commercial sandwich immunoassay (PBL Biomedical Laboratories, New Brunswick, N.J., USA). The kit is based on an ELISA with monoclonal mouse anti-IFN-β antibodies for catching and detection of IFN-β in test samples. The detecting antibody is conjugated to biotin.

Tests samples and recombinant human IFN-β standard are added in 0.1 mL in concentrations from 10–0.25 ng/mL to microtiter plates, precoated with catching antibody. The plates are incubated at RT for 1 hr. Samples and standard are diluted in kit dilution buffer.

The plates are washed in the kit buffer and incubated with the biotinylated detecting antibody in 0.1 mL for 1 hr at RT. After another wash the streptavidin-horseradishperoxidase conjugate is added in 0.1 mL and incubated for 1 hr at RT.

The reaction is visualised by addition of 0.1 mL Tetramethylbenzidine (TMB) substrate chromogen. The plates are incubated for 15 minutes in the dark at RT and the reaction is stopped by addition of stop solution. The absorbance is read at 450 nm using an ELISA reader.

Receptor Binding Assay

The receptor binding capability of a polypeptide or conjugate of the invention can be determined using the assay described in WO 95/25170 entitled "Analysis Of IFN-β (Phe$_{101}$) For Receptor Binding" (which is based on Daudi or A549 cells). Soluble domains of IFNAR1 and IFNAR2 can be obtained essentially as described by Arduini et al., Protein Science, 1999, Vol. 8, pp. 1867–1877 or as described in Example 10 herein.

Alternatively, the receptor binding capability is determined using a crosslinking agent such as disuccinimidyl suberate (DSS) available from Pierce, Rockford, Ill., USA as follows:

The polypeptide or conjugate is incubated with soluble IFNAR-2 receptor in the presence or absence of DSS in accordance with the manufacturer's instructions. Samples are separated by SDS-PAGE, and a western blot using anti-IFNB or anti-IFNAR2 antibodies is performed. The presence of a functional IFNB polypeptide/conjugate: receptor interaction is apparent by an increase in the molecular size of receptor and IFNB in the presence of DSS.

Furthermore, a crosslinking assay using a polypeptide or conjugate of the invention and both receptor subunits (IFNAR-1 and IFNAR-2) can establish Interferon receptor 1 binding ability. In this connection it has been published that IFNAR-1 binds only after an interferon 1: IFNAR-2 complex is formed (Mogensen et al., Journal of Interferon and Cytokine Research, 19:1069–1098, 1999).

In Vitro Immunogenicity Tests of Interferon , β Conjugates

Reduced immunogenicity of a conjugate or polypeptide of the invention is determined by use of an ELISA method measuring the immunoreactivity of the conjugate or polypeptide relative to a reference molecule or preparation. The reference molecule or preparation is normally a recombinant human IFNB preparation such as Avonex, Rebif or Betaseron, or another recombinant human IFNB preparation produced by a method equivalent to the way these products are made. The ELISA method is based on antibodies from patients treated with one of these recombinant IFNB preparations. The immunogenicity is considered to be reduced when the conjugate or polypeptide of the invention has a statistically significant lower response in the assay than the reference molecule or preparation.

Another method of determining immunogenicity is by use of sera from patients treated with IFNB (i.e. any commercial IFNB product) in an analogous manner to that described by Ross et al. J. Clin Invest. 95, 1974–78, 1995. In the antiviral neutralisation bioassay reduced immunogenicity results in reduced inhibition of a conjugate of the invention by patient sera compared to a wt IFNB reference molecule. Furthermore, in the biochemical IFN binding assay a less immunogenic conjugate is expected to bind to patient IgG to a lesser extent than reference IFNB molecules.

For the neutralisation assay, the reference and conjugate molecules are added in a concentration that produces approximately 80% virus protection in the antiviral neutralisation bioassay. The IFNB proteins are mixed with patient sera in various dilutions (starting at 1:20).

Antiviral Activity

The antiviral bioassay is performed using A549 cells (CCL 185, American tissue culture collection) and Encephalomyocarditis (EMC) virus (VR-129B, American tissue culture collection).

The cells are seeded in 96 well tissue culture plates at a concentration of 10,000 cells/well and incubated at 37° C. in a 5% $CO_2$ air atmosphere. A polypeptide or conjugate of the invention is added in concentrations from 100–0.0001 IU/mL in a total of 100 μl DMEM medium containing fetal calf serum and antibiotics.

After 24 hours the medium is removed and 0.1 mL fresh medium containing EMC virus is added to each well. The EMC virus is added in a concentration that causes 100% cell death in IFN-β free cell cultures after 24 hours.

After another 24 hrs, the antiviral effect of the polypeptide or conjugate is measured using the WST-1 assay. 0.01 mL WST-1 (WST-1 cell proliferation agent, Roche Diagnostics GmbH, Mannheim, Germany) is added to 0.1 mL culture and incubated for ½–2 hours at 37° C. in a 5% $CO_2$ air atmosphere. The cleavage of the tetrazolium salt WST-1 by mitochondrial dehydrogenases in viable cells results in the formation of formazan that is quantified by measuring the absorbance at 450 nm.

Neutralisation of Activity in Interferon Stimulated Response Element (ISRE) Assay The IFNB neutralising effect of anti-IFNB sera are analysed using the ISRE-Luciferase activity assay.

Sera from IFNB treated patients or from immunised animals are used. Sera are added either in a fixed concentration (dilution 1:20–1:500 (pt sera) or 20–600 ng/mL (animal sera)) or in five-fold serial dilutions of sera starting at 1/20 (pt sera) or 600 ng/mL (animal sera). IFNB is added either in five fold-dilutions starting at 25.000 IU/mL or in a fixed concentration (0.1–10 IU/mL) in a total volume of 80 μl DMEM medium+10% FCS. The sera are incubated for 1 hr. at 37° C. with IFN-β.

The samples are then transferred to 96 well tissue culture plates containing HeLa cells transfected with ISRE-Luc grown from 24 hrs before (15,000 cells/well) in DMEM media. The cultures are incubated for 6 hours at 37° C. in a 5% $CO_2$ air atmosphere. LucLite substrate (Packard Bioscience, Groningen, The Netherlands) is subsequently added to each well. Plates are sealed and luminescence measured on a TopCount luminometer (Packard) in SPC (single photon counting) mode.

When IFNB samples are titrated in the presence of a fixed amount of serum, the neutralising effect was defined as fold inhibition (FI) quantified as EC50(w. serum)/EC50 (w/o serum). The reduction of antibody neutralisation of IFNB variant proteins is defined as $$\left(1 - \frac{FI\ variant}{FI\ wt}\right) \times 100\%$$

Biological Half-life Measurement of a PEG-IFNB Conjugate or Glycosylated IFNB Variants Measurement of biological half-life can be carried out in a number of ways described in the literature. One method is described by Munafo er al. (European Journal of Neurology 1998, Vol. 5. No. 2, pp. 187–193), who used an ELISA method to detect serum levels of IFNB after subcutaneous and intramuscular administration of IFNB.

The rapid decrease of IFNB serum concentrations after i.v administration has made it important to evaluate biological responses to IFNB treatment. However it is contemplated that the conjugates of the present invention will have prolonged serum half lives also after i.v. administration making it possible to measure by e.g. an ELISA method or by the primary screening assay.

Different pharmacodynamic markers (e.g. serum neupterin and beta2 microglobulin) have also been studied (Clin Drug Invest (1999) 18(1):27–34). These can equally well be used to evaluate prolonged biological effect. These experiments may also be carried out in suitable animal species, e.g. rats.

Assays to assess the biological effects of IFNB such as antiviral, antiproliferative and immunomodulatory effects (as described in e.g. Annals of Neurology, Vol. 37, No. 1, pp. 7–15) can be used together with the primary and secondary screening assays described herein to evaluate the biological efficacy of the conjugate in comparison to wild type IFNB.

Finally an animal model such as the commonly used experimental autoimmune encephalomyelitis (EAE) model can be used to establish efficacy of a conjugate or polypeptide of the invention. In the EAE model immunization with myelin or myelin derived proteins elicits a disease mimicking the majority of the inflammatory and neurologic features of multiple sclerosis in humans. EAE has been used in mice, rats, rabbits, and marmosets (Cannella et al. PNAS, 95, 10100–5, 1998, Zaprianova et al. Morfologiia, 112, 25–8, 1997, Hassouna et al. J. Urology, 130, 806–10, 1983, Genain & Hauser J. Mol. Med. 75, 187–97,1997). Other models include Theiler's murine encephalomyelitis virus (TMEV) model (Murray et al. J. Neurosci. 18, 7306–14, 1998), will be used to establish efficacy of the IFNB conjugate.

PEGylation in Microtiter Plates of a Tagged Polypeptide with Interferon β Activity The Method Comprises Expressing the interferon β polypeptide with a suitable tag, e.g. any of the tags exemplified in the general description above.

Transferring culture broth to one or more wells in a microtiter plate capable of immunobilising the tagged polypeptide. When the tag is His-His-His-His-His-His (Casey et al., J. Immunol. Meth. 179, 105 (1995)), a Ni-NTA HisSorb microtiter plate commercially available from QiaGen can be used.

After allowing for immobilising the tagged polypeptide to the microtiter plate, the wells are washed in a buffer suitable for binding and subsequent PEGylation.

Incubating the wells with the activated PEG of choice. As an example, M-SPA-5000 from Shearwater Polymers is used. The molar ratio of activated PEG to polypeptide has to be optimised, but will typically be greater than 10:1 more typically greater than 100:1.

After a suitable reaction time at ambient temperature, typically around 1 hour, the reaction is stopped by removal of the activated PEG solution. The conjugated protein is eluted from the plate by incubation with a suitable buffer. Suitable elution buffers may contain Imidazole, excess NTA or another chelating compound.

The conjugated protein is assayed for biological activity and immunogenicity as appropriate.

This tag may optionally be cleaved off using a method known in the art, e.g. using diaminopeptidase and the Gln in pos −1 will be converted to pyroglutamyl with GCT (glutamylcyclotransferase) and finally cleaved off with PGAP (pyro-glutamyl-aminopeptidase) giving the native protein. The process involves several steps of metal chelate affinity chromatography. Alternatively, the tagged polypeptide may be conjugated.

PEGylation of a Receptor-bound Interferon β Polypeptide

In order to optimize PEGylation of an interferon β polypeptide in a manner excluding PEGylation of lysines involved in receptor recognition, the following method has been developed:

The soluble domains of IFNAR1 and IFNAR2 are obtained essentially as described in Arduini et al., Protein Science (1999), Vol. 8: 1867–1877 or as described in Example 10.

A ternary complex consisting of an interferon β polypeptide, a soluble domain of IFNAR1 and a soluble domain of IFNAR2 in a 1:1:1 stoichiometry is formed in a PBS buffer at pH 7–9. The concentration of Interferon β polypeptide is approximately 20 ug/ml or 1 uM and the receptors are present at equimolar concentration.

M-SPA-5000 from Shearwater Polymers, Inc is added at 3 different concentration levels corresponding to 5, 20 or 100 molar excess of interferon β polypeptide. The reaction time is 30 min at RT. After the 30 min reaction period, the pH of the reaction mixture is adjusted to pH 2.0 and the reaction mixture is applied to a Vydac C18 column and eluted with an acetonitrile gradient essentially as described (Utsumi et al., J. Biochem., Vol. 101, pp. 1199–1208, (1987). Alternatively and more elegantly, an isopropanol gradient can be used.

Fractions are analyzed using the primary screening assay described herein and active PEGylated interferon-β polypeptide obtained by this method stored at −80° C. in PBS, pH 7 containing 1 mg/ml HSA.

Alternatively, to the procedure described above a soluble domain of IFNAR2 is used as the only receptor component to form a binary complex. Furthermore, IFNAR2 may be immobilized on a suitable resin (e.g. Epoxy activated Sepharose 6B) according to the manufactures instructions prior to forming the binary complex. After PEGylation, the PEGylated Interferon-β is eluted with a 0.1 M Glycin, pH 2 buffer and activity measured as described after pH adjustment to neutral.

Accessible Surface Area (ASA)

The computer program Access (B. Lee and F. M. Richards, J. Mol. Biol. 55: 379–400 (1971)) version 2 (Copyright (c) 1983 Yale University) is used to compute the accessible surface area (ASA) of the individual atoms in the structure. This method typically uses a probe-size of 1.4 Å and defines the Accessible Surface Area (ASA) as the area formed by the centre of the probe. Prior to this calculation all water molecules and all hydrogen atoms are removed from the coordinate set, as are other atoms not directly related to the protein. Alternative programs are available for computing ASA. e.g. the program WhatIf G. Vriend, J. Mol. Graph. (1990) 8, 52–5 6, electronically available at the WWW website at swift.emblheidelberg.de/servers2/ (R. Rodriguez et al., CABIOS (1998) 14:523–528) using the option Accessibility to calculate the accessible molecular surface.

Fractional ASA of Side Chain

The fractional ASA of the side chain atoms is computed by division of the sum of the ASA of the atoms in the side chain with a value representing the ASA of the side chain atoms of that residue type in an extended ALA-x-ALA tripeptide. See Hubbard, Campbell & Thornton (1991) J. Mol. Biol. 220, 507–530. For this example the CA atom is regarded as a part of the side chain of Glycine residues but not for the remaining residues. The following table indicates the 100% ASA standard for the side chain:

| | |
|---|---|
| Ala | 69.23 Å$^2$ |
| Arg | 200.35 Å$^2$ |
| Asn | 106.25 Å$^2$ |
| Asp | 102.06 Å$^2$ |
| Cys | 96.69 Å$^2$ |
| Gln | 140.58 Å$^2$ |
| Glu | 134.61 Å$^2$ |
| Gly | 32.28 Å$^2$ |
| His | 147.00 Å$^2$ |
| Ile | 137.91 Å$^2$ |
| Leu | 140.76 Å$^2$ |
| Lys | 162.50 Å$^2$ |
| Met | 156.08 Å$^2$ |
| Phe | 163.90 Å$^2$ |
| Pro | 119.65 Å$^2$ |
| Ser | 78.16 Å$^2$ |
| Thr | 101.67 Å$^2$ |
| Trp | 210.89 Å$^2$ |
| Tyr | 176.61 Å$^2$ |
| Val | 114.14 Å$^2$ |

Determining Surface Exposed Amino Acid Residues

The three-dimensional crystal structure of human IFNB at 2.2 Å resolution (Karpusas et al. Proc. Nat. Acad. Sci. USA (1997) 94:11813–11818 is available from the Protein Data Bank (PDB) (Bernstein et al. J. Mol. Biol. (1977) 112 pp. 535) and electronically available via The Research Collaboratory for Structural Bioinformatics PDB at the www website at pdb.org under accession code 1AU1. This crystal structure contain two independent molecules of human IFNB in this example the A molecule is used.

Surface Exposure

Using the WhatIf program as described above the following residues were found to have zero surface accessibility for their side chain atoms (for Gly the accessibility of the CA atom is used): G7, N14, C17, L21, I44, A55, A56, T58, I59, M62, L63, L98, L122, Y125, I129, L133, A142, W143, V146, I150, N153, I157, L160, T161, and L164.

Fractional Surface Exposure

For further analysis it was necessary to remodel the side chains of residues R71, R113, K115, L116, M117 due to steric clashes. The remodelling was done using Modeler 98, MSI INC. Performing fractional ASA calculations using the Access computer program on the remodelled IFNB molecule (only including the amino acid residues and excluding the N-linked sugar moiety) resulted in the following residues having more than 25% of their side chain exposed to the surface: S2, N4, L5, F8, L9, R11, S12, F15, Q16 Q18, K19, W22, Q23, G26, R27, L28, E29, Y30, L32, K33, R35, M36, N37, D39, E42, K45, Q46, L47, Q48, Q49, Q51, K52, Q64, A68, R71, Q72, D73, S75, S76, G78, N80, E81, T82, E85, N86, A89, Y92, H93, N96, H97, K99, T100, E103, E104, K105, E107, K108, E109, D110, F111, R113, G114, K115, L116, S119, L120, H121, K123, R124, G127, R128, L130, H131, K134, A135, K136, E137, Y138, S139, H140, V148, R152, Y155, N158, G162, Y163, R165, and N166, and the following residues have more than 50% of their side chain exposed to the surface: N4, L5, F8, S12, F15, Q16, K19, W22, G26, R27, E29, Y30, K33, R35, N37, D39, E42, Q46, Q48, Q49, Q51, K52, R71, D73, S75, G78, N80, E81, T82, E85, N86, A89, Y92, H93, K99, T100, E103, E104, E107, K108, D110, F111, L116, K123, R124, G127, H131, K134, E137, V148, Y155, R165, and N166.

Example 1

Design of an Expression Cassette for Expression of IFNB in Mammalian and Insect Cells The DNA sequence, GenBank accession number M28622 (shown in SEQ ID NO:1), encompassing a full length cDNA encoding human IFNB with its native signal peptide, was modified in order to facilitate high expression in mammalian cells. First the ATG start codon context was modified according to the Kozak consensus sequence (Kozak, M. *J Mol Biol* 1987 Aug. 20;196(4):947–50), such that there is a perfect match to the consensus sequence upstream of the ATG start codon. Secondly the codons of the native human IFNB was modified by making a bias in the codon usage towards the codons frequently used in highly expressed human genes. Subsequently, certain nucleotides in the sequence were substituted with others in order to introduce recognition sites for DNA restriction endonucleases (this allows for easier modification of the DNA sequence later). Primers were designed such that the gene could be synthesised:

```
CBProFpr1:
5'-GGCTA GCGTT TAAAC TTAAG CTTCG CCACC ATGAC CAACA AGTGC    (SEQ ID NO:3)
CTGCT CCAGA TCGCC CTGCT CCTGT-3',

CBProFpr2:
5'-ACAAC CTGCT CGGCT TCCTG CAGAG GAGTT CGAAC TTCCA GTGCC    (SEQ ID NO:4)
AGAAG CTCCT GTGGC AGCTG AACGG-3',

CBProFpr3.
5'-GAACT TCGAC ATCCC CGAGG AAATC AAGCA GCTGC AGCAG TTCCA    (SEQ ID NO:5)
GAAGG AGGAC GCCGC TCTGA CCATC-3',
```

-continued

CBProFpr4.
5'-TTCCG CCAGG ACTCC AGCTC CACCG GTTGG AACGA           (SEQ ID NO:6)
GACCATCGTGGAGAACCTGCTGGCCAACGTGTACC-3',

CBProFpr5.
5'-AGGAG AAGCT GGAGA AGGAG GACTT CACCC GCGGC AAGCT     (SEQ ID NO:7)
GATGA GCTCC CTGCA CCTGA AGCGC TACTA-3',

CBProFpr6.
5'-GGAGT ACAGC CACTG CGCCT GGACC ATCGT ACGCG TGGAG ATCCT   (SEQ ID NO:8)
GCGCA ACTTC TACTT CATCA ACCGC-3',

CBProFpr9:
5'-CACCA CACTG GACTA GTGGA TCCTT ATCAG TTGCG CAGGT AGCCG   (SEQ ID NO:9)
GTCAG GCGGT TGATG AAGTA GAAGT-3',

CBProFpr10:
5'-AGGCG CAGTG GCTGT ACTCC TTGGC CTTCA GGTAG TGCAG GATGC   (SEQ ID NO:10)
GGCCA TAGTA GCGCT TCAGG TGCAG-3',

CBProFpr11:
5'-CTCCT TCTCC AGCTT CTCCT CCAGC ACGGT CTTCA GGTGG TTGAT   (SEQ ID NO:11)
CTGGT GGTAC ACGTT GGCCA GCAGG-3',

CBProFpr12:
5'-GAGCT GGAGT CCTGG CGGAA GATGG CGAAG ATGTT CTGCA GCATC   (SEQ ID NO:12)
TCGTA GATGG TCAGA GCGGC GTCCT-3',

CBProFpr13:
5'-CCTCG GGGAT GTCGA AGTTC ATCCT GTCCT TCAGG CAGTA CTCCA   (SEQ ID NO:13)
GGCGCCCGTTCAGCTGCCACAGGAG-3',

CBProFpr14:
5'CAGGAAGCCGAGCAGGTTGTAGCTCATCGATAGGGCCGTGGTGCTGAA       (SEQ ID NO:14)
GCACAGGAGCAGGGCGATCTGG-3',

The primers were assembled to the synthetic gene by one step PCR using Platinum Pfx-polymerase kit (Life Technologies) and standard three step PCR cycling parameters. The assembled gene was amplified by PCR using the same conditions.

A cDNA encoding a N-terminal extended form of human IFNB was synthesised using the same PCR conditions as described above but with the primers CBProFpr1 and -14 substituted with the primers:

CBProFpr7
5'CTGCTCCAGATCGCCCTGCTCCTGTGCTTCAGCACCACGGCCCTATCGAT     (SEQ ID NO:15)
GAAGCACCAGCACCAGCATC-3',

CBProFpr8
5'CACTGCTTACTGGCTTATCGAAATTAATACGACTCACTATAGGGAGACC      (SEQ ID NO:16)
CAAGCTGGCTAGCGTTTAAAC-3',

CBProFpr15
5'CAGGAAGCCGAGCAGGTTGTAGCTCATCTGTTGGTGTTGATGTTGGTGC      (SEQ ID NO:17)
TGATGCTGGTGCTGGTGCTTC-3',

CBProFpr16
5'AGCAGGGCGATCTGGAGCAGGCACTTGTTGGTCATGGTGGCGAAGCTTA      (SEQ ID NO:18)
AGTTTAAACGCTAGCCAGCTT-3', in order to incorporate a purification TAG in the IFNB molecule.

The synthesised genes were cloned into pCDNA3.1/Hygro (Invitrogen) between the HindIII site at the 5' end and the BamHI at the 3', resulting in pCBProF1 and pCBProF2.

The synthetic intron from pCI-Neo (Promega) was amplified using standard PCR conditions as described above and the primers:

CBProFpr37  5'-CCGTCAGATCCTAGGCTAGCTTATTGCGGTAGTTTATCAC-3' (SEQ ID NO:19),

CBProFpr38  5'-GAGCTCGGTACCAAGCTTTTAAGAGCTGTAAT-3' (SEQ ID NO:20), resulting in a 332 bp PCR fragment which was cut with NheI and HindIII and inserted in the 5'UTR of the plasmids pCBProF1 and pCBProF2 resulting in pCBProF4 and pCBProF5.

Codons for individual amino acids were changed by amplifying relevant regions of the coding region by PCR in such a way that the PCR introduced changes in the sequence can be introduced in the expression plasmids by classical cloning techniques. E.g. the primers:

Lys45arg-5'primer (NarI/KasI): 5'GCTGAACGGGCGCCTGGAGTACTGCCTGAAGGACAGGATGAACTTCGA CATCCCCGAGGAAATCCGCCAGCTGCAGC-3' (SEQ ID NO:21), Lys45mut-3'primer (BsiWI): 5'TCTCCACGCGTACGATG-GTCCAGGCGCAGTGGCTG-3' (SEQ ID NO:22), were used to introduce a K45R substitution in the PCR-fragment spanning the region from position 1055 to 1243 in pCBProF1. Both the PCR fragment and pCBProF1 was cut with NarI and BsiWI which are both unique. The PCR fragment and the vector backbone of pCBProF1 are purified and ligated resulting in substitution of the Lys45 codon AAG with the Arg codon CGC in pCBProF1.

Furthermore, SOE (sequence overhang extension) PCR was used for introduction of amino acid substitutions. In the SOE-PCR both the N-terminal part and the C-terminal part of the IFNB molecule were first amplified in individual primary PCRs.

For these primary PCRs the central complementary primers were synthesised such that the codon(s) for the amino acid(s) to be substituted is/are changed to the desired codon (s). The terminal primers were standard primers defining the N- and C-terminal of the IFNβ molecule respectively. Further the terminal primers provided a restriction enzyme site enabling subsequent cloning of the full-length PCR product. Thus, the central (nonsense) primer and the N-terminal (sense) primer were used to amplify the N-terminal part of the IFNβ coding region in one of the primary PCRs and equivalently for the C-terminal part. Once amplified the N- and C-terminal parts are assembled into the full-length product in a secondary PCR and cloned into a modified version of pCDNA3.1/Hygro as described above. For instance, the following primers were used to introduce the mutations for the substitutions F111N and R113T:

```
CBProFprimer9(Sense):
CACCACACTGGACTAGTGGATCCTTATCAGTTGCGCAGGTAGCCGGTCAGGCGGTTG (SEQ ID NO:23)
ATGAAGTAGAAGT, CBFroFprimer231 (Antisense):
CATCAGCTTGCCGGTGGTGTTGTCCTCCTTC                           (SEQ ID NO:24), CBProFprimer230 (Sense):
GAAGGAGGACAACACCACCGGCAAGCTGATG                           (SEQ ID NO:25), CBProFprimer42 (Antisense):
CACACTGGACTAGTAAGCTTTTATCAGTTGCGCAGGTAGC                  (SEQ ID NO:26),
```

Furthermore, in cases where the introduced mutation(s) were sufficiently close to a unique restriction endo-nuclease site in the expression plasmid variant genes were constructed using construction procedure encompassing a single PCR step and a subsequent cloning. For instance, the substitution K19R was introduced by use of the PCR primer: CBProFpr58: GAGGAGTTCGAACTTCCAGTGC-CAGCGCCTCCTGTGGCAGCTGAACG (SEQ ID NO:27), and CBProFprimer9 (SEQ ID NO:23, above).

The PCR product was subsequently cloned using the restriction endo-nuclease sites BsiWI and BstBI.

Example 2

Expression of Human Interferon β in a Baculovirus/insect Cell System

In order to express the synthetic gene, encoding human interferon β harboured in pCBProF 1 (described in Example 1) in the baculovirus/insect cell system the gene was excised with NheI and XhoI and ligated into the transfer vector pBlueBac 4.5, which is included in the MaxBac 2.0 Transfection kit obtained from Invitrogen (San Diego, USA). All methods used for generation of recombinant baculovirus and expression in insect cells are described in the "MaxBac 2.0 Transfection and Expression Manual" included in the kit.

In brief, together with liniarized AcMNPV DNA (Bac-N-Blue DNA) pBlueBac 4.5-interferon β CBProF1) was transfected into SF9 cells. 3 days post-transfection the transfection supernatant was harvested and a plaque assay with appropriate viral dilutions was prepared. Blue distinct plaques were visible after 7 days and 6 individual plaques were collected for propagation in a 6-well plate. After 5 days 2 ml virus supernatant (P-1 stock) was harvested from each well. 0.75 ml was taken out from the P1 stocks and viral genomic DNA was isolated. The viral genomic DNA's were analysed in PCR reactions with forward/reverse primers in order to be able to select the recombinant baculoviruses among the six P-1 stocks. A small aliquot from the recombinant P-1 stock was tested in a human interferon β specific ELISA (available from PBL Biomedical Laboratories) in order to ensure that recombinant human interferon β was present in the supernatant.

For further propagation of chosen recombinant baculovirus $6\times10^6$ SF9 cells were seeded in a T-80 culture flask and infected with 200 μl of the P-1 stock. After 5 days the supernatant (P-2 stock) was harvested and 2 ml of the P-2 stock was used to infect a 100 ml suspension culture ($1\times10^6$ SF9 cells/ml) in a 500 ml Erlenmeyer flask (Corning). After 5 days the supernatant (P-3 stock) was harvested and the virus titer was determined by plaque assay.

In order to produce human interferon β for purification $1\times10^9$ SF9 cells were harvested from a backup suspension culture. In a 50 ml screw-cap tube the SF9 cells were infected with recombinant baculovirus from the P-3 stock (MOI=2) in a period of 15 minutes. Hereafter the cells were spun down and washed one time in serum-free medium (Sf-900 II SFM, Gibco BRL) and transferred to a 2800 ml Triple Baffle Fernbach Flask (Bellco) containing 1 l serum-free medium. 3 days post-infection the medium supernatant was harvested and the recombinant human interferon β was purified.

Purification of Interferon β Molecules

The fermentation broth is concentrated and/or pH adjusted to approximately 4.5 after dilution to suitable ionic strength. Suitable is intended to mean that the ionic strength is so low that interferon β will bind to a Mono S cation exchange column (Pharmacia) equilibrated in 4 mM acetic acid pH 4.5 (buffer A). After application, the column is washed with 3 column volumes buffer A and interferon β is eluted with a linear gradient from buffer A to buffer A including 1 M NaCl. Alternatively purification can be obtained as described for Interferon α (Analytical Biochemistry 247, 434–440 (1997) using a TSK-gel SP-5PW column (Toso Haas)).

Alternatively His tagged interferon β can be purified using IMAC (Immobilized Metal Affinity Chromatography) in accordance with well known methods, e.g., as described by UniZyme Laboratories, Denmark.

Another purification method makes use of monoclonal or polyclonal antibodies. Interferon β fermentation broth is adjusted to pH 7 and 0.5 M NaCl and applied to a column with immobilized monoclonal antibody to recombinant human interferon β. The column is equilibrated with e.g. 10 mM Tris, 0.5 M NaCl, pH 7 (Buffer B) prior to application. After application the column is washed with 3 column volumes Buffer B and eluted with a suitable buffer at low pH (e.g. pH 2–3).

Alternatively, if the interferon β is tagged with e.g. the c-Myc peptide (EQKLI SEEDL, SEQ ID NO:53), monoclonal antibodies raised against the c-Myc peptide, can be used in a similar fashion. Immobilization of antibody to the column is achieved using e.g. CNBr-Sepharose (Pharmacia) according to the manufacturers instructions.

A combination of Cation exchange chromatography, IMAC and/or antibody chromatography may be applied if necessary to obtain relevant purity for further experiments.

Purity, identity, quantity and activity of eluted fractions from the abovementioned columns can be determined using a combination of methods known by the person skilled in the art. These may include one or more of the following assays and methods or other relevant methods known by the person skilled in the art: the primary and secondary assays described above, ELISA methods, SDS-PAGE, western blotting, IEF, HPLC, amino acid sequencing, mass spectrometry and amino acid analysis.

Following purification, the modified interferon β polypeptide may be subjected to conjugation to a polymer molecule such as M-SPA-5000 from Shearwater Polymers according to the manufacturer's instructions. Preferably, the receptor recognition site of the purified modified interferon β polypeptide is blocked prior to conjugation as described in the Materials and Methods section herein.

Example 3

Expression of Human Interferon β in HEK293 Cells

In order to express the synthetic gene, encoding human interferon β, harboured by pCBProF1 (described in example 1), in HEK293 cells (ATCC Cat. No. CRL-1573) the gene was PCR-amplified with the two primers PBR7 (5'-CGCG-GATCCATATGACCAACAAGTGCCTG-3'; SEQ ID NO:28) and PBR2 (5'-CGCGGATCCTTATCAGTTGCG-CAG-3'; SEQ ID NO:29) and cloned into the BamHI site of pCDNA3.1 (−) (Invitrogen, USA) in correct orientation, giving the plasmid pPR9.

For transfection of the HEK293 cell line a T-25 culture flask was seeded to 50% confluency in DMEM medium (Life Technologies, USA) containing 10% FBS and incubated over night. By usage of FuGENE 6 Transfection Reagent (Roche, USA) pPR9 was transfected into the cells: To 95 μl serum-free DMEM medium was added 5 μl FuGENE 6 and 1.7 μl (2 μg) pPR9 and incubated at room temperature for 20 minutes. The transfection complex was then added drop-wise to the cells and the culture flask was returned to the incubator. Next day the cells were trypsinized and seeded into a T-80 culture flask in DMEM medium containing 10% FBS and 500 μg Geneticin (Life Technologies) per ml.

At confluency it was confirmed, by usage of a human interferon β specific ELISA, that the primary transfection-pool was expressing the wished protein and the cells were sub-cloned by limited dilution. In this way a high-producing HEK293 clone was identified expressing human interferon β.

Example 4

High Level Expression of Interferon β in CHO Cells

The cell line CHO K1 [p22]-E4 (ATCC # CCL-61) stably expressing human interferon β was passed 1:10 from a confluent culture and propagated as adherent cells in T-25 flasks in serum containing medium (MEMα w/ribonucleotides and deoxyribonucleotides (Gibco/BRL Cat # 32571), 10% FCS (Gibco/BRL Cat # 10091), penicillin arid streptomycin (Gibco/BRL Cat # 15140–114) until confluence. The media was then changed to serum free media (RenCyte CHO; MediCult Cat.# 22600140) for 24 hours before including 5 mM Sodium Butyrate (Merck Cat # 8.17500) during a medium change. The cells were then allowed to express interferon β for 48 hours prior to harvest of the medium. The interferon β concentration in the duplicate cultures was determined to be 854,797 IU/ml (with lower and upper 95% confidence interval at 711,134 IU/ml and 1,032,012 IU/ml) respectively).

In a separate set of experiments, the cell line CHO K1 [p22]-E4 stably expressing human interferon β was passed 1:10 from a confluent culture and propagated as adherent cells in serum containing medium (MEMα: w/ribonucleotides and deoxyribonucleotides (Gibco/BRL Cat #32571), 10% FCS (Gibco/BRL Cat # 10091), penicillin and streptomycin (Gibco/BRL Cat # 15140-114) until confluence in a 10 layer cell factory (NUNC #165250). The media was then changed to serum free media; DMEM/F12 (Gibco/BRL # 11039–021) with the addition of 1:100 ITS-A (Gibco/BRL # 51300-044) and 1:500 EX-CYTE VLE (Serological Proteins Inc. # 81-129-1) and 1:100 penicillin and streptomycin (Gibco/BRL Cat # 15140-114) for 48 hours before changing the medium with the further addition of 5 mM butyrate (Merck Cat # 8.17500). The cells were then allowed to express interferon β for 48 hours prior to harvest of the medium. The interferon β concentration was determined to be 824,791 IU/ml (with lower and upper 95% confidence interval at 610,956 IU/ml and 1,099,722 IU/ml) respectively).

It is contemplated that interferon β polypeptides of the invention may be produced in equally high yields in the same manner as any of those described above.

Example 5

Construction and Expression of IFNB Variant with One Introduced Alycosylation Site In order to insert an extra N-linked glycosylation site at position 111 in hIFN-β, the synthetic gene (hIFN-β) encoding hIFN-β (described in Example 1) was altered by site-directed PCR mutagenesis. Using BIO-X-ACT (Bioline, UK) and the plasmid PF050 [hifn-β)/pcDNA3.1(−)Hygro/Intron (a derivative of pCDNA3.1(−)Hygro (Invitrogen, USA) in which a chimeric intron obtained from pCI-neo (Promega, USA) had been inserted between the BamHI and NheI sites in the MCS of the vector] as template, two PCR reactions were performed with two overlapping primer-sets

[CB41 (5'-TTTAA ACTGG ATCCA GCCAC CATGA CCAAC AAG-3'; SEQ ID NO:30)/CB55 (5'-CGGCC ATAGT AGCGC TTCAG GTGCA GGGAG CTCAT CAGCT TGCCG GTGGT GTTGT CCTCC TTC-3'; SEQ ID NO:31) and CB42 (SEQ ID NO:26, above)/CB86 (5'-GAAGG AGGAC AACAC CACCG GCAAG CTGAT GAGCT CCCTG CACCT GAAGC GCTAC TATGG CCG-3'; SEQ ID NO:32) resulting in two fragments of 446 and 184 base pairs, respectively. These two fragments were assembled in a third PCR with the flanking primers CB41 and CB42. The resulting gene was inserted into the mammalian expression vector pCDNA3.1 (–)Hygro/Intron and confirmed by DNA sequencing to have the correct base changes leading to the substitutions F111N and R113T in hIFN-β (plasmid designated PF085).

To test the activity of the [F111N+R113T]hIFN-β variant, PF085 was transfected into the CHO K1 cell line (ATCC #CCL-61) by use of Lipofectamine 2000 (Life Technologies, USA) as transfection agent. 24 hours later the culture medium was harvested and assayed for IFN-β activity/concentration:

| | |
|---|---|
| Activity: | 56046 IU/ml [primary assay] |
| ELISA: | 80 ng/ml |
| Specific activity: | $7 \times 10^8$ IU/mg |

As seen, the [F111N+R113T]hIFN-β variant has a very high specific activity, about twice the specific activity of wt hIFN-β.

Example 6

Construction and Expression of IFNB with Another Introduced Glvcosylation Site [Q49N+Q51T]

Analogously to what is described in Example 5 an extra N-linked glycosylation site was introduced in position 49 by means of the substitutions Q49N and Q51T. Using PF043 (hIFN-β/pcDNA3.1 (Invitrogen, USA)) as template, two PCR reactions were performed with two overlapping primer-sets PBR7 (SEQ ID NO:28, above)/PBR78 (5'-GGCGT CCTCC TTGGT GAAGT TCTGC AGCTG-3'; SEQ ID NO:33) and PBR8 (5'-ATATA TCCCA AGCTT TTATC AGTTG CGCAG GTAGC CGGT-3'; SEQ ID NO:34)/PBR77 (5'-CAGCT GCAGA ACTTC ACCAA GGAGG ACGCC-3'; SEQ ID NO:35) resulting in two fragments of 228 and 369 base pairs, respectively. These two fragments were assembled in a third PCR with the flanking primers PBR7 and PBR8. The resulting gene was inserted into the mammalian expression vector pcDNA3.1(−)Hygro/Intron and confirmed by DNA sequencing to have the correct base changes leading to [Q49N,Q51T]hIFN-β (plasmid designated PF104).

To test the activity of the [Q49N+Q51T]hIFN-β variant, PF104 was transfected into the CHO K1 cell line by use of Lipofectamine 2000 (Life Technologies, USA) as transfection agent. 24 hours later the culture medium was harvested and assayed for IFN-β activity/concentration:

| | |
|---|---|
| Activity: | 17639 IU/ml [primary assay] |
| ELISA: | 10 ng/ml |
| Specific activity: | $1.7 \times 10^9$ IU/mg |

As observed here the [Q49N+Q51T]hIFN-β variant has a high specific activity. This may be due to poor recognition by one of the monoclonal antibodies used in the ELISA.

Example 7

Construction and Expression of IFNB with Two Introduced Glycosylation Sites

The additional glycosylation sites described in Examples 5 and 6 were introduced into human IFNB by means of the substitutions Q49N, Q51T, F111N, and R113T.

Using PF085 (described in Example 5) as template, two PCR reactions were performed with two overlapping primer-sets [PBR89 (5'CGCGG ATCCA GCCAC CATGA CCAAC AAGTG CCTG; SEQ ID NO:36)/PBR78 (SEQ ID NO:33) and PBR8 (SEQ ID NO:34)/PBR77 (SEQ ID NO:35)] resulting in two fragments of 228 and 369 base pairs, respectively.

These two fragments were assembled in a third PCR with the flanking primers PBR89 and PBR8. The resulting gene was inserted into the mammalian expression vector pCDNA3.1(−)Hygro/Intron and confirmed by sequencing to have the correct base changes leading to [Q49N, Q51T, F111N, R113T] hIFN-β (plasmid designated PF123).

PF123 was transfected into CHO K1 cells by use of Fugene 6 (Roche) as transfection agent. 24 hours later the culture medium was harvested and assayed for IFN-β activity/concentration:

| | |
|---|---|
| Activity: | 29401 IU/ml [primary assay] |
| ELISA: | 14 ng/ml |
| Specific activity: | $2.1 \times 10^9$ IU/ml |

As observed here the [Q49N+Q51T+F111N+R113T] hIFN-β variant also has a high specific activity.

The variant was found to have receptor binding activity in the receptor binding assay described in the Materials and Methods section, which is based on the use of the crosslinking agent DSS.

Example 8

Production of [Q49N+Q51T+F111N+R113T]IFNB Glycosylation Variant in Roller Bottles A CHOK1 sub-clone (5/G-10) producing the [Q49N+Q51T+F111N+R113T] glycosylation variant was seeded into 2 roller bottles, each with an expanded surface of 1700 $cm^2$ (Corning, USA), in 200 ml DMEM/F-12 medium (LifeTechnologies; Cat. # 31330) supplemented with 10% FBS and penicillin/streptomycin (P/S). After 2 days the medium was exchanged. After another 2 days the two roller bottles were nearly 100% confluent and the medium was shifted to 300 ml serum-free UltraCHO medium (BioWhittaker; Cat. # 12-724) supplemented with 1/500 EX-CYTE (Serologicals Proteins; Cat. # 81129N) and P/S. Growing the cells in this medium promotes a higher cell mass, higher than can be achieved in the serum containing medium. After 2 days the medium was renewed. After another 2 days the medium was shifted to the production medium: DMEM/F-12 medium (Life Technologies; Cat. # 21041) supplemented with 1/100 ITSA (Life Technologies; Cat. # 51300-044) [ITSA stands for Insulin (1.0 g/L)—Transferrin (0.55 g/L)—Selenium (0.67 mg/L) supplement for Adherent cultures],

Figure 3:
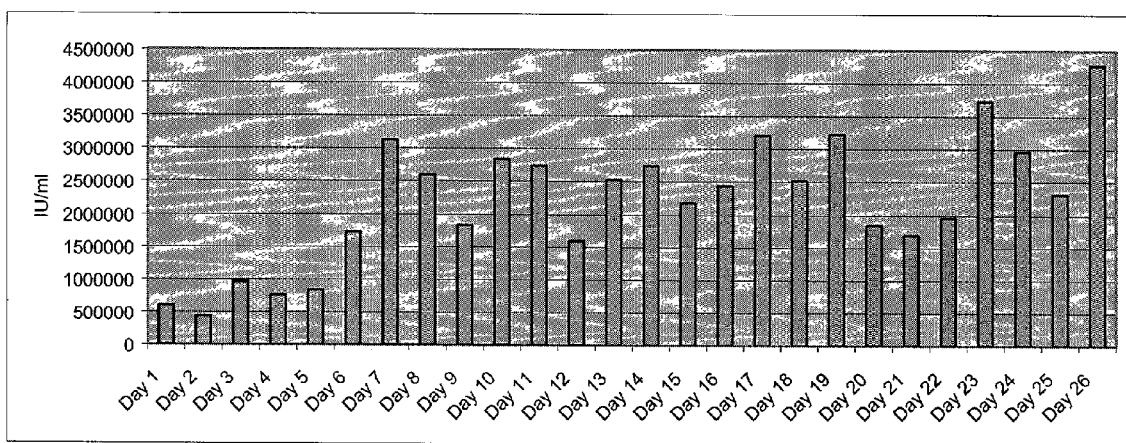
FIG. 3 illustrates the yield of interferon β production obtained according to Example 8.

1/500 EC-CYTE and P/S. In FIG. 3 the production run is shown, where 300 ml medium was harvested from each roller bottle every day. The harvested media from the two roller bottles were pooled before a medium sample was taken out for IFNB activity determination. As shown in FIG. 3 the production run was terminated after 26 days. After a lag-period of 5 days the activity mediated by the [49N+Q51T+F111N+R113T]IFNB variant increased dramatically and for the rest of the production run the harvested IFNB activity per day, in average, was 2.4 million IU/ml×600 ml=1.440 billion IU. In total $3.2 \times 10^{10}$ IU was produced corresponding to 160 mg protein (with a hypothetical specific activity of $2 \times 10^8$ IU/mg).

Example 9

Production, Purification and PEGylation of the IFNB Variant K19R+K45R+K123R

To end up with 100 ml serum-free medium containing the IFNB variant K19R+K45R+K123R, 3 T-175 flasks were seeded with COS-7 cells in DMEM medium (Life technologies; Cat. # 21969-035) supplemented with 10% FBS plus Glutamine and penicillin/streptomycin. On the day of transfection (at nearly 100% confluency) the medium was renewed with 30 ml fresh medium 4–5 hours before the transfection. To prepare the transfection, 1890 µl DMEM medium without supplements was aliquoted into a 14 ml polypropylene tube (Corning). 210 µl Fugene 6 (Roche) was added directly into the medium and incubated for 5 min at RT. In the meantime 168 µg plasmid DNA ([K19R, K45R, K123R]IFN-β/pcDNA3.1(−)Hygro; PF #161) was aliquoted into another 14 ml polypropylene tube. After 5 min incubation the Fugene 6 mix was added directly to the DNA solution and incubated for 15 min at RT. After incubation about 700 µl was added drop wise to each of the three cell media.

Next day the transfection medium was substituted with 35 ml serum-free production medium. The serum-free medium is based on DMEM medium (Life Technologies; Cat. # 31053-028) supplemented with Glutamine, Sodium Pyruvate, penicillin/streptomycin, 1% ITSA (Life Technologies; Cat. # 51300-044), and 0.2% Ex-Cyte (Serologicals Proteins; Cat. # 81-129). Before the production medium was added the cell layers were washed two times in the DMEM medium without additives.

Three days post-transfection the 100 ml serum-free medium was harvested for purification and PEGylation of the IFNB variant.

pH was adjusted to 6.8 and conductivity adjusted to <10 mS/cm with Milli Q water. Then the broth was batch adsorbed to 1 ml SP 550 cation exchange resin (TosoHaas) preequilibrated with buffer A (20 mM phosphate, 100 mM NaCl, pH 7). After 2 h rotation end over end, the resin was allowed to sediment and transferred to a column. The resin was washed with 5 column volumes buffer A and eluted with 2 ml buffer B (20 mM phosphate, 800 mM NaCl, pH 7). The eluate was concentrated to 500 ul on VivaSpin (cutoff 10 kDa) after addition of 5% ethyleneglycol. The concentrate was adjusted to 50 mM phosphate, 0.3 M NaCl, 20% ethyleneglycol, pH 8 in a final volume of 2 ml and further concentrated to 0.5 ml.

The final concentrate was PEGylated as follows: to 100 ul of the final concentrate, 25 ul of activated mPEG-SPA (5000 kDa, Shearwater, Ala.) freshly prepared in phosphate buffer, pH 8 were added to make final concentrations of activated PEG of 0, 5, 10, 25 or 50 mg/ml. The reaction was allowed to proceed for 30 min at room temperature and then quenched by addition of 50 mM glycine buffer. Samples were frozen immediately at −80° C. and bioactivity was measured as described (Primary Assay). Western blots of each sample were performed in order to evaluate the amount of unreacted IFNB variant present in the PEGylated sample.

Results demonstrate that at 25 mg activated PEG/ml, nonPEGylated IFNB variant was absent as judged by western blot and the variant retained 50% of its bioactivity compared to the control sample (treated identically, but with 0 mg/ml activated PEG).

Example 10

Expression and Purification of Soluble IFNAR2

The cDNA's encoding the extracellular domain of IFNAR-1 and IFNAR-2 (termed IFNAR1ec and IFNAR2ec, respectively) were amplified from HeLa cell cDNA using PCR with primers corresponding to the first 10 amino acid residues and the final 10 amino acid residues of the extracellular domain of IFNAR-2 (the nucleotide sequence of which is apparent from Novick et al., Cell, Vol. 77, pp 391–400, 1994) and the first 10 amino acid residues and the final 10 amino acid residues of the extracellular domain of IFNAR-1 (the nucleotide sequence of which is apparent from Uze et al., Cell Vol. 60, 225–234, 1990). The cDNA's were subcloned into the pBlueBac 4.5/V5-His-TOPO vector (Invitrogen) and a recombinant Baculovirus obtained by homologous recombination, plaque purification, and propagation in Sf9 cells. Sf9 cells were infected with the recombinant Baculovirus and expression from the resulting cells was obtained essentially as described in Example 2.

IFNAR1ec and IFNAR2ec protein was observed in culture supernatants two to three days after infection of Sf9 cells with recombinant baculovirus. The activity of soluble receptors was observed in an Interferon antagonist assay. Briefly, Hela cells containing the ISRE element (as described in the Primary Assay above) are stimulated with a sub-maximal dose of human wild-type Interferon β in the presence of varying concentrations of IFNARec supernatant. The antagonist effect of the supernatant is directly proportional to the amount of soluble receptor present.

IFNAR2ec was purified from filtered culture supernatants using ion exchange, and affinity chromatography. Culture supernatants positive for IFNAR2ec were pH adjusted to 7.5 and loaded onto an anion exchange column, and the bound recombinant protein was eluted using 500 mM NaCl. The partially pure IFNAR2ec was then diluted and pH adjusted to 8.0, before further purification using binding to a TALON™ Metal Affinity Resin and elution with imidazol. The final preparation was frozen in aliquots. IFNAR1ec can be purified as described for IFNAR2ec with the exception that cation exchange chromatography at pH6.0 will be used as the ion exchange step.

Example 11

Use of Soluble IFNAR2 for Purification and PEGylation of Interferon-β and Variants thereof Purified IFNAR2 obtained as described in Example 9 is immobilized either through amino or carboxyl groups using e.g. CNBr-activated Sepharose 4B or EAH Sepharose 4B according to the manufacturer's instructions (Amersham Pharmacia Biotech, Affinity Chromatography, Principles and Methods, 18-1022-29, edition AB). It is critically important that the coupling method allows functional IFNAR2 to be immobilized and this is tested through optimization of the coupling conditions (pH, coupling buffer, ratio of IFNAR 2 to activate matrix etc). Another critical parameter is the blocking of excess active groups. Subsequently, testing of binding capacity by addition of interferon-β and measurement of breakthrough is carried out.

Optimally immobilized IFNAR2 is used for purification of Interferon-β as follows. A 5 ml column with 1 mg IFNAR 2 immobilized per ml gel is equilibrated with buffer A (20 mM phosphate, 300 mM NaCl, pH 7). Then the column is loaded with a 2 mg Interferon-β sample in buffer A and subsequently washed with 5 column volumes buffer A. Elution is obtained by pumping 2 column volumes of buffer B onto the column. Fractions of 1 ml are collected and assayed for bioactivity. Optimal elution conditions are dependent on the immobilization method, but examples of elution conditions include pH 1.5–3 (e.g. 0.1 M glycine pH 2.3 in 0.5 M NaCl), pH 11.5–12, 3.5 M $MgCl_2$, 6M urea or the like.

Example 12

Use of Immobilized IFNAR2 for PEGylation of Interferon β (Variants)

In addition to the use described in Example 10, immobilized IFNAR 2 may be used for optimal PEGylation, wherein PEGylation of the part of Interferon-β or variants thereof interacting with the receptor is avoided.

A 5 ml column with 1 mg IFNAR 2 immobilized per ml gel is equilibrated with buffer A (20 mM phosphate, 300 mM NaCl, pH 7). Then the column is loaded with a 2 mg Interferon-β sample in buffer A and subsequently washed with 5 column volumes buffer A. A solution of activated mPEG-SPA (1–50 mg/ml in buffer A) is pumped on the column and allowed to react for 15 min-12 h depending on temperature. One preferred range of combination of residence time and temperature is 15–60 min, 10–20° C., another is 30 min to 5 h, 2–8° C. After the indicated time period, elution is obtained by pumping 2 column volumes of buffer B onto the column. Fractions of 1 ml are collected and assayed for bioactivity using the primary screening assay. Optimal elution conditions are dependent on the immobilization method, but examples of elution conditions include pH 1.5–3 (e.g. 0.1 M glycine pH 2.3 in 0.5 M NaCl), pH 11.5–12, 3.5 M $MgCl_2$, 6M Urea or the like.

Example 13

Antiviral Activity of PEGylated Variant

The pegylated IFN-β variant protein, K19R+K45R+K123R, was assayed using the antiviral bioassay. Wild-type and variant proteins were added to A549 cells in concentrations from 10–0.0001 IU/mL in triplicate cultures.

Figure 2:
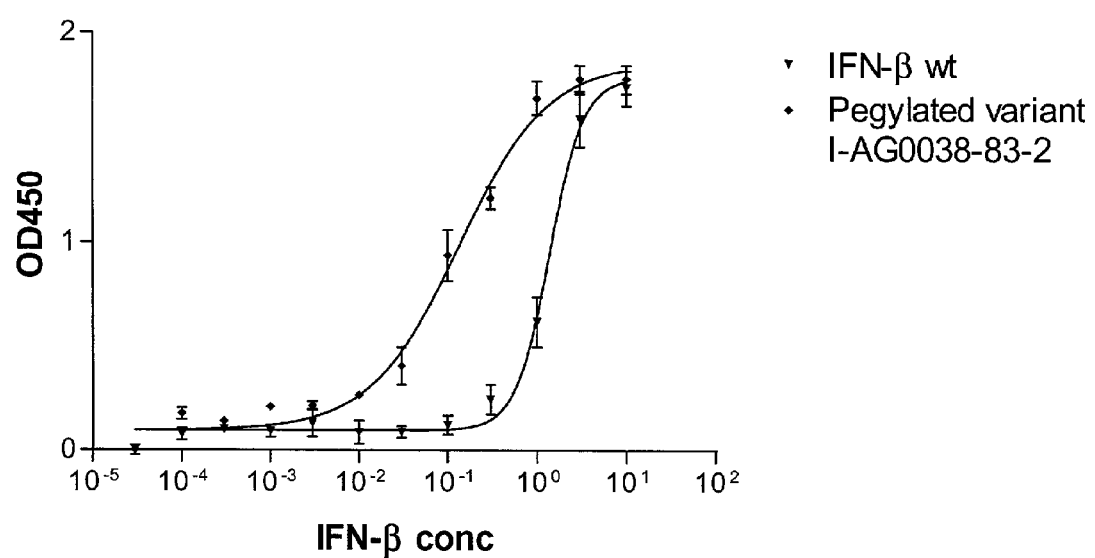
FIG. 2 illustrates the antiviral activity of a conjugate of the invention.

The pegylated IFN-β variant showed total inhibition of EMC virus induced cell death at a concentration of 3 IU/mL, with an EC50 of 0.13 IU/mL (FIG. 2). The wild-type standard shows virus inhibition with an EC50 of 1.4 IU/mL.

These results demonstrate that the pegylation of the modified interferon β polypeptide resulted in a conjugate with full anti-viral activity.

Example 14

Antibody Neutralisation of Glycosylated Variant

The antibody neutralisation of wild-type and glycosylated IFN-β variant protein, Q49N+Q51T+F111N+R113T, was assayed using the ISRE neutralisation assay. Interferon β wild-type and variant proteins (in five fold dilutions starting at 12500 IU/mL) were incubated with polyclonal rabbit anti-interferon β antibody (PBL Biomedical Laboratories) in concentrations 0, 40 and 200 ng/mL.

In the presence of 200 ng/mL polyclonal rabbit anti-serum the activity of the wild type interferon β protein was reduced 11.8 times whereas the activity of the glycosylated interferon β variant only was reduced 3.0 times. Thus the degree of antibody recognition of the interferon β variant was reduced by 75% of the wt level, see Table 1 below. These results demonstrate that the recognition of the glycosylated mutant interferon β by polyclonal antibodies raised in animals immunised with wild-type human interferon β is highly reduced. Thus, a large portion of the immunogenic epitopes in wild-type human interferon β has been removed/shielded by the modifications made in the variant molecule.

TABLE 1

| Antibody conc. (ng/mL) | Protein | EC50 | Fold inhibition | Reduction of antibody neutralisation |
|---|---|---|---|---|
| 0 | wt | 0.00039 | — | — |
|  | variant | 0.00020 | — | — |
| 40 | wt | 0.00190 | 4.8 | — |
|  | variant | 0.00020 | 1.0 | 79% |
| 200 | wt | 0.00461 | 11.8 | — |
|  | variant | 0.00059 | 3.0 | 75% |

Example 15

Construction and Expression of Interferon β Molecules with Modified N-terminus

N-terminally modified variants of interferon β were constructed as described in the preceding examples.

For the construction of an expression plasmid for the interferon β variant, IFNB S(−1)A+M1Q the following primers were used:
CBProFpr110: 5'-AAC TGG ATC CAG CCA CCA TGA CCA ACA AGT GCC TGC TCC AGA TCG CCC TGC TCC TGT GCT TCA GCA CCA CGG CCC TAG CCC AGA GCT AC-3' (SEQ ID NO:37) and CBProFpr42 (SEQ ID NO:26).

For the construction of an expression plasmid for the interferon variant, IFNβ S(−1)AQ (indicating substitution of the S residue located in position (−1) with an A and a Q residue) the following primers were used:
CBProFpr109: 5'-AAC TGG ATC CAG CCA CCA TGA CCA ACA AGT GCC TGC TCC AGA TCG CCC TGC TCC TGT GCT TCA GCA CCA CGG CCC TAG CCC AGA TGA GCT AC-3' (SEQ ID NO:38) and CBProFpr42 (SEQ ID NO:26).

To test the activity of these variants the respective plasmids; pF154 and pF163 were transfected into CHO K1 cells using Lipofectamine 2000 (Life Technologies, USA) as transfection reagent. The supernatants were harvested 24 hours post transfection and assayed in the primary activity assay and in the ELISA as described in the Materials and Methods section. The following results were obtained:

|  | IFNB S-1A + M1Q (pF154): | IFNB S-1AQ (pF163): |
|---|---|---|
| Activity: | 106410 IU/ml | 90634 IU/ml |
| ELISA: | 333 ng/ml | 193 ng/ml |
| Specific activity: | 3.2 × 10$^8$ IU/mg | 4.7 × 10$^8$ IU/mg |

These molecules are as active as wild type human interferon β.

Example 16

Preparation of Pegylated IFN-β Variants 50 microliters of a 0.3 mg/ml solution of recombinant human IFN-β polypeptide comprising the mutations Q49N+Q51T+K19R+K45R+K123R in 50 mM Na-acetate, 35% ethylene glycol, pH 5.5 were mixed with 10 μl 0.5 M Na-phosphate, pH 8.0 and 20 μl 50 mM Na-phosphate, 0.1 M NaCl, 30% ethylene glycol, pH 8.0 containing 0.02 mg/ml SPA-mPEG (N-succinimidyl Propionate methoxy polyethylene glycol). This corresponds to a 10 molar excess of SPA-mPEG to IFN-β.

After ½ hour with gentle rotation at room temperature, the reaction was quenched by addition of 5 μl 20 mM Glycine, pH 8.0. At this stage, the reaction mixture contained a mixture of unmodified as well as pegylated forms of recombinant human IFN-β.

Activity:

In vitro testing using the primary screening assay demonstrated that the pegylated material retained 40% activity, as compared to the unmodified recombinant human IFN-β.

In another experiment, 50 μl of a 0.14 mg/ml solution of recombinant human IFN β polypeptide comprising the mutations Q49N+Q51T in 50 mM Na-acetate, 35% ethylene glycol, pH 5.5 was mixed with 10 μl 0.5 M Na-phosphate, pH 8.0 and 20 μl 50 mM Na-phosphate, 0.1 M NaCl, 30% ethylene glycol, pH 8.0 containing 0.03 mg/ml SPA-mPEG. This gave a 10 molar excess of SPA-mPEG to IFN-β.

After ½ hour with gentle rotation at room temperature, the reaction was quenched by addition of 5 μl 20 mM Glycine, pH 8.0. At this stage, the reaction mixture contained a mixture of unmodified as well as pegylated forms of recombinant human IFN-β.

Activity:

In vitro testing using the primary screening assay demonstrated that the pegylated material retained 20% activity, as compared to the unmodified recombinant human IFN-β.

Example 17

Variants Having Increased Carbohydrate Attachment at Position 49

The inserted N-linked glycosylation site at position 49 in the IFNB variant [Q49N, Q51T] described in Example 6 above is used only about 60%. In order to increase the amount of attached carbohydrate the glutamine residue at position 48 was exchanged with phenylalanine (Q48F), valine (Q48V), and tryptophan (Q48W) by site-directed PCR mutagenesis. Using BIO-X-ACT (Bioline, UK) and PF185 (PF185 contains the same cDNA sequence as PF104, described in Example 6, despite the fact that a Kozak sequence has been inserted in front of the start ATG) as template, PCR reactions were performed with overlapping primer-sets:

```
Q48F, Q49N, Q51T

PBR89/                                                   (SEQ ID NO:36)
PBR148 (5'-GTCCT CCTTG GTGAA GTTGA ACAGC TGCTT; and      SEQ ID NO:39)
PBR8/                                                    (SEQ ID NO:34)
PBR147 (5'-AAGCA GCTGT TCAAC TTCAC CAAGG AGGAC;          SEQ ID NO:40)

Q48V, Q49N, Q51T

PBR89/                                                   (SEQ ID NO:36)
PBR150 (5'GTCCT CCTTG GTGAA GTTCA CCAGC TGCTT; and       SEQ ID NO:41)
PBR8/                                                    (SEQ ID NO:34)
PBR149 (5'AAGCA GCTGG TGAAC TTCAC CAAGG AGGAC;           SEQ ID NO:42)

Q48W, Q49N, Q51T

PBR89/                                                   (SEQ ID NO:36)
PBR152 (5'GTCCT CCTTG GTGAA GTTCC ACAGC TGCTT; and       SEQ ID NO:43)
PBR8/                                                    (SEQ ID NO:34)
PBR151 (5'AAGCA GCTGT GGAAC TTCAC CAAGG AGGAC;           SEQ ID NO:44)
```

The fragments were assembled in PCR reactions with the flanking primers PBR89 and PBR8. The resulting genes were inserted into the mammalian expression vector pCDNA3.1 (−)Hygro/Intron and confirmed by sequencing to have the correct base changes leading to [Q48F, Q49N, Q51T] hIFN-β (plasmid designated PF305), [Q48V, Q49N, Q51T]hIFN-β (plasmid designated PF306), and [Q48W, Q49N, Q51T]hIFN-β (plasmid designated PF307), respectively. PF305, PF306, PF307, and PF185 (encoding [Q49N, Q51T]hIFN-β) were transfected into CHO K1 cells by use of Fugene 6 (Roche) as transfection agent. 24 hours later the culture medium was harvested and assayed for IFN-β activity:

| | |
|---|---|
| PF185 | 134713 IU/ml |
| PF305 | 53122 IU/ml |
| PF306 | 65949 IU/ml |
| PF307 | 45076 IU/ml |

In order to evaluate the amount of attached carbohydrate in the three new glycosylation variants a Western blot was performed with equal amount of activity in each lane (FIG. 1; lanes 2, 3, 4, and 5). As seen in the figure the amino acid exchanges (Q48F, Q48V, Q48W) in front of the introduced glycosylation site (Q49N, Q51T) all leads to an increased amount of fully glycosylated material.

In another experiment it was seen that insertion of especially tyrosine in position 48 lead to an increased amount of attached carbohydrate to the inserted N-linked glycosylation site in position 49.

Example 18

Variants Having Increased Carbohydrate Attachment at Position 111

The inserted N-linked glycosylation site at position 111 in the IFNB variant [F111N, R113T] described in Example 5 above is used only about 50%. In order to increase the amount of attached carbohydrate the aspartic acid residue at position 110 was exchanged with phenylalanine (D110F) and valine (D110V) by site-directed PCR mutagenesis. Using BIO-X-ACT (Bioline, UK) and PF085 (described in Example 5) as template, PCR reactions were performed with overlapping primer-sets:

```
D110F, F111N, R113T:

PBR89/                                          (SEQ ID NO:36)
PBR154 (5'CAGCT TGCCG GTGGT GTTGA ACTCC TTCTC; and  SEQ ID NO:45)
PBR8/                                           (SEQ ID NO:34)
PBR153 (GAGAA GGAGT TCAAC ACCAC CGGCA AGCTG;        SEQ ID NO:46)

D110V, F111N, R113T:

PBR89/                                          (SEQ ID NO:36)
PBR156 (5'CAGCT TGCCG GTGGT GTTCA CCTCC TTCTC; and  SEQ ID NO:47)
PBR8/                                           (SEQ ID NO:34)
PBR155 (5'GAGAA GGAGG TGAAC ACCAC CGGCA AGCTG;      SEQ ID NO:48)
```

The fragments were assembled in PCR reactions with the flanking primers PBR89 and PBR8. The resulting genes were inserted into the mammalian expression vector pCDNA3.1 (−)Hygro/Intron and confirmed by sequencing to have the correct base changes leading to [D110F, F111N, R113T]hIFN-β (plasmid designated PF308) and [D110V, F111N, R113T]hIFN-β (plasmid designated PF309), respectively.

PF308, PF309 and PF085 (encoding [F111N, R113T,] hIFN-β) were transfected into CHO K1 cells by use of Fugene 6 (Roche) as transfection agent. 24 hours later the culture medium was harvested and assayed for IFN-β activity:

| | |
|---|---|
| PF085 | 58615 IU/ml |
| PF308 | 50900 IU/ml |
| PF309 | 15063 IU/ml |

In order to evaluate the amount of attached carbohydrate in the two new glycosylation variants a Western blot was performed with equal amount of activity in each lane (FIG. 1; lanes 7, 8, 9). As seen in the figure the amino acid exchanges (D110F and D110V) in front of the introduced glycosylation site (F111N, R113T) both leads to a significantly increased amount of fully glycosylated material.

In another experiment it was seen that insertion of especially tyrosine in position 110 lead to an increased amount of attached carbohydrate to the inserted N-linked glycosylation site in position 111.

Example 19

Separation of IFNB Polypeptide Glycoforms

Hydroxyapatite chromatography is an efficient means for separation of IFNB glycoforms and e.g. obtaining glycoforms with fully utilized glycosylation sites. This is illustrated in the present example.

The IFNB variant [Q49N+Q51T+F111N+R113T] produced as described in Example 8 above was purified in a three-step procedure:

The harvested media from roller bottles was centrifuged and filtered through a 0.22 um filter (PVDF). The filtrated media was diafiltrated on a Vivaflow 200 system equipped with a polyethersulfon membrane with cut off 10000 and applied to a S-Sepharose column (Pharmacia) equilibrated with 50 mM sodium acetate, 50 mM sodium chloride, pH 5.5. The interferon variant bound to the column was eluted with 50 mM sodium acetate, 0.5 M sodium chloride, pH 5.5. The concentration of sodium chloride in the eluate from the S-Sepharose column was adjusted to 1.0 M and the sample was applied on a Phenyl-Sepharose High Performance column (Pharmacia) equilibrated with 50 mM sodium acetate, 1.0 M sodium chloride, pH 5.5. Following application the column was washed with Milli Q water. The IFNB variant was eluted with a gradient from Milli Q water to 60% ethylene glycol, 50 mM sodium acetate, pH 5.5 in 30 column volumes. Fractions containing fully glycosylated IFNB variant were collected and the buffer in the eluate was changed to 15 mM sodium phosphate buffer, pH 7.2. The sample was applied on a hydroxyapatite column (CHT II, Ceramic hydroxyapatite, Type II, Biorad) equilibrated with 15 mM sodium phosphate. The fully glycosylated form passed through the column where as the underglycosylated form with one extra site used bound to the column and was eluted with a linear sodium phosphate gradient from 15 mM to 200 mM in 20 column volumes.

The purity of fully glycosylated [Q49N+Q51T+F111N+R113T] IFNB was judged to be higher than 95% based on SDS-PAGE.

Example 20

PEGylation of IFNB with Introduced Glycosylation Sites

A fresh stock solution of SCM-PEG (succinimidyl ester of carboxymethylated PEG from Shearwater, Ala., 5 kD or 12 kD) was prepared in methanol before each experiment.

100 microliter of a 0.3 mg/ml solution of the glycovariant [Q49N+Q51T+F111N+R113T] IFNB in 50 mM sodium phosphate, 100 mM sodium chloride, pH 7.0 were PEGylated with SCM-PEG, 5 kD or 12 kD, with two times molar surplus of PEG to possible PEGylation sites, i.e. lysines and N-terminus. After incubation for 30 min at room temperature, the reaction was quenched by addition of 5 μl 20 mM glycine, pH 8.0. At this stage, the reaction mixture contained a minor part of unmodified protein judged by SDS-PAGE.

In vitro testing using the primary screening assay demonstrated that the pegylated material retained 40% activity with 1–3 groups of 12 kD PEG attached. With 1–3 groups of 5 kD PEG attached the retained bioactivity was 25%.

In another experiment 50 μl of purified [Q49N+Q51T+F111N+R113T+K19R+K45R+K123R] IFNB with a protein concentration of 0.1 mg/ml was PEGylated in 50 mM sodium phosphate, 100 mM sodium chloride, pH 8.0 with SCM-PEG, 5 kD, with 20 times molar excess of PEG to possible PEGylation sites, i.e. lysines and N-terminus. After incubation for 30 min at room temperature, the reaction was quenched by addition of 5 μl 20 mM glycine, pH 8.0. At this stage, the reaction mixture contained a minor part of unmodified protein judged by SDS-PAGE.

In vitro testing using the primary screening assay demonstrated that the pegylated material retained 45% activity with 1–3 groups of 5 kD PEG attached. A higher molar surplus of PEG was needed to PEGylate variants in which one or several lysines were substituted with other amino acid residues.

Pegylated material was separated from unpegylated material and surplus of PEG using either size-exclusion chromatography or cation exchange chromatography or a combination of both. Size-exclusion chromatography was performed with a Superose 12 or Superdex 75 column from Pharmacia equilibrated with PBS buffer, pH 7.2. Cation exchange chromatography was performed on SP-Sepharose HP (Pharmacia) equilibrated with 20 mM citrate, pH 2.7. Elution from the SP-Sepharose HP column was performed either by increasing the concentration of salt (e.g. sodium chloride) or by increasing the pH of the buffer (e.g. sodium acetate or sodium phosphate).

Example 21

Hyper-Glycosylated IFNB Variant is Stabilised by Substitution of the Cysteine in Position 17 with Serine CHOK1 cells were transfected with plasmids encoding two hyper-glycosylated IFNB variants: [S2N, N4T, Q51N, E53T]IFNB (PF276) and [S2N, N4T, C17S, Q51N, E53T] IFNB (PF279). Confluent stable primary transfectionpools were expanded into four T-175 flasks each. At confluency, the flasks were shifted from serum containing medium to a serum-free medium based on DMEM/F-12 medium (Lifetechnologies #21045-025) supplemented with 1/100 ITSA (Life Technologies #51300-044) and 1/1000 Ex-Cyte (Serologicals Corp. #81-129). Every day. in 15 days, 120 ml of each variant was harvested and frozen at −80° C.

The supernatants from the daily harvest were collected and filtered through 0.22 um filter (PVDF based). The supernatant was concentrated approximately 15 times on a Vivaflow 200 system equipped with a polyethersulfon membrane with cut-off 10000 and the concentrated sample was applied on a S-Sepharose column equilibrated with 50 mM sodium acetate, 50 mM NaCl, pH 5.5 The IFNB variant eluted in a step with 50 mM sodium acetate, 0.5 M NaCl, pH 5.5.

The concentration of sodium chloride in the eluate from the S-Sepharose column was adjusted to 1.0 M and the sample was applied on a Phenyl-Sepharose column equilibrated with 50 mM sodium acetate, 1.0 M sodium chloride, pH 5.5. Extensive washing with the equilibration buffer was carried out before the IFNB variant was eluted with 60% ethylene glycol in 50 mM sodium acetate, pH 5.5.

Unreduced SDS-PAGE following the purification clearly demonstrated the formation of dimer with [S2N, N4T, Q51N, E53T]IFNB where as no dimer was present with [S2N, N4T, C17S, Q51N, E53T]IFNB.

Example 22

Production, Purification and PEGylation of [C17S+Q49N+Q51T+D110F+F111N+R113T]IFNB Glycosylation Variant A CHOK1 sub-clone (5/G-10) producing [C17S+Q49N+Q51T+D110F+F111N+R113T]IFNB glycosylation variant was seeded into 6 roller bottles, each with an expanded surface of 1700 $cm^2$ (Corning, USA), in 200 ml DMEM/F-12 medium (LifeTechnologies; Cat. # 31330) supplemented with 10% FBS and penicillin/streptomycin (P/S). After 2 days the medium was exchanged. After another 2 days the two roller bottles were nearly 100% confluent and the medium was shifted to 300 ml serum-free UltraCHO medium (BioWhittaker; Cat. # 12-724) supplemented with 1/500 EX-CYTE (Serologicals Proteins; Cat. # 81129N) and P/S. Growing the cells in this medium promotes a higher cell mass, higher than can be achieved in the serum containing medium. After 2 days the medium was renewed. After another 2 days the medium was shifted to the production medium: DMEM/F-12 medium (Life Technologies; Cat. # 21041) supplemented with 1/100 ITSA (Life Technologies; Cat. # 51300-044) [ITSA stands for Insulin (1.0 g/L)—Transferrin (0.55 g/L)—Selenium (0.67 mg/L) supplement for Adherent cultures], 1/500 EC-CYTE and P/S. The harvested media from the roller bottles were pooled before a medium sample was taken out for IFNB activity determination. Every day, in 21 days, 1.8 l medium was harvested and frozen at −80° C.

The harvested media from roller bottles was centrifuged and filtered through a 0.22 μm filter (PVDF). The filtrated media was diafiltrated on a Vivaflow 200 system equipped with a polyethersulfon membrane with cut off 10000 and applied to a S-Sepharose column (Pharmacia). The S-Sepharose column was equilibrated with 50 mM sodium acetate, 50 mM sodium chloride, pH 5.5 and the interferon variant was eluted with 50 mM sodium acetate, 0.5 M sodium chloride, pH 5.5. The concentration of sodium chloride in the eluate was adjusted to 1.0 M.

The eluate from the S-Sepharose column was applied on a Phenyl-Sepharose High Performance column (Pharmacia) equilibrated with 50 mM sodium acetate, 1.0 M sodium chloride, pH 5.5. Following application the column was washed with 50 mM sodium acetate, 50 mM sodium chloride, pH 5.5. The IFNB variant was eluted with a gradient from 50 mM sodium acetate, 50 mM sodium chloride, pH 5.5 to 60% ethylene glycol, 50 mM sodium acetate, pH 5.5 in 30 column volumes. Fractions containing fully glycosylated IFNB variant were collected and pooled.

The ethylene glycol in the eluate from the Phenyl-Sepharose was removed by passing the eluate through a S-Sepharose column equilibrated with 50 mM sodium acetate, 50 mM sodium chloride, pH 5.5. The ethylene glycol was in the flow through where as the interferon variant bound to the column. Following application the column was washed with 20 mM sodium acetate, pH 5.5 and the interferon variant was eluted with 100 mM sodium phosphate, pH 7.5.

The phosphate concentration in the eluate was adjusted to 15 mM sodium phosphate buffer, pH 7.2. and applied on a hydroxyapatite column (CHT I, Ceramic hydroxyapatite, Type I, Biorad) equilibrated with 15 mM sodium phosphate, pH 7.2. The fully glycosylated form passed through the column where as the underglycosylated form with one extra site used bound to the column and was eluted with a linear sodium phosphate gradient from 15 mM to 200 mM sodium phosphate, pH 6.8 in 20 column volumes.

The purity of the fully glycosylated variant [C17S+Q49N+Q51T+D110F+F111N+R113T]IFNB was judged to be higher than 95% based on SDS-PAGE.

Following purification the variant was PEGylated. A fresh stock solution of 10 mg/ml SCM-PEG (succinimidyl ester of carboxymethylated PEG from Shearwater, Ala., 12 K or 20 K) was prepared in 96% ethanol before each experiment.

A protein solution of 0.1 mg/ml in 20 mM sodium phosphate, pH 7.0 was PEGylated with SCM-PEG, 20K, with 0.75 times molar surplus of PEG to possible PEGylation sites, i.e. lysines and N-terminus. After incubation for 30 min at room temperature, the reaction was quenched by addition of a surplus of 20 mM glycine, pH 8.0. The reaction mixture contained a mixture of mono-, di- and un-pegylated material. Mono-pegylaled material was separated from other species using either cation exchange chromatography or size-exclusion chromatography or a combination of both. pH in the PEGylation solution was adjusted to pH 2.7 and the sample was applied on a SP-Sepharose HR (Pharmacia) column equilibrated with 20 mM sodium citrate, pH 2.7. The pegylared protein was eluted from the column with 50 mM sodium acetate containing 1 M sodium chloride and applied on a size-exclusion column, Sephacryl S-100, ((16/60) Pharmacia) equilibrated with 100 mM sodium acetate, 200 mM sodium chloride, pH 5.5. Fractions containing mono-pegylated material were pooled and characterized further.

In another experiment a protein solution of 0.16 mg/ml in 20 mM sodium phosphate, pH 7.0 was PEGylated with SCM-PEG, 12K, with 2 times molar surplus of PEG to possible PEGylation sites, i.e. lysines and N-terminus. After incubation for 30 min at room termperature, the reaction was quenched by addition of a surplus of 20 mM glycine, pH 8.0. The reaction mixture contained a mixture of mono-, di-, tri-pegylated material together with underivatized material. The pegylated material was separated from the unmodified protein using either cation exchange chromatography or size-exclusion chromatography or a combination of both. pH in the PEGylation solution was adjusted to pH 2.7 and the sample was applied on a SP-Sepharose HR (Pharmacia) column equilibrated with 20 mM sodium citrate, pH 2.7. The pegylated protein was eluted from the column with 50 mM sodium acetate containing 1 M sodium chloride and applied on a size-exclusion column, Sephacryl S-100, ((16/60) Pharmacia) equilibrated with 100 mM sodium acetate, 200 mM sodium chloride, pH 5.5. Fractions containing the mixture of mono-, di- and tri-pegylated protein were pooled and characterized further.

Example 23

Production, Purification and PEGylation of [C17S+K19R+K33R+K45R+Q49N+Q51T+D110F+F111N+R113T] IFNB Glycosylation Variant in Roller Bottles A CHOK1 sub-clone (5/G-10) producing [C17S+K19R+K33R+K45R+Q49N+Q51T+D110F+F111N+R113T]IFNB glycosylation variant was produced in 6 roller bottles as described in example 22 and purified according to the protocol used in example 22. The purity of the fully glycosylated variant [C17S+K19R+K33R+K45R+Q49N+Q51T+D110F+F111N+R113T]IFNB was judged to be higher than 95% based on SDS-PAGE.

Following purification the variant was PEGylated. A fresh stock solution of SCM-PEG (succinimidyl ester of carboxymethylated PEG from Shearwater, Ala., 12 kD or 20 kD) was prepared in ethanol before each experiment.

A protein solution of 0.1 mg/ml in 20 mM sodium phosphate, pH 7.0 was PEGylated with SCM-PEG, 20K, with 3 times molar surplus of PEG to possible PEGylation sites, i.e. lysines and N-terminus. After incubation for 30 min at room termperature, the reaction was quenched by addition of a surplus of 20 mM glycine, pH 8.0. The reaction mixture contained a mixture of mono-, di- and un-pegylated material. Mono-pegylated material was separated from other species using either cation exchange chromatography or size-exclusion chromatography or a combination of both. pH in the PEGylation solution was adjusted to pH 2.7 and the sample was applied on a SP-Sepharose HR (Pharmacia) column equilibrated with 20 mM sodium citrate, pH 2.7. The pegylated protein was eluted from the column with 50 mM sodium acetate containing 1 M sodium chloride and applied on a size-exclusion column, Sephacryl S-100, ((16/60) Pharmacia) equilibrated with 100 mM sodium acetate, 200 mM sodium chloride, pH 5.5. Fractions containing mono-pegylated material was pooled and characterized further In another experiment a protein solution of 0.1 mg/ml in 20 mM sodium phosphate, pH 7.0 was PEGylated with (10 mg/ml) SCM-PEG, 12K, with 5 times molar surplus of PEG to possible PEGylation sites, i.e. lysines and N-terminus. After incubation for 30 min at room termperature, the reaction was quenched by addition of a surplus of 20 mM glycine, pH 8.0. The reaction mixture contained a mixture of mono-, di-, tri-pegylated material together with underivatized material. The pegylated material was separated from the unmodified protein using either cation exchange chromatography or size-exclusion chromatography or a combination of both. pH in the PEGylation solution was adjusted to pH 2.7 and the sample was applied on a SP-Sepharose HR (Pharmacia) column equilibrated with 20 mM sodium citrate, pH 2.7. The pegylated protein was eluted from the column with 50 mM sodium acetate containing 1 M sodium chloride and applied on a size-exclusion column, Sephacryl S-100, ((16/60) Pharmacia) equilibrated with 100 mM sodium acetate, 200 mM sodium chloride, pH 5.5. Fractions containing the mixture of mono-, di- and tri-pegylated protein were pooled and characterized further.

While the foregoing invention has been described in some detail for purposes of clarity and understanding, it will be clear to one skilled in the art from a reading of this disclosure that various changes in form and detail can be made without departing from the true scope of the invention. It is understood that the examples and embodiments described herein are for illustrative purposes only and that various modifications or changes in light thereof will be suggested to persons skilled in the art and are to be included within the spirit and purview of this application and scope of the appended claims. For example, all the techniques and apparatus described above may be used in various combinations. All publications, parents, patent applications, and/or other documents cited in this application are incorporated herein by reference in their entirety for all purposes to the same extent as if each individual publication, patent, patent application, and/or other document were individually indicated to be incorporated herein by reference in its entirety for all purposes.

The invention claimed is:

1. An interferon β polypeptide variant exhibiting interferon β activity, comprising a variant sequence which differs from the wild-type human interferon β sequence SEQ ID NO:2 in no more than 8 amino acid residues, the variant sequence comprising (a) at least one introduced N-glycosylation site comprising two amino acid substitutions relative to SEQ ID NO:2 selected from the group consisting of Q49N+Q51T/S and F111N+R113T/S, and (b) an amino acid substitution at position −1 relative to at least one of the introduced N-glycosylation site(s).

2. The variant according to claim 1, further comprising at least one naturally occurring N-glycosylation site.

3. The variant according to claim 1, wherein the variant comprises at least two introduced N-glycosylation sites.

4. The variant according to claim 3, wherein the at least two introduced N-glycosylation sites comprise substitutions Q49N+Q51T/S and F111N+R113T/S.

5. The variant according to claim 4, wherein the amino acid substitution at position −1 relative to the introduced N-glycosylation site comprising substitutions Q49N+Q51T/S is selected from the group consisting of Q48F, Q48V, Q48W, and Q48Y and the amino acid substitution at position −1 relative to die introduced N-glycosylation site comprising substitutions F111N+R113T/S is selected from the group consisting of D110F, D110V, D110W, and D110Y.

6. The variant according to claim 5, further comprising the amino acid substitution C17S.

7. The variant according to claim 1, further comprising at least one non-polypeptide moiety covalently attached to the variant.

8. The variant according to claim 7, comprising at least one sugar moiety and at least one polymer molecule.

9. The variant according to claim 8, wherein a least one of the polymer molecule(s) is covalently attached to a lysine residue of the variant.

10. The variant according to claim 8, wherein at least one of the polymer molecule(s) is covalently attached to the N-terminus of the variant.

11. The variant according to claim 8, wherein the polymer molecule comprises a linear polyethylene glycol or a branched polyethylene glycol.

12. A composition comprising the variant of claim 1 or 7 and a diluent, carrier, or excipient.

13. The composition of claim 12, wherein the diluent, carrier or excipient is a pharmaceutically acceptable diluent, carrier, or excipient.

14. The variant according to claim 1, wherein the at least one introduced N-glycosylation site comprises substitutions Q49N+Q51T/S relative to SEQ ID NO:2.

15. The variant according to claim 14, wherein the amino acid substitution at position −1 relative to the at least one introduced N-glycosylation site comprising substitutions Q49N+Q51T/S is selected from the group consisting of Q48F, Q48V, Q48W, and Q48Y.

16. The variant according to claim 1, wherein the at least one introduced N-glycosylarion site comprises substitutions F111N+R113T/S relative to SEQ ID NO:2.

17. The variant according to claim 16, wherein the amino acid substitution at position −1 relative to the at least one introduced N-glycosylation site comprising substitutions F111N+R113T/S is selected from the group consisting of D110F, D110V, D110W, and D110Y.

18. The variant according to claim 17, wherein the amino acid substitution at position −1 relative to the at least one introduced N-glycosylation site comprising substitutions F111N+R113T/S is D110F.

19. The variant according to claim 1, further comprising the amino acid substitution C17S.

* * * * *

UNITED STATES PATENT AND TRADEMARK OFFICE
CERTIFICATE OF CORRECTION

| | | |
|---|---|---|
| PATENT NO. | : 7,144,574 B2 | Page 1 of 1 |
| APPLICATION NO. | : 10/084706 | |
| DATED | : December 5, 2006 | |
| INVENTOR(S) | : Poul Baad Rasmussen et al. | |

It is certified that error appears in the above-identified patent and that said Letters Patent is hereby corrected as shown below:

In claim 5, Column 107, line 55, delete "die" and insert --the--.

Signed and Sealed this

Fifteenth Day of May, 2007

JON W. DUDAS
*Director of the United States Patent and Trademark Office*